United States Patent
Mauzerall et al.

(10) Patent No.: US 10,413,628 B2
(45) Date of Patent: *Sep. 17, 2019

(54) MOBILE STERILIZATION APPARATUS AND METHOD FOR USING THE SAME

(71) Applicant: PMBS, LLC, St. Petersburg, FL (US)

(72) Inventors: Michele Mauzerall, St. Petersburg, FL (US); Maryellen Keenan, Nutley, NJ (US)

(73) Assignee: PMBS, LLC, St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/119,726

(22) Filed: Aug. 31, 2018

(65) Prior Publication Data

US 2019/0030198 A1    Jan. 31, 2019

Related U.S. Application Data

(63) Continuation of application No. 15/663,230, filed on Jul. 28, 2017, now Pat. No. 10,086,100.

(51) Int. Cl.
    *A47B 77/06* (2006.01)
    *A61L 2/26* (2006.01)
    *A61L 2/06* (2006.01)
    *A61L 2/07* (2006.01)

(52) U.S. Cl.
    CPC ...... *A61L 2/26* (2013.01); *A61L 2/06* (2013.01); *A61L 2/07* (2013.01); *A61L 2202/122* (2013.01); *A61L 2202/14* (2013.01); *A61L 2202/16* (2013.01); *A61L 2202/24* (2013.01)

(58) Field of Classification Search
    CPC .......... Y10T 16/541; E05D 3/12; E05D 3/122

USPC ................................ 312/229, 236, 200, 201
See application file for complete search history.

(56) References Cited

U.S. PATENT DOCUMENTS

| 4,450,968 A | 5/1984 | Muellner |
| 4,626,971 A | 12/1986 | Schultz |
| 4,643,303 A | 2/1987 | Arp et al. |
| 4,670,227 A | 6/1987 | Smith |
| 4,762,688 A | 8/1988 | Berry, Jr. |

(Continued)

FOREIGN PATENT DOCUMENTS

| CN | 201050842 | 4/2008 |
| EP | 1566185 | 8/2005 |

(Continued)

OTHER PUBLICATIONS

U.S. Appl. No. 15/663,230, filed Jul. 28, 2017.
U.S. Appl. No. 15/369,713, filed Dec. 5, 2016.
U.S. Appl. No. 14/644,094, filed Mar. 10, 2015.

*Primary Examiner* — Matthew W Ing
(74) *Attorney, Agent, or Firm* — Levine Bagade Han LLP

(57) ABSTRACT

A sterilization cabinet, comprising a top panel, at least two side panels, and a floor panel forming a part of a chamber of the sterilization cabinet; at least one door connected to at least one of the at least two side panels of the sterilization cabinet; a vent formed in at least one of the two side panels; at least one first filter covering the vent and a filter cover configured to hold the first filter against the vent; a drain positioned in the floor panel, wherein the floor panel has a slope configured to cause condensate within the chamber to flow into the drain and wherein the drain is the only outlet for the condensate along the floor panel; and a second filter covering the drain such that condensate flowing into the drain passes through the second filter.

20 Claims, 52 Drawing Sheets

(56) References Cited

U.S. PATENT DOCUMENTS

| | | |
|---|---|---|
| 4,783,321 A | 11/1988 | Spence |
| 4,915,918 A | 4/1990 | Nichols |
| 4,955,318 A | 9/1990 | Melhorn et al. |
| 4,997,240 A | 3/1991 | Schmalzl et al. |
| 5,019,345 A | 5/1991 | Lorenz |
| 5,202,098 A | 4/1993 | Nichols |
| 5,205,627 A | 4/1993 | Davison et al. |
| 5,223,229 A | 6/1993 | Brucker |
| 5,232,277 A | 8/1993 | Cassady et al. |
| 5,281,400 A | 1/1994 | Berry, Jr. |
| 5,324,489 A | 6/1994 | Nichols et al. |
| 5,346,075 A | 9/1994 | Nichols et al. |
| 5,369,892 A | 12/1994 | Dhaemers |
| 5,415,846 A | 5/1995 | Berry, Jr. |
| 5,523,519 A | 6/1996 | Weber et al. |
| 5,535,141 A | 7/1996 | Lussi |
| 5,588,623 A | 12/1996 | Leduc |
| 5,843,388 A | 12/1998 | Arroyo et al. |
| 5,893,618 A | 4/1999 | LePage et al. |
| 5,923,432 A | 7/1999 | Kral |
| 5,968,459 A | 10/1999 | Nalepa et al. |
| 6,000,486 A | 12/1999 | Romick et al. |
| 6,073,547 A | 6/2000 | Westbrooks, Jr. et al. |
| 6,164,738 A | 12/2000 | Dane et al. |
| 6,218,796 B1 | 4/2001 | Kozlowski |
| 6,319,479 B1 | 11/2001 | Houston |
| 6,622,862 B1 | 9/2003 | Corrado |
| 6,789,815 B2 | 9/2004 | Moss et al. |
| 6,867,393 B1 | 3/2005 | Lewis |
| 6,926,874 B2 | 8/2005 | Ongaro |
| 7,001,441 B2 | 2/2006 | Bauer |
| 7,214,354 B2 | 5/2007 | Ongaro |
| 7,544,915 B2 | 6/2009 | Hu |
| 8,100,281 B2 | 1/2012 | Sands et al. |
| 8,454,901 B1 | 6/2013 | Snyder |
| 8,505,959 B2 | 8/2013 | Darling |
| 9,439,992 B2 | 9/2016 | Webb et al. |
| 9,616,143 B2 | 4/2017 | Snyder et al. |
| 9,694,093 B2 | 7/2017 | Snyder et al. |
| 9,724,439 B2 | 8/2017 | Webb et al. |
| 9,808,545 B2 | 11/2017 | Mauzerall et al. |
| 9,833,524 B2 | 12/2017 | Mauzerall et al. |
| 10,086,100 B1 | 10/2018 | Mauzerall et al. |
| 10,111,972 B2 | 10/2018 | Mauzerall et al. |
| 10,166,305 B2 | 1/2019 | Mauzerall et al. |
| 10,179,183 B2 | 1/2019 | Snyder et al. |
| 2003/0116636 A1 | 6/2003 | Burkett et al. |
| 2004/0011689 A1 | 1/2004 | Bauer |
| 2004/0096355 A1 | 5/2004 | Ishibiki |
| 2004/0101456 A1 | 5/2004 | Kuroshima et al. |
| 2004/0227315 A1 | 11/2004 | Van |
| 2005/0132924 A1 | 6/2005 | Bothun et al. |
| 2005/0153052 A1 | 7/2005 | Williams et al. |
| 2006/0032770 A1 | 2/2006 | Orbay et al. |
| 2006/0108757 A1 | 5/2006 | Brookmire et al. |
| 2006/0249313 A1 | 11/2006 | Kamen et al. |
| 2007/0039294 A1 | 2/2007 | Airey |
| 2007/0160494 A1 | 7/2007 | Sands |
| 2008/0063580 A1 | 3/2008 | von Lersner |
| 2008/0087231 A1 | 4/2008 | Gabriel et al. |
| 2008/0172295 A1 | 7/2008 | Watson |
| 2010/0078905 A1 | 4/2010 | Holtan |
| 2012/0082589 A1 | 4/2012 | Ladison et al. |
| 2013/0272925 A1 | 10/2013 | Ozdamar |
| 2013/0322004 A1 | 12/2013 | Park |
| 2014/0030144 A1 | 1/2014 | Krosney et al. |
| 2014/0079589 A1 | 3/2014 | Landgrebe et al. |
| 2015/0023839 A1 | 1/2015 | Snyder et al. |
| 2015/0078960 A1 | 3/2015 | Krosney et al. |
| 2015/0107627 A1 | 4/2015 | Snyder et al. |
| 2015/0209455 A1 | 7/2015 | Turbett et al. |
| 2015/0209456 A1 | 7/2015 | Turbett |
| 2015/0209462 A1 | 7/2015 | Turbett et al. |
| 2015/0284018 A1 | 10/2015 | Krosney |
| 2015/0314026 A1 | 11/2015 | Mauzerall et al. |
| 2016/0008503 A1 | 1/2016 | Webb et al. |
| 2016/0346415 A1 | 12/2016 | Webb et al. |
| 2017/0080115 A1 | 3/2017 | Mauzerall et al. |
| 2017/0128602 A1 | 5/2017 | Snyder et al. |
| 2017/0189843 A1 | 7/2017 | Turbett et al. |
| 2017/0274107 A1 | 9/2017 | Snyder et al. |
| 2018/0015190 A1 | 1/2018 | Turbett |
| 2018/0021464 A1 | 1/2018 | Mauzerall et al. |
| 2018/0085480 A1 | 3/2018 | Mauzerall et al. |
| 2018/0221803 A1 | 8/2018 | Turbett et al. |
| 2019/0060494 A1 | 2/2019 | Mauzerall et al. |

FOREIGN PATENT DOCUMENTS

| | | |
|---|---|---|
| EP | 1839683 | 10/2007 |
| FR | 2807325 | 10/2001 |
| WO | WO 2007/000639 | 1/2007 |
| WO | WO 2010/128408 | 11/2010 |
| WO | WO 2015/153084 | 10/2015 |
| WO | WO 2019/023710 | 1/2019 |

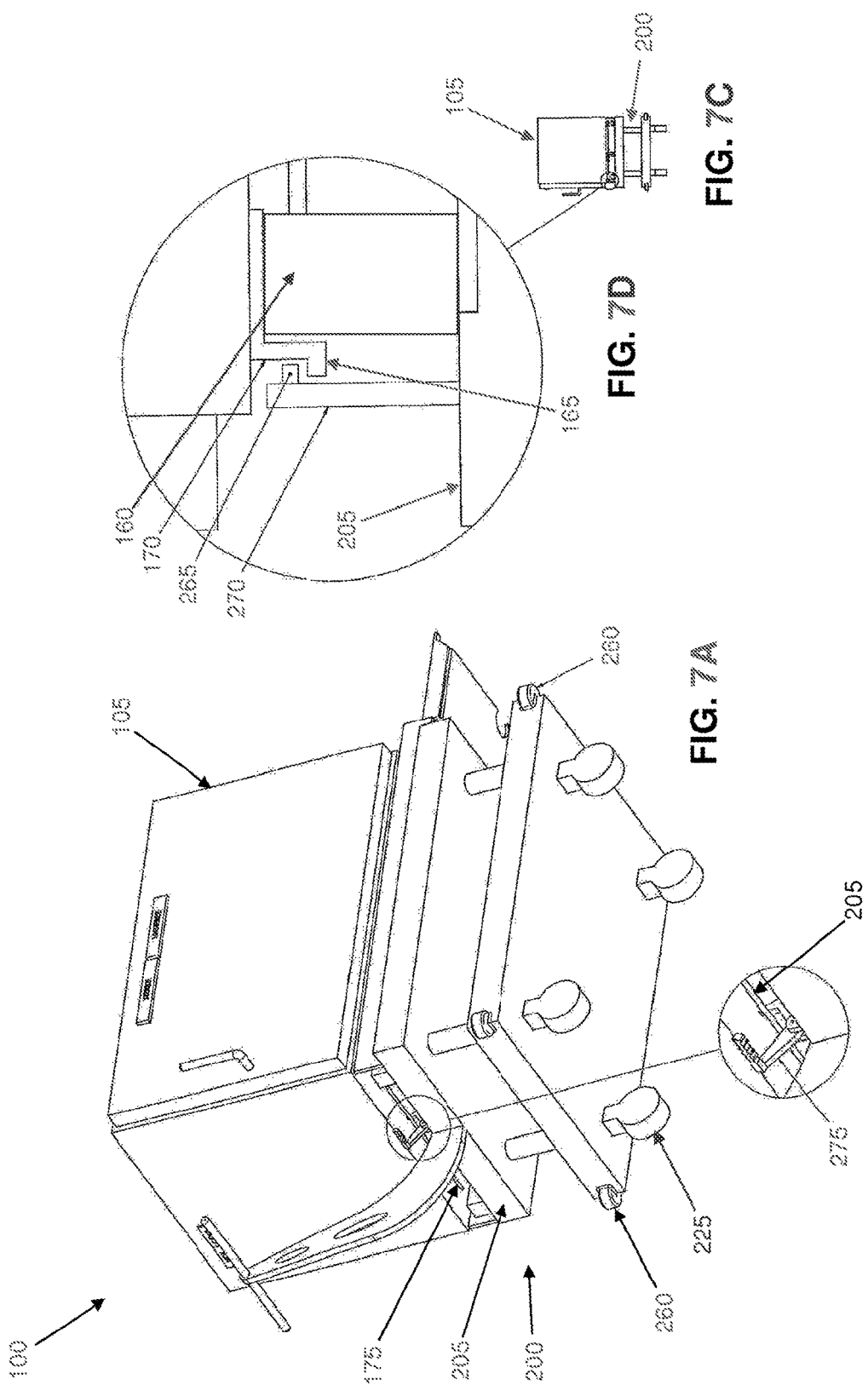

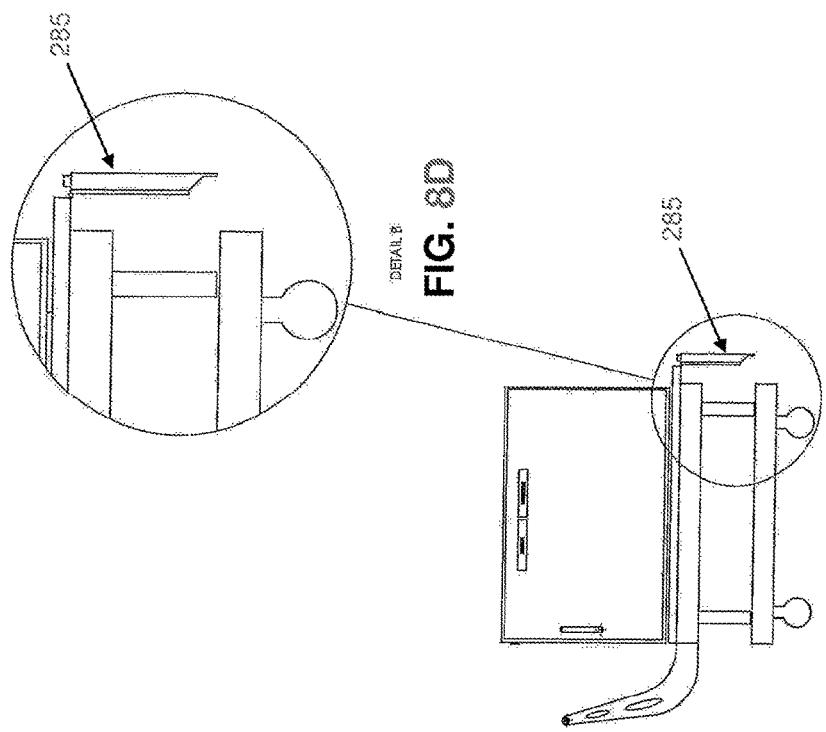
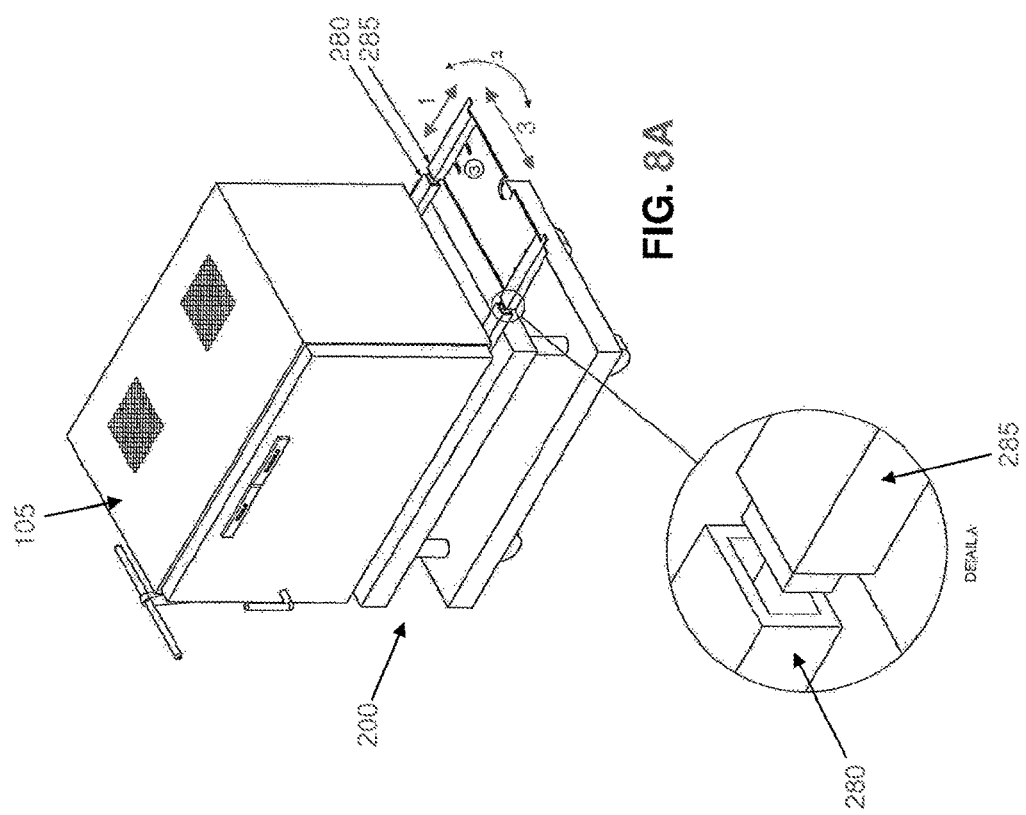

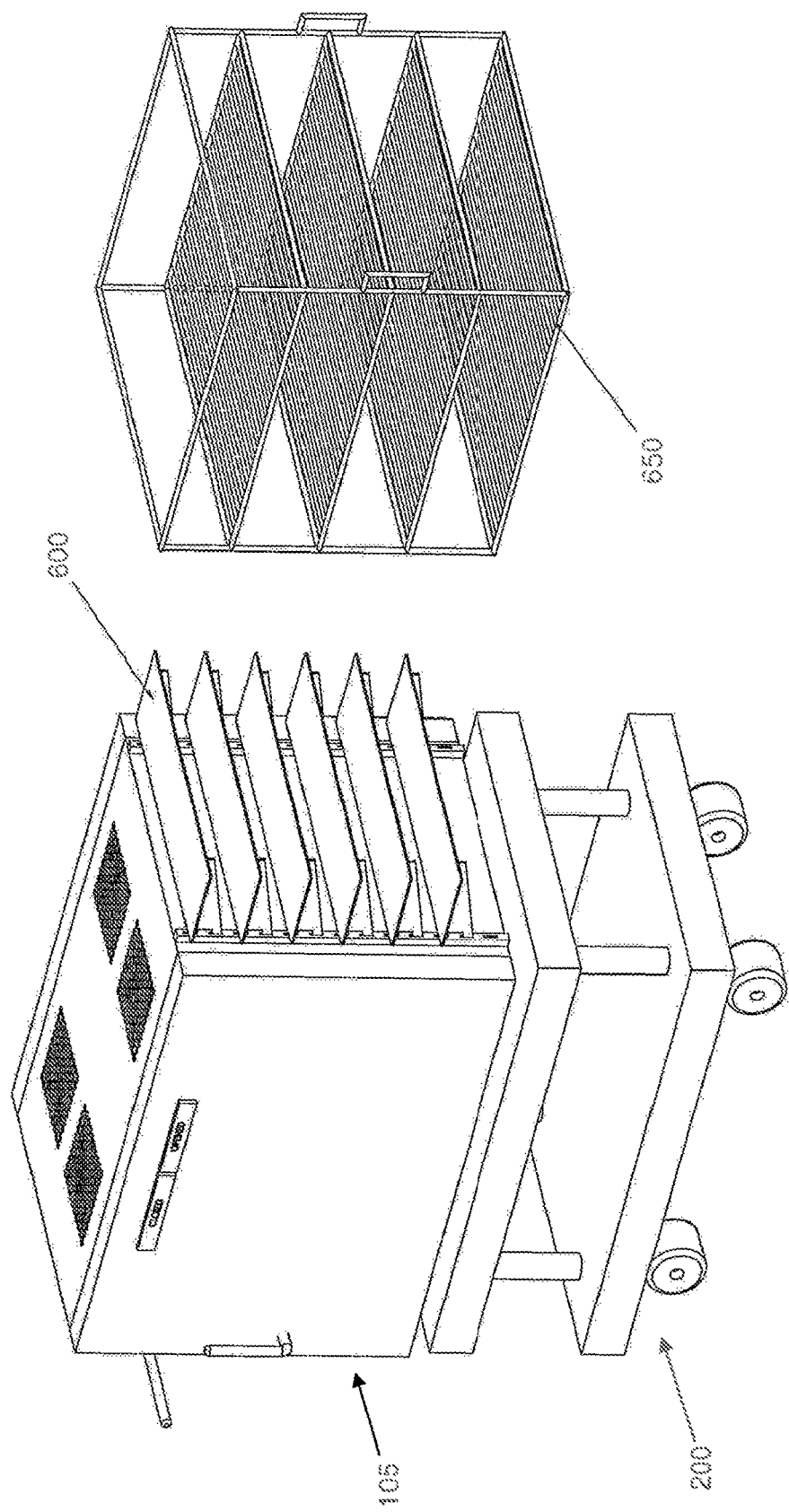

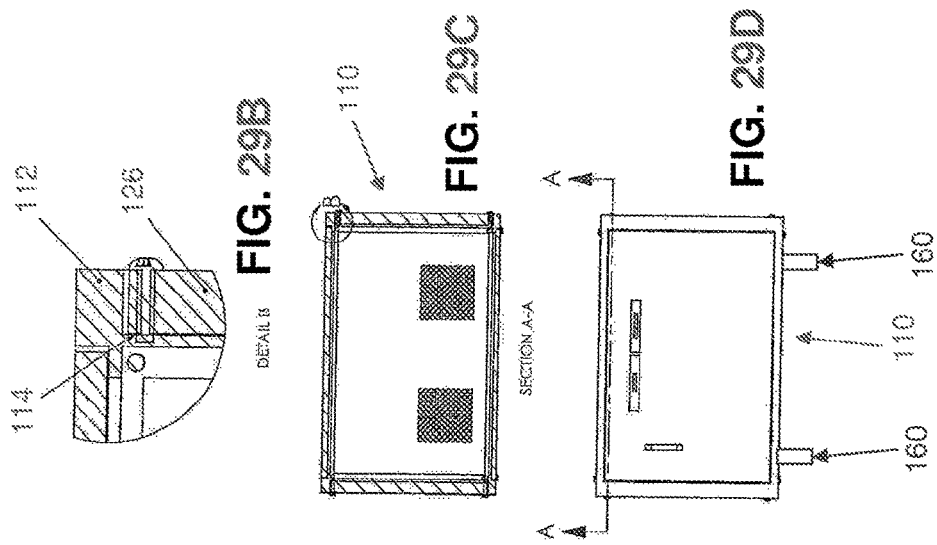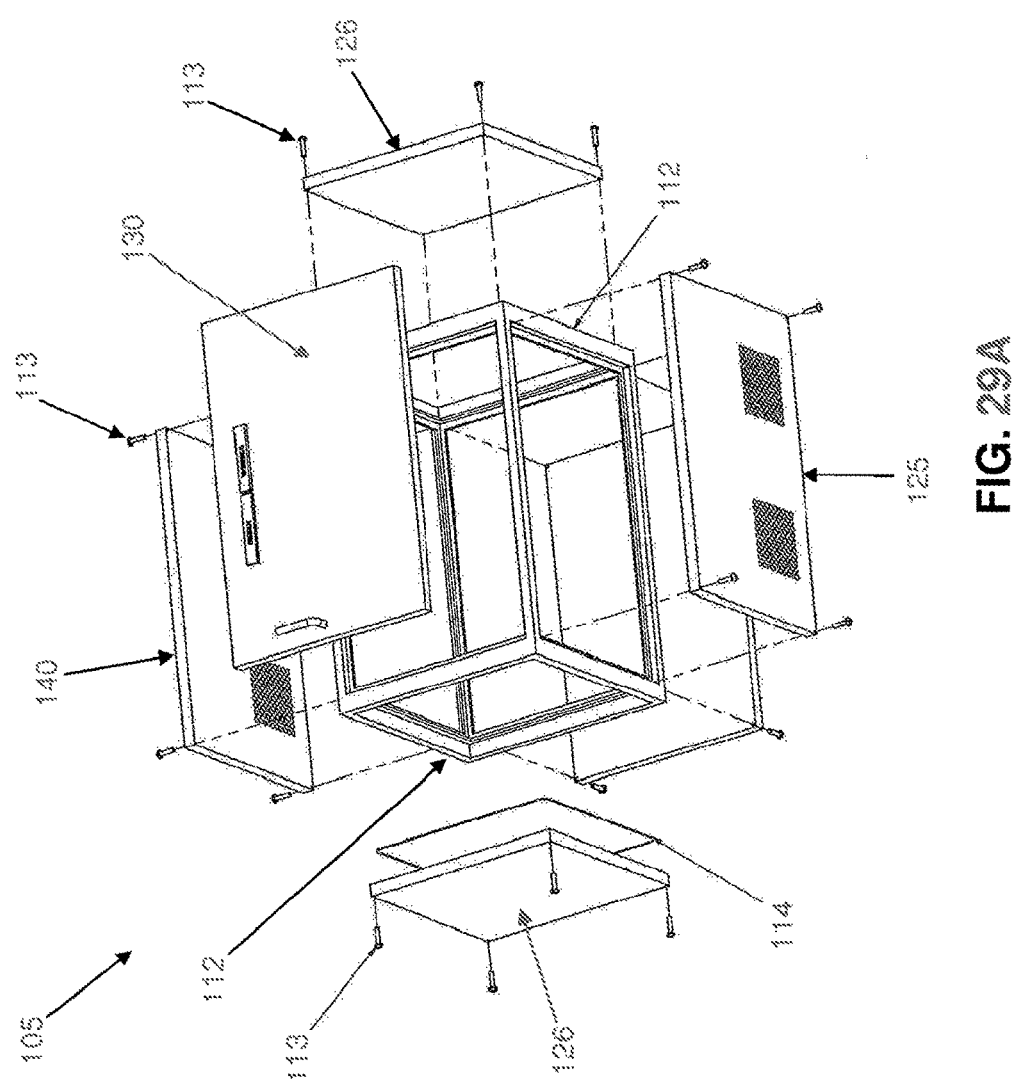

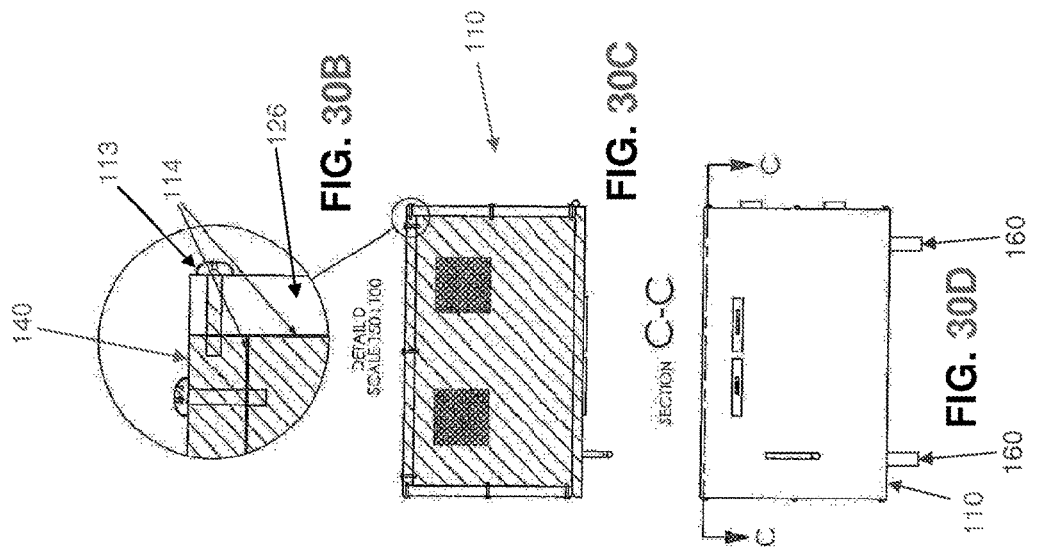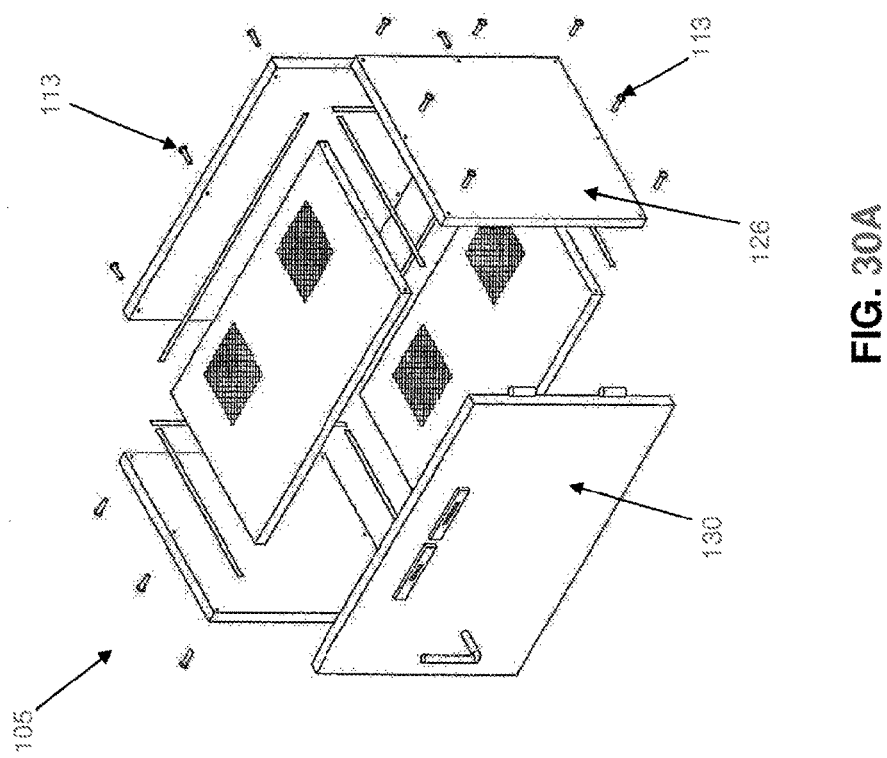

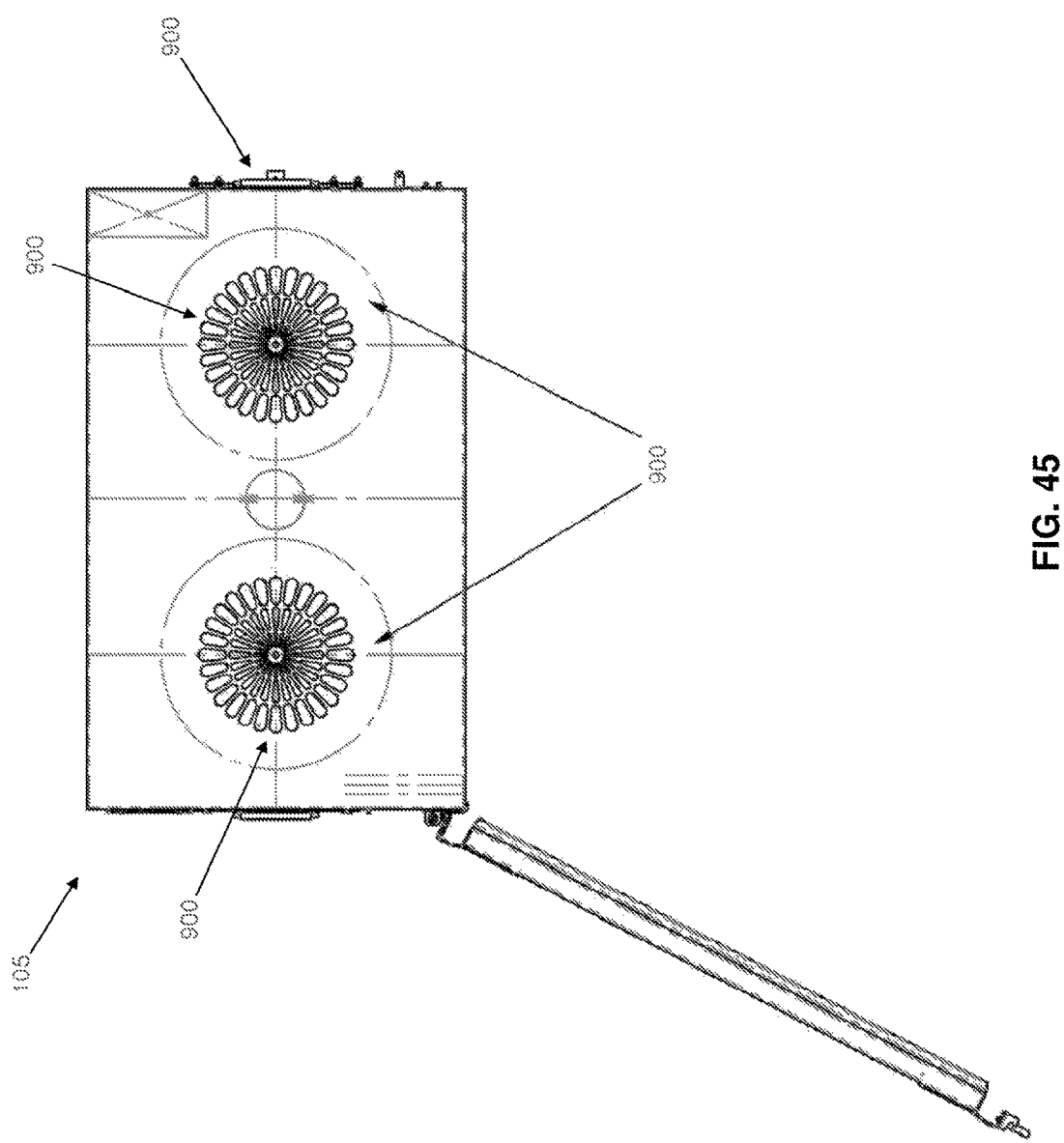

MOBILE STERILIZATION APPARATUS AND METHOD FOR USING THE SAME

CROSS-REFERENCE TO RELATED APPLICATIONS

This application is a continuation of U.S. patent application Ser. No. 15/663,230, filed Jul. 28, 2017, which is related to U.S. patent application Ser. No. 15/369,713 filed on Dec. 5, 2016, which is a continuation of Ser. No. 14/644,094, filed on Mar. 10, 2015, which claims the benefit of U.S. Provisional Application No. 61/950,502, filed on Mar. 10, 2014 and U.S. Provisional Application No. 62/053,338, filed on Sep. 22, 2014, the contents of which are incorporated herein by reference in their entireties.

FIELD OF THE TECHNOLOGY

This invention relates to medical devices and procedures in general, and more particularly to sterilization apparatus and procedures for sterilizing medical instruments and/or devices and maintaining sterility until their intended use.

BACKGROUND

Many medical procedures require the use of sterile instruments and/or devices to perform the medical procedure. Providing sterile instruments and/or devices for these medical procedures is currently a time-consuming and expensive undertaking that requires, among other things, many man-hours, specialized equipment, etc.

In the past, hospitals (and/or other surgical facilities, e.g., surgicenters, etc.) have used an instrument tray sterilization system, in which trays containing the required instruments and/or devices for a given procedure are wrapped with a specially manufactured disposable wrap. The wrapped trays are then autoclaved and processed to the manufacturers' recommendations. The trays are then removed from the autoclave, allowed to cool, and then stored until the contents are needed for a procedure. Prior to the use of the instruments and/or devices, additional man-hours are expended to inspect the wraps so as to ensure that there is no damage that might lead to the contents being deemed non-sterile.

In part to address some of the shortcomings discussed above, mobile sterilization cabinets have been introduced. FIGS. 1-3 show an exemplary prior art mobile sterilization cabinet 5. Sterilization cabinet 5 typically comprises a rectangular-shaped interior chamber 10 (FIG. 2) surrounded by a cabinet bottom 25, cabinet side walls 26, a cabinet back wall 27 and a cabinet top 40. Cabinet 5 may further comprise one or more doors 30 to selectively open up or close off interior chamber 10 of cabinet 5. See, for example, FIG. 2 which shows a cabinet 5 with one door 30 in the open position, and FIG. 3 which shows cabinet 5 with two doors 30 in the closed position. Cabinet 5 may further comprise a gasket (not shown) at the interface of the door(s) and frame of cabinet 5 for sealing cabinet 5 when the door(s) is (are) closed.

Interior chamber 10 of cabinet 5 is preferably also equipped with shelves 45 for supporting surgical trays within chamber 10.

Furthermore, cabinet 5 comprises one or more vents 35 formed in the cabinet top 40 and/or cabinet bottom 25. Vent 35 is covered by a filter 50, and a filter cover 55 holds filter 50 in place against vent 35.

In order to move cabinet 5 into an autoclave or into an operating room or storage room, cabinet 5 comprises wheels 20 mounted directly to cabinet bottom 25. In use, medical instruments and/or instrument trays are positioned on shelves 45, and the shelves are loaded into interior chamber 10 of cabinet 5. Alternatively, shelves 45 may be loaded into cabinet 5 and then the medical instruments and/or instrument trays positioned on shelves 45. Then the entire cabinet 5 is wheeled into an autoclave which is subsequently activated. The hot air and steam generated by the autoclave is able to penetrate into interior chamber 10 of cabinet 5 by way of vents 35, thereby sterilizing cabinet 5 and its contents. At the end of the autoclaving cycle, cabinet 5 is removed from the autoclave, allowed to cool, and then moved to a storage space or directly to an operating room or other space for use in connection with a medical procedure. Sterilized cabinet 5 is kept closed until such time that its contents are required for a medical procedure. So long as cabinet 5 is kept closed, the contents will remain sterile, inasmuch as filters 50 prevent the passage of contaminants through vents 35 into the interior of the cabinet.

While the introduction of mobile sterilization cabinets has allowed for significant savings and efficiencies in hospital sterilization procedures, several shortcomings remain. For example, existing prior art cabinets can be difficult to maneuver into and out of an autoclave and can be difficult to maneuver around a hospital (e.g., to a storage area or an operating room).

Further, existing cabinets 5 can be difficult to store in increasingly crowded hospitals where space is frequently at a premium. In addition, opening existing cabinets at the desired time can significantly expand the footprint of the existing cabinets, inasmuch as space must be allocated to accommodate the swing radius of the door(s).

In addition, existing cabinets can sometimes retain water in the bottom of the cabinet at the end of the autoclave cycle. This is undesirable for several reasons, one of which is that the water can serve as a conduit through which contaminants can be "pulled" (e.g., by a wicking action, through a filter 50 in cabinet bottom 25 and into interior chamber 10).

It can also be difficult for medical personnel to visually assess the current status of existing cabinets or their contents. For example, it is difficult for personnel to know whether an existing cabinet that has been autoclaved is still too hot to handle or whether it has cooled to the point where it may be safely handled. Similarly, it can be difficult for personnel to visually ascertain or verify the status and/or inventory of the contents inside of an existing cabinet without having to open the cabinet and thereby violate the sterile field.

Additional shortcomings of existing cabinets include cumbersome interior shelving, an inability to sufficiently isolate smaller areas within the cabinet, difficulty in accessing and changing filters, etc.

Still other deficiencies of existing cabinets are known to those skilled in the art.

Thus there is a need for a new and improved mobile sterilization apparatus and method for sterilizing medical instruments and devices, storing the sterilized medical instruments and devices in a sterile condition until use, and then delivering the sterilized medical instruments and devices to a location where a medical procedure will be performed, that does not suffer from one or more of the disadvantages associated with the prior art.

SUMMARY

The present invention provides new and improved methods for confirming the integrity of one or more seals on a mobile sterilization apparatus and devices for confirming the integrity. These methods and devices allow for sterilizing medical instruments and devices, for storing the sterilized medical instruments and devices in a sterile condition until use, and then delivering the sterilized medical instruments and devices to a location where a medical procedure will be performed.

In one example, the present disclosure includes a method for confirming integrity of a sterilization container. For example, such a method includes closing a sterilization container having at least one vented area that allows fluids to pass into and out of the sterilization container where the at least one vented area is located in a panel of a wall or a door of the sterilization container; positioning a first filter to fully cover the at least one vented area and such that the first filter extends beyond a perimeter of the at least one vented area; engaging a portion of the first filter to the panel of the sterilization unit at an area beyond the perimeter of the at least one vented area; positioning a second filter over the first filter such that the second filter covers the at least one vented area; affixing an edge of a filter cover against the sterilization unit to engage the second filter directly against the first filter and the first filter against the panel such that the edge forms a seal simultaneously with both the first filter and the second filter against the sterilization unit (in alternate variations the seal is formed sequentially rather than simultaneously); initiating a sterilization cycle on the sterilization unit to sterilize an internal region of the sterilization unit; loosening the filter cover from the sterilization unit to disengage the seal of the edge from both the first filter and the second filter against the sterilization cabinet; detaching the second filter from both the first filter and the sterilization unit, where the first filter remains engaged to the panel; and examining the second filter to assess an integrity of the first filter without removing the first filter from the sterilization unit. Clearly, the user can examine the integrity of both filters as well. Variations of the container include the vented area in a top/roof, bottom, or side of the container. In an additional variation, a user of the container can simply loosen the filter cover from the second filter only to check the second filter first, leaving the first filter and first filter cover intact.

Another variation of the method includes securing the first filter between the panel of the sterilization unit and a frame plate, where the frame plate is secured to the panel. Variations include a frame plate that is detachably secured to the panel, a frame plate is moveable secured to the panel, and a hinge or other structure securing the frame plate to the panel.

The frame plate described herein can include any geometric outer profile shape as long as the frame plate allows passage of a fluid therethrough. In one example, the frame plate comprises a ring shape. In addition, the frame plate can comprise any material used in sterilization devices, including but not limited to a material selected from the group consisting of a metal, a polymer, a composite material. The frame plate can be disposable or reusable.

Variations of the methods and devices described herein include the edge of the filter cover positioned within a perimeter of the frame plate.

As noted herein, closing the sterilization container can include loading at least one surgical tray containing a surgical instrument into the interior sterilization container prior to closing the sterilization container.

Again, the methods and devices described herein allow relocation of the sterilization cabinet to a sterile location after examining the second filter to assess the integrity of the first filter without removing the first filter from the sterilization unit.

Another variation of a method for sterilizing a medical item comprises securing a sterilization container with the medical item therein wherein the sterilization container includes at least one vented area in a panel of a wall or a door allowing fluids to pass into and out of the sterilization container; positioning a first filter to cover the at least one vented area and extend beyond a perimeter of the at least one vented area; engaging a portion of the first filter to the panel of the sterilization container at an area beyond the perimeter of the at least one vented area; positioning a second filter over the first filter such that the second filter covers the at least one vented area; affixing an edge of a filter cover against the sterilization container to engage the second filter directly against the first filter and the first filter against the panel such that the edge forms a seal with the first filter and the second filter against the sterilization container; initiating a sterilization cycle on the sterilization container to sterilize the medical item; loosening the filter cover from the sterilization container to break the seal of the edge, the first filter, and the second filter against the sterilization container; detaching the second filter from both the first filter and the sterilization container, where the first filter remains engaged to the panel; and examining the second filter to assess an integrity of the second filter once detached.

Another variation of a method for preparing a medical item for sterilization includes securing a sterilization container with the medical item therein wherein the sterilization cabinet includes at least one vented area in a panel of a wall or a door allowing fluids to pass into and out of the sterilization cabinet; positioning a first filter to cover the at least one vented area and extend beyond a perimeter of the at least one vented area; engaging a retainer member against the first filter to maintain the first filter to the panel of the sterilization cabinet at an area beyond the perimeter of the at least one vented area; positioning a second filter over the first filter and the retainer member such that the second filter covers the at least one vented area; and affixing an edge of a filter cover against the sterilization cabinet independently of the retainer member to engage the second filter directly against the first filter and the first filter against the panel such that the edge forms a seal with the first filter and the second filter against the sterilization cabinet.

The present disclosure also includes a sterilization cabinet for sterilizing a medical item. For example such a sterilization cabinet can include a sterilization chamber surrounded by a plurality of panels, where at a first panel of the plurality of panels is removable from the plurality of panels to permit placement of the medical item into the sterilization chamber, and where the first panel is securable to at least one of the plurality of panels to enclose the sterilization chamber; where at least one of the plurality of panels comprises a vented panel having a vented area, where the vented area allows fluids to pass into and out of the sterilization chamber; a filter retaining structure that is configured to removably engage a first filter to the vented panel beyond a perimeter of the vented area; a filter cover having an edge, where the filter cover is securable to the sterilization cabinet to engage the first filter and at least a second filter against the directly against the vented panel such that the edge forms a seal with the first filter and the second filter against the sterilization cabinet; and wherein after a sterilization cycle the edge of the filter cover is disengageable from the vented panel to break seal of the of the first filter and the second filter, allowing for removal of the second filter from both the first filter and the sterilization cabinet and where the filter retaining structure maintains engagement of the first filter remains to the vented panel.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 4-6, 7A-7D and 8A-8D are schematic views showing a novel mobile sterilization system comprising a novel sterilization cabinet and a novel transfer cart;

FIG. 28 is a schematic view showing a mobile sterilization system comprising external shelving;

FIGS. 29A-D and 30A-D are exploded schematic views of a novel sterilization cabinet formed in accordance with the present invention;

FIGS. 42-45 are schematic views of the improved drain and filter assembly of FIGS. 31-41.

DETAILED DESCRIPTION

The present invention provides a new and improved mobile sterilization apparatus and method for sterilizing medical instruments and devices, for storing the sterilized medical instruments and devices in a sterile condition until use, and then delivering the sterilized medical instruments and devices to a location where a medical procedure will be performed.

Figure 1:
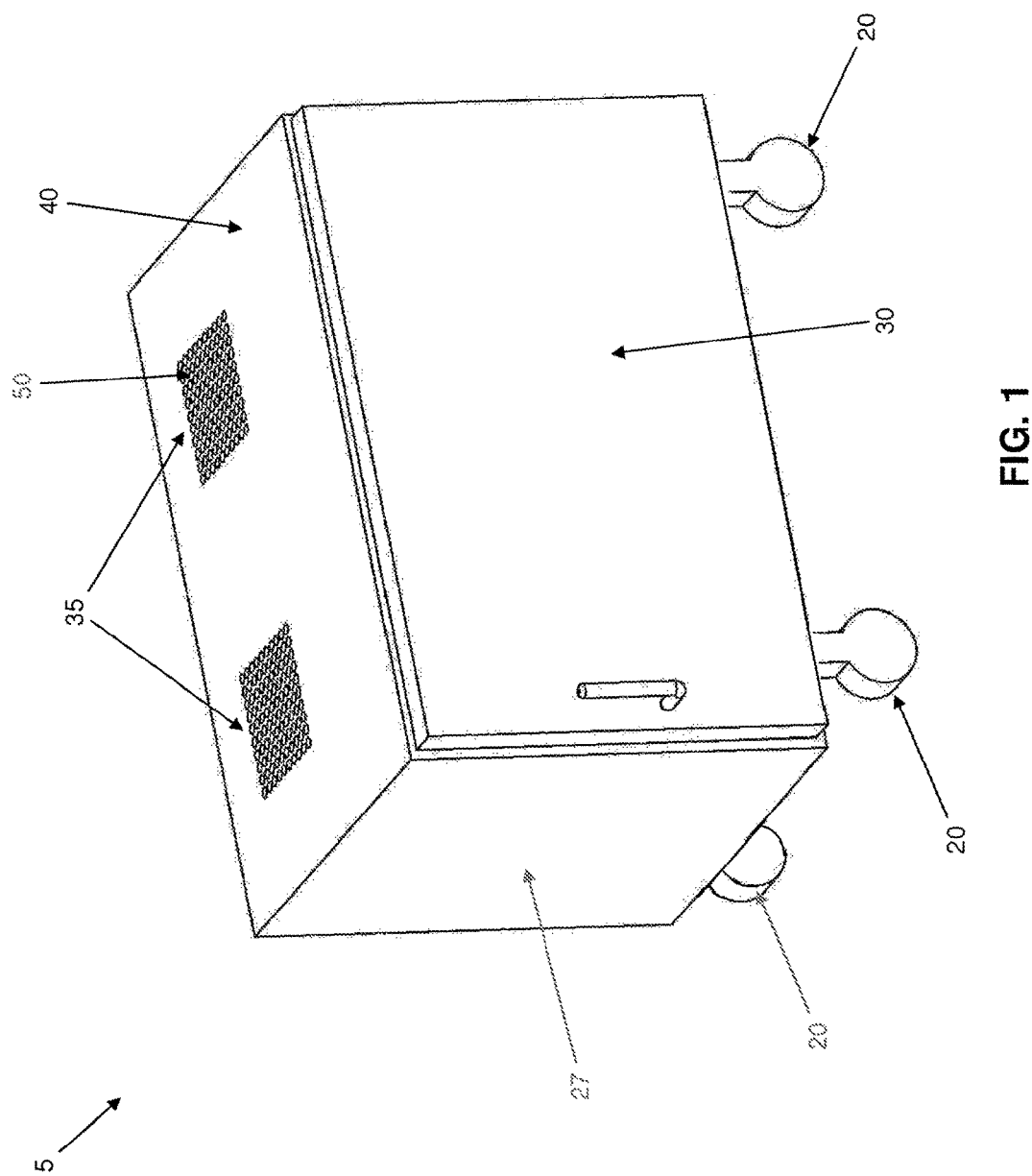
FIGS. 1-3 are schematic views showing a prior art mobile sterilization cabinet.
Figure 2:
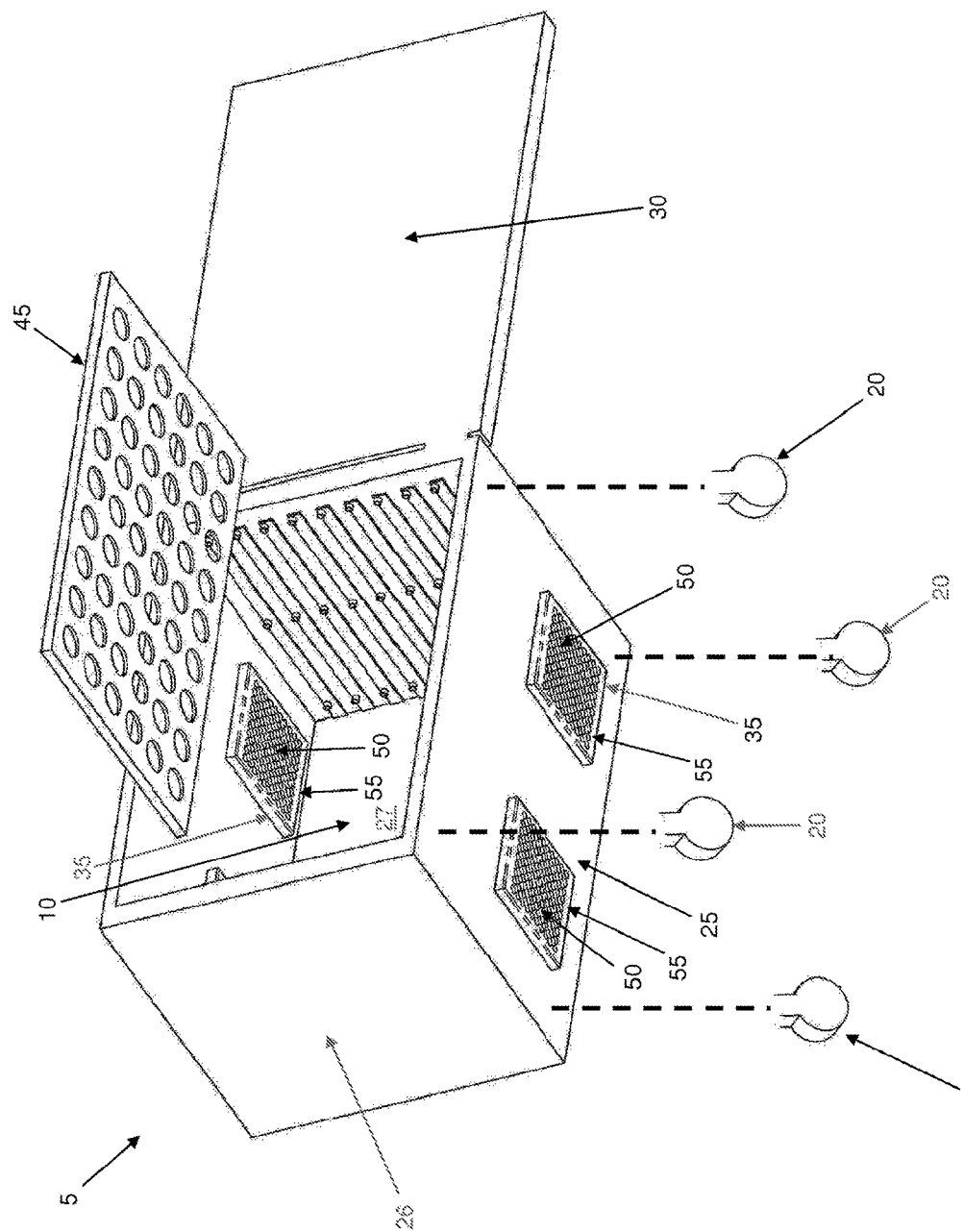
Figure 3:
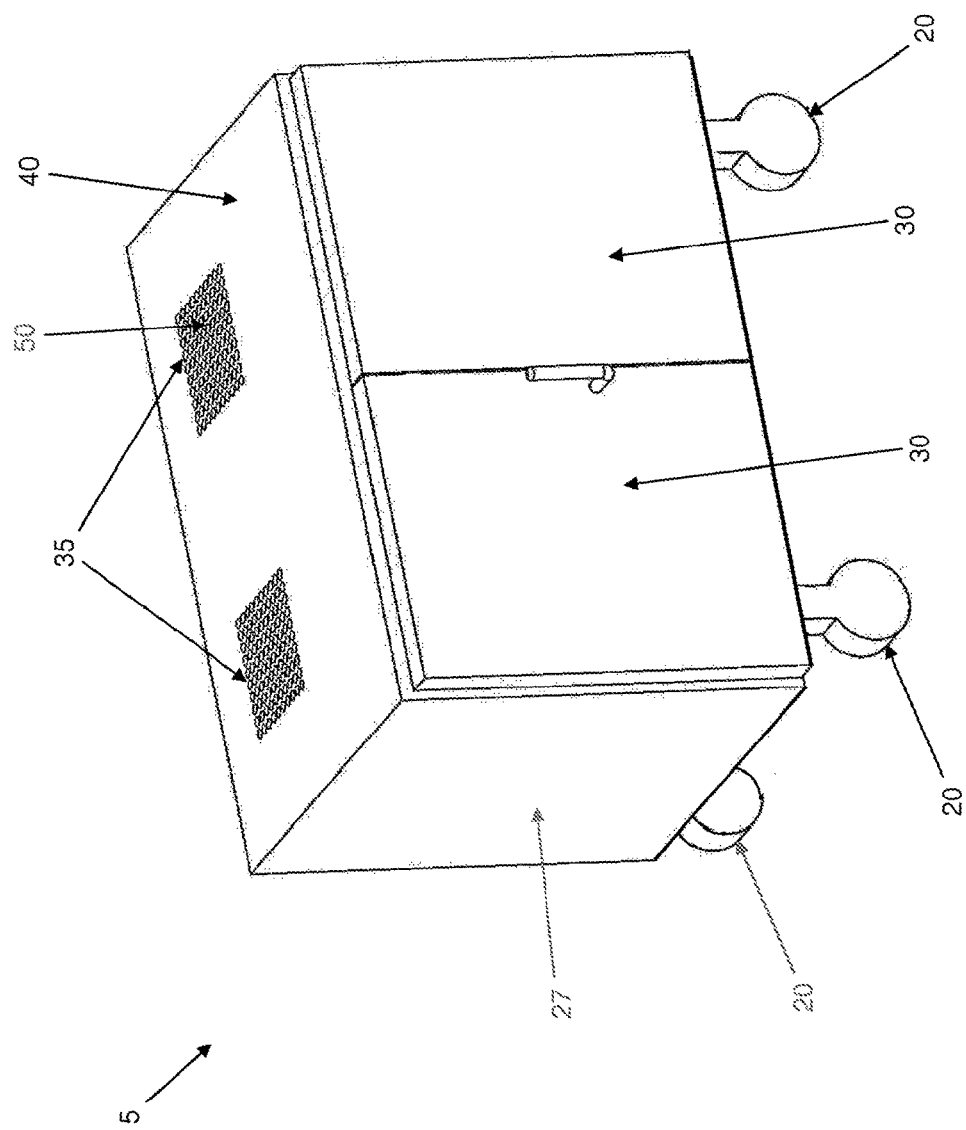
Figure 4:
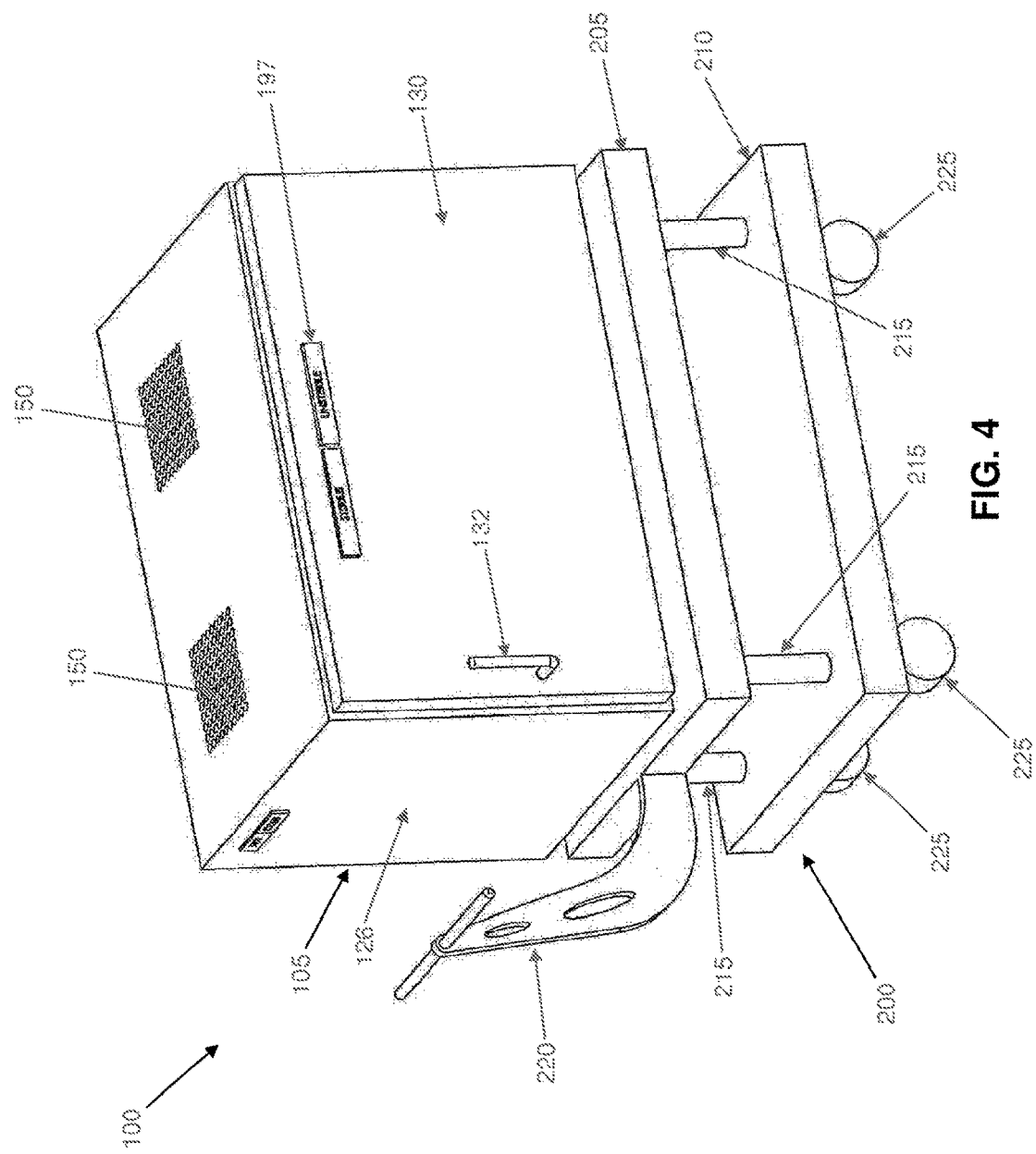

Looking now at FIG. 4, there is shown a novel mobile sterilization system 100 comprising a novel sterilization cabinet 105 and a novel transfer cart 200.

Sterilization cabinet 105 typically comprises a rectangular-shaped interior chamber 110 (FIG. 13) surrounded by a cabinet bottom 125, cabinet side walls 126, a cabinet back wall 127 and a cabinet top 140. Cabinet 105 may further comprise one or more doors 130 to selectively open up or close off interior chamber 110 novel mobile sterilization system 100 of cabinet 105. Cabinet 105 may further comprise a gasket (not shown) at the interface of the door(s) and frame of cabinet 105 for sealing cabinet 105 when the door(s) are closed.

Interior chamber 110 of cabinet 105 is preferably also equipped with shelves 145 (FIG. 23) for supporting surgical trays or instruments, etc. within chamber 110.

Furthermore, cabinet 105 comprises one or more vents 135 formed in at least one of the cabinet side walls 126, cabinet back wall 127, the cabinet top 140 and cabinet bottom 125. Vent 135 is covered by a filter 150, and a filter cover 155 (FIG. 23) holds filter 150 in place over vent 135. Further details of sterilization cabinet 105 (e.g., improvements to doors 130, filters 150, shelves 145, etc.) will be discussed in further detail below.

In order to move sterilization cabinet 105 along a surface (e.g., along a floor, along transfer cart 200, etc.), sterilization cabinet 105 comprises a plurality of casters or wheels 160 (generally shown in the figures in schematic form). In one preferred form of the invention, casters or wheels 160 are mounted to cabinet bottom 125, e.g., via a wheel or caster bracket (see below) of the sort well known in the art. Note that casters or wheels 160 are not visible in a number of the figures due to the angle of view of those figures, however, wheels or casters 160 can be clearly seen in FIGS. 7C, 13, 22A, 22B, 23, 24, 25A, 27, 29D, 30D, 36, 37, 39, 41, 43 and 44.

While sterilization cabinet 105 can be moved along a floor via its casters or wheels 160, in many situations it can be desirable to move sterilization cabinet 105 on transfer cart 200, e.g., into an autoclave or into an operating room or storage room.

More particularly, transfer cart 200 provides a platform upon which sterilization cabinet 105 may be positioned for transport between locations. By way of example but not limitation, transfer cart 200 may be used to move sterilization cabinet 105 from one part of a facility to another (e.g., a sterile processing department or an autoclave to an operating room). In addition, and again by way of example but not limitation, transfer cart 200 may be used to transfer sterilization cabinet 105 into and out of storage, and/or to move sterilization cabinet 105 into and out of an autoclave, and/or to move sterilization cabinet 105 between facilities or hospital rooms.

Transfer cart 200 generally comprises an upper platform 205 (FIG. 4) for receiving sterilization cabinet 105, a lower platform 210 to which a mechanism (e.g., wheels) for moving the transfer cart between locations is mounted. Vertical risers 215 extend between upper platform 205 and lower platform 210. Transfer cart 200 preferably also comprises a handle 220 for maneuvering transfer cart 200 between locations.

Figure 5:
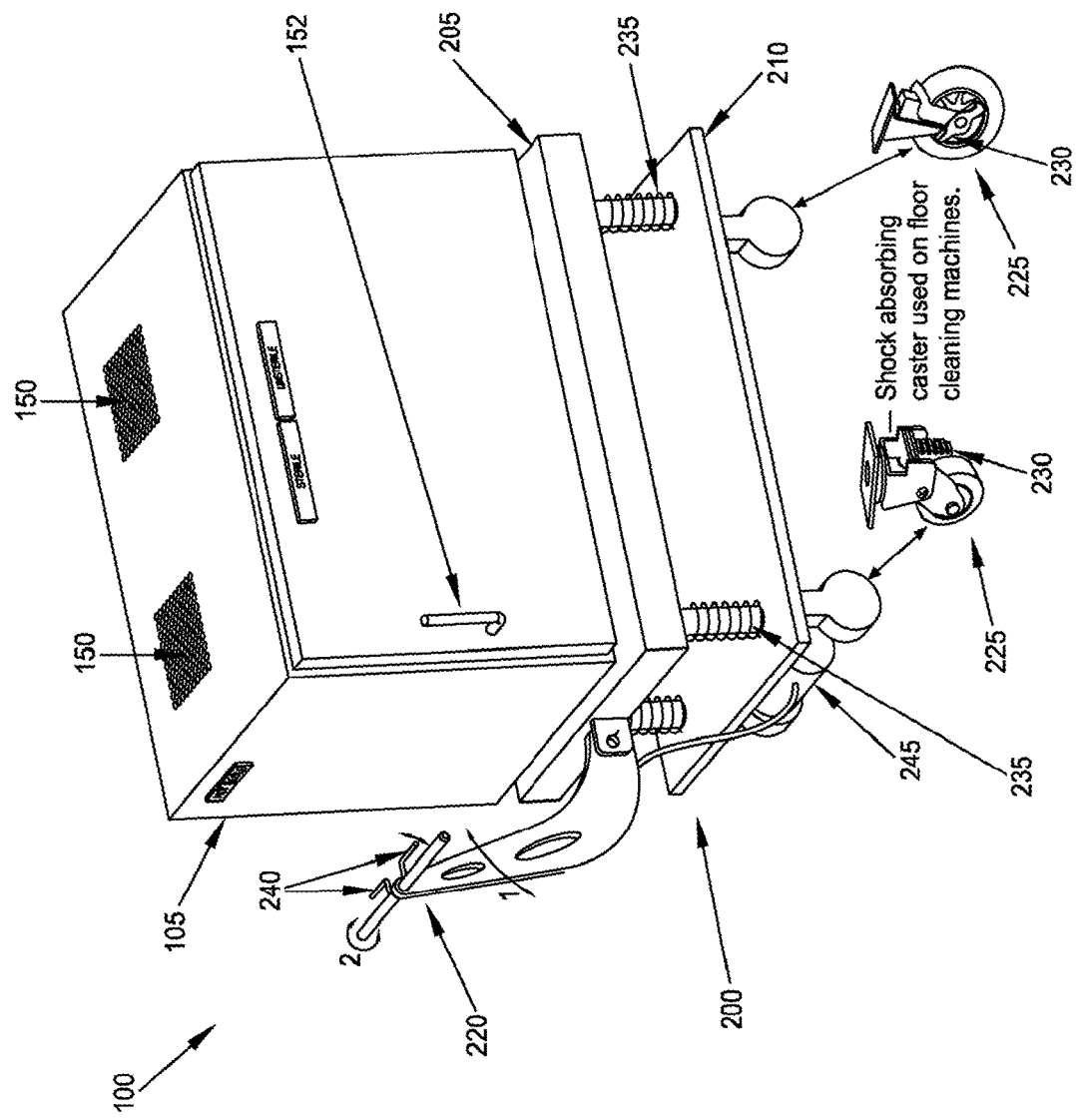

Looking now at FIGS. 4 and 5, transfer cart 200 comprises swiveling casters 225 for moving transfer cart 200 between locations. Casters 225 may be adjusted between a swiveling condition and a non-swiveling condition by way of easily-accessed, foot-operated pedal adjustment(s) on casters 225, or by way of adjustments performed from a handle 220. In other words, a user is able to adjust casters 225 from a first configuration wherein the casters are swiveable and a second configuration wherein the casters 225 are locked against swiveling. This feature allows a user to exercise additional control over transfer cart 200 when it is being moved between locations. Casters 225 can also be anti-static as an added safety feature.

Preferably, transfer cart 200 may be provided with a compliant shock-absorbing suspension system that enables a smoother "ride" over varying terrain and inclines as well as during shipping with, and without, instrument trays (loaded with medical instrumentation or other contents) being positioned in sterilization cabinet 105.

By way of example but not limitation, mobile sterilization system 100 may be transported fully loaded by remotely-located sterile processing companies to and from medical or other facilities that are sometimes hundreds of miles away from a remotely-located sterile processing facility. The shock-absorbing suspension system allows for improved safety and security of the loaded medical instrument trays to limit possible damage and/or displacement caused during transportation.

As shown in FIG. 5, a shock-absorbing suspension system may comprise shock-absorbing suspension springs 230 positioned on casters 225 and/or resilient springs 235 mounted between upper platform 205 and lower platform 210 in place of vertical risers 215.

Alternatively, vertical risers 215 may be formed in a telescopic configuration and resilient springs 235 may be disposed around and/or inside telescopic vertical risers 215. Resilient springs 235 are set so as to bias upper platform 205 and lower platform 210 away from one another, so as to provide shock absorption functionality for upper platform 205 (and sterilization cabinet 105) when casters 225 encounter a bump or some other surface abnormality that would cause a shock to transfer cart 200. Additional shock-absorbing springs 230 or resilient springs 235 may be mounted to any other load-bearing parts of transfer cart 200 so as to provide shock absorption during transportation of mobile sterilization system 100.

Transfer cart 200 may also comprise a "dead man's" safety grip and/or auto-braking system. More particularly, and still looking at FIG. 5, there is shown a dead man's safety grip 240. Dead man's safety grip 240 is connected (either electronically, mechanically or otherwise) to one or more wheel brakes capable of preventing casters (or other wheels) from moving (not shown). In one form of the invention, the wheel brakes are configured so that their default position is with the brakes applied to casters 225 of transfer cart 200, thereby prohibiting movement of transfer cart 200. When dead man's safety grip 240 is actuated by a user, the wheel brakes are moved to a second configuration, whereby to allow the wheels to roll freely. Accordingly, the wheels (and, by extension, the transfer cart) are prevented from rolling unless dead man's safety grip 240 is actuated. This feature provides foolproof braking during loading and unloading of sterilization cabinet 105 onto transfer cart 200, and during loading and unloading of the contents of sterilization cabinet 105.

Transfer cart 200 may also comprise a power assist mechanism 245 (FIG. 4) which can be built into, or otherwise attached to, transfer cart 200. As shown in FIG. 5, power assist mechanism 245 may comprise a motor configured to drive casters 225 when a motor/servo power assist handle or other control (not shown) is actuated by a user (e.g., by turning the handle, in the manner of a motorcycle throttle grip). Power assist mechanism 245 may assist in the transportation of heavier loads for longer distances, on inclines and/or over uneven surfaces. Power assist mechanism 245 may drive the wheels either forward or in reverse.

Figure 6:
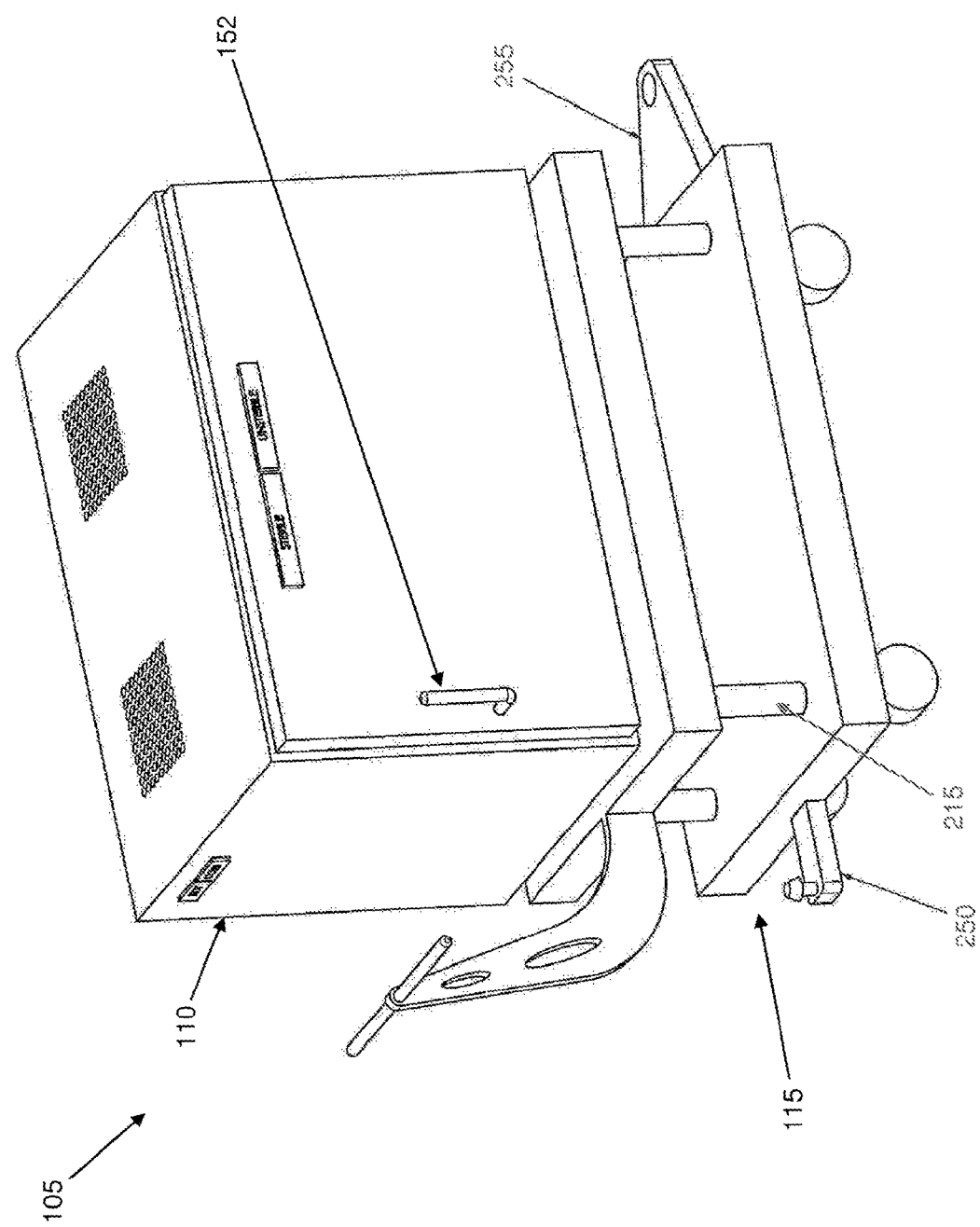

In one embodiment, and looking now at FIG. 6, transfer cart 200 may be provided with a mechanism for linking the transfer cart to one or more other transfer carts 200 so that the transfer cart may be used to tow (or push) another transfer cart during transport between locations. To effectuate such linking capability, transfer cart 200 may be provided with a male component 250 at one end of lower platform 210 of transfer cart 200 and a female component 255 disposed at the opposite end of lower platform 210 of transfer cart 200, whereby to allow the male or female component of a given cart to be linked with the complementary male or female component on another cart. One or both of male component 250 and female component 255 can be retracted or folded under transfer cart 200 when the transfer cart or tugging/linking feature is not in use.

In one embodiment, transfer cart 200 may also be configured with bumpers and/or rollers 260 (FIG. 7A) to protect transfer cart 200 and/or other objects, and to otherwise facilitate movement of transfer cart 200 from one location to another (e.g., during transportation through a hospital hallway).

Looking now at FIGS. 7A-7D, transfer cart 200 is preferably releasably secured to cabinet 105 by a combination of complimentarily configured tracks or rails and a locking latch or similar device.

Preferably, transfer cart 200 is provided with an improved safety feature of interlocking tracks or rails to catch interlocking caster brackets (which mount to casters or wheels 160 to cabinet 105). More particularly, lips 265 extend inboard from a pair of transfer cart tracks or rails 270, which themselves extend upward from a side or top surface of upper platform 205 of transfer cart 200 (i.e., with one track or rail 270 extending along each side of transfer cart 200). Lips 265 are configured to slidably engage elongated projection 165 of cabinet caster or wheel bracket 170 so as to prevent sterilization cabinet 105 from moving either laterally (i.e., side-to-side), or up-and-down, with respect to transfer cart 200 while cabinet 105 is positioned on transfer cart 200.

Transfer cart 200 and sterilization cabinet 105 are preferably formed so as to provide autolocking features to keep cabinet 105 secured to transfer cart 200. More particularly, and looking now at FIGS. 7A and 7B, transfer cart 200 may be configured with a center locking latch 275 that is mounted to upper platform 205 of transfer cart 200. Center locking latch 275 may be configured to receive a bar 175 which extends across the bottom of sterilization cabinet 105 such that, after bar 175 is received by latch 275, sterilization cabinet 105 is prohibited from moving forward or backward with respect to transfer cart 200.

Transfer cart 200 is preferably configured so as to be "universal" by providing railings and attachments that are adjustable so as to be able to accommodate the dimensions of different sterilization cabinets or other cargo, and/or the dimensions of different destinations of sterilization cabinet 105 (e.g., different autoclaves or storage racks).

More particularly, and looking now at FIGS. 8A-8D, transfer cart 200 may be configured with universal railings 280 which are of adjustable width along directional arrow 1 or 3 shown in FIG. 8A, and a detachable adapter 285 which is also configured to be of adjustable width. Adjustable rails 280 and adapter 285 may be fit together, such as in the male/female configuration shown in FIG. 8B, so as to allow for a smooth surface for the transfer of sterilization cabinet 105 from transfer cart 200 to a destination (e.g., a storage rack, autoclave, etc.). The width of universal rails 210 and adapter 285 is determined at least in part by reference to the width of the corresponding features at the destination (e.g., it may be determined by the width of a storage rack or the relevant components of an autoclave).

Adapter 285 may be configured to extend straight out above upper platform 205 (such as is shown in FIG. 8A), or to fold down (such as is shown in FIGS. 8C and 8D) so as to not protrude at the end of transfer cart 200. Alternatively, adapter 285 may be configured so as to be entirely removable from the transfer cart. Where detachable adapter 285 is configured to be removable from transfer cart 200, adapter 285 may be further configured to be stowed in an unobtrusive location on transfer cart 200, or it may be configured to be stored near a destination location for ready use.

The universal fit feature described above improves production capacity, lowers cost, and enhances the ease and safety of moving mobile sterilization system 100 (e.g., through hospital hallways). When adapter 285 is removed and/or folded away (such as shown in FIGS. 8C and 8D), a blunt-nosed, shorter and less dangerous cart front is presented at the front end of mobile sterilization system 100. As discussed previously, adapter 215 may either stay with each transfer cart 200 as a folding or stowable component or it may be left at a desired destination (e.g., in a sterile processing department to be stored adjacent to the autoclave or next to a storage rack or rack system).

In another embodiment of the present invention, an alternative transfer cart is provided which is capable of being vertically adjusted so as to raise and lower the upper platform of a transfer cart (and, in turn, a sterilization cabinet 105 secured to the upper platform) in order to meet the needs of a user. By way of example, the upper platform of the transfer cart can be lowered for easier visibility during transportation between locations, and then raised to a desired height when the sterilization cabinet is opened at a desired location.

The vertically-adjustable transfer cart may be raised and lowered mechanically (e.g., such with a scissor lift, as will be discussed in further detail below) electronically, hydraulically, pneumatically, by a battery-operated power device, or by some other appropriate means.

Figure 9:
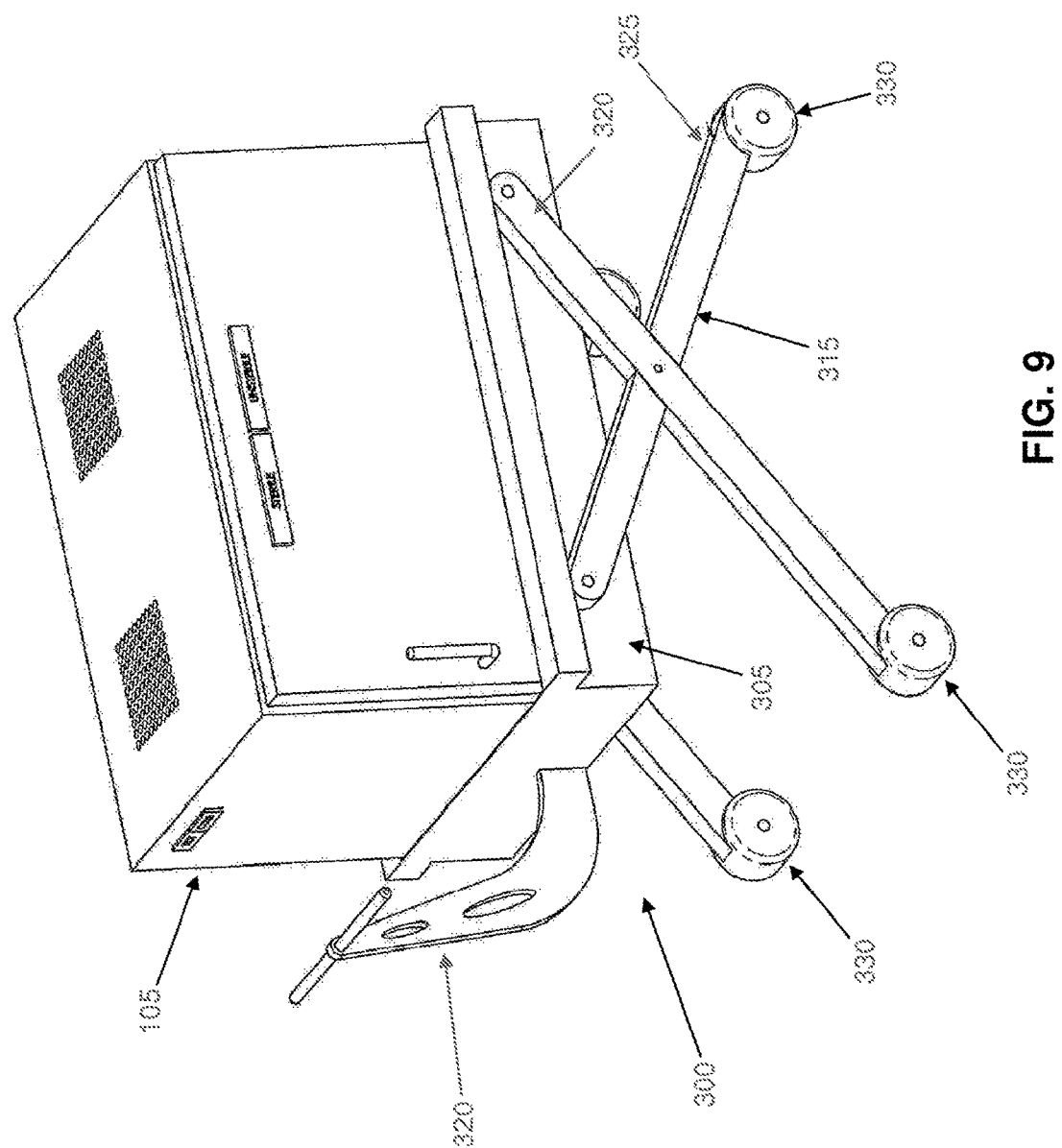
FIG. 9 is a schematic view showing a further embodiment of the novel sterilization cart of the present invention.

To this end, and looking now at FIG. 9, a vertically-adjustable transfer cart 300 is provided.

Vertically-adjustable transfer cart 300 is generally similar to transfer cart 200 discussed above, except that vertical risers 215 and lower platform 210 are replaced by a scissor lift 315 having an upper end 320 and a lower end 325.

Sterilization cabinet 105 is configured to be secured to upper platform 305 of transfer cart 300 in the same manner discussed above. Scissor lift 315 is connected to upper platform 305 at its upper end 320 and to wheels 330 at its lower end 325 for moving the transfer cart between locations.

In accordance with this aspect of the invention, scissor lift 315 may be actuated so as to enable upper platform 305 to be lowered until it is substantially flush with the floor.

Figure 10:
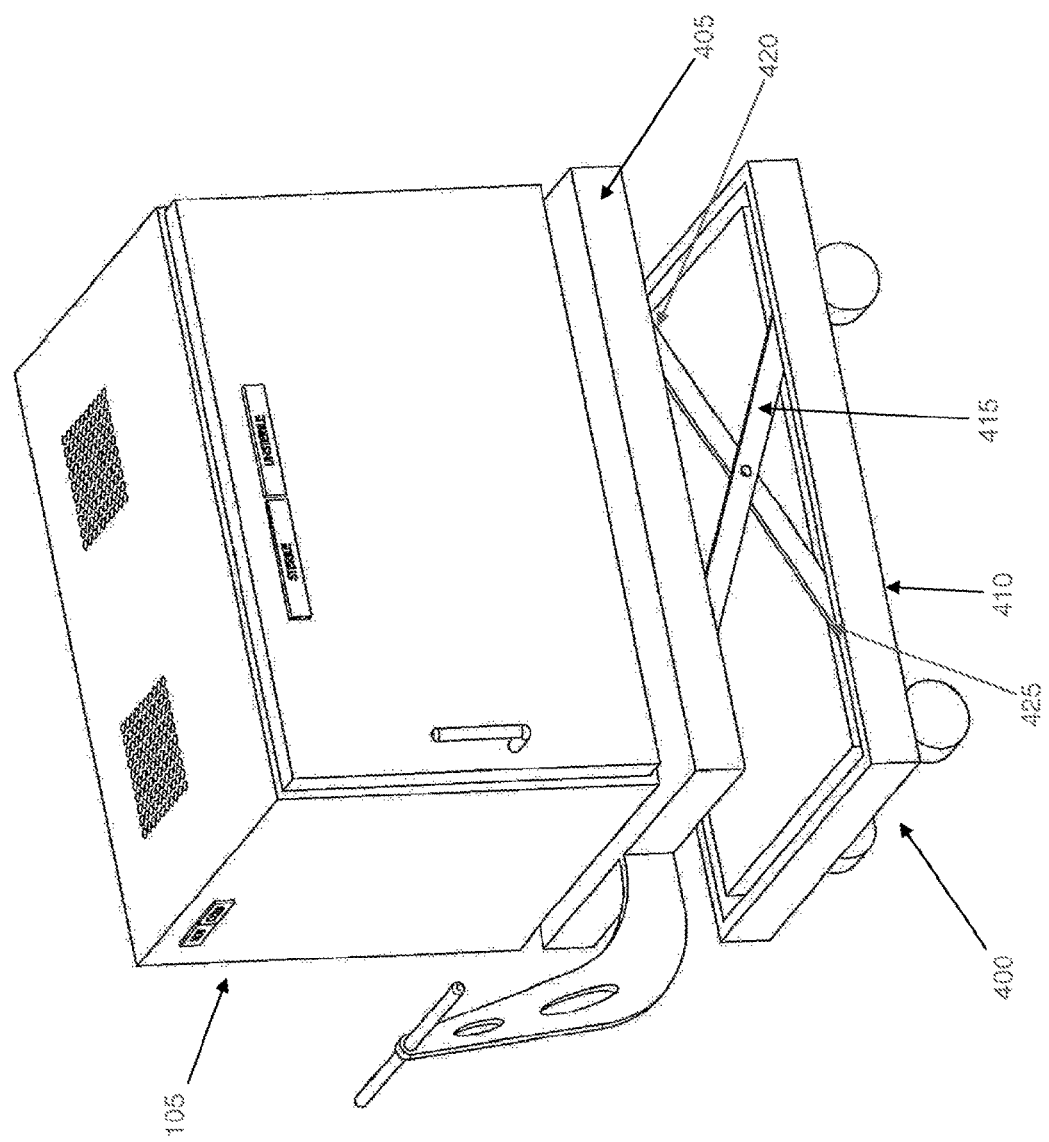
FIG. 10 is a schematic view showing another embodiment of the novel sterilization cart of the present invention.

In another embodiment of the present invention, and looking now at FIG. 10, a vertically-adjustable transfer cart 400 is provided. Transfer cart 400 is generally similar to transfer cart 200 discussed above, except that vertical risers 215 are replaced by a scissor lift 415 having an upper end 420 and a lower end 425.

More particularly, transfer cart 400 comprises an upper platform 405 which is configured to be secured to sterilization cabinet 105 as discussed above, a lower platform 410 and a scissor lift 415 extending between upper platform 405 and lower platform 410.

Actuation of scissor lift 415 in this embodiment will move upper platform 405 up and down, as described above, however, upper platform 405 is not lowered all the way to ground level (i.e., it is lowered to the level of lower platform 410). This embodiment can provide additional stability for transfer cart 400.

Scissor lifts 315 and 415 of transfer carts 300 and 400, respectively, may be actuated (i.e., raised and lowered) by a lift mechanism that can be a mechanical hand-crank or hydraulic or pneumatic hand-pump, or which may be power-assisted (mechanical, hydraulic, pneumatic, etc.) via electric or battery operation.

In addition, transfer carts 300 and 400 may comprise an electronic control system (such as that shown in FIG. 11 and discussed in more detail below) which may allow a user to pre-program specific heights into the electronic control system, which will direct the transfer cart to assume a desired height (e.g., for loading the sterilization cabinet into a particular autoclave, or a preferred height for operating room or sterile processing department staff who will unload, load or transport the sterilization cabinet). This feature allows for height adjustments, thereby providing ergonomic benefits without compromising the sterile field on account of the nurse or scrub technician's physical stature.

An additional benefit of the height adjustment feature described above is that the sterilization cabinet can be lowered to allow for better line of sight over the top of the cabinet during transportation and to provide a lower center of gravity so as to reduce the possibility of tipping. The pre-programmed heights may be set by the user as discussed above.

Figure 11:
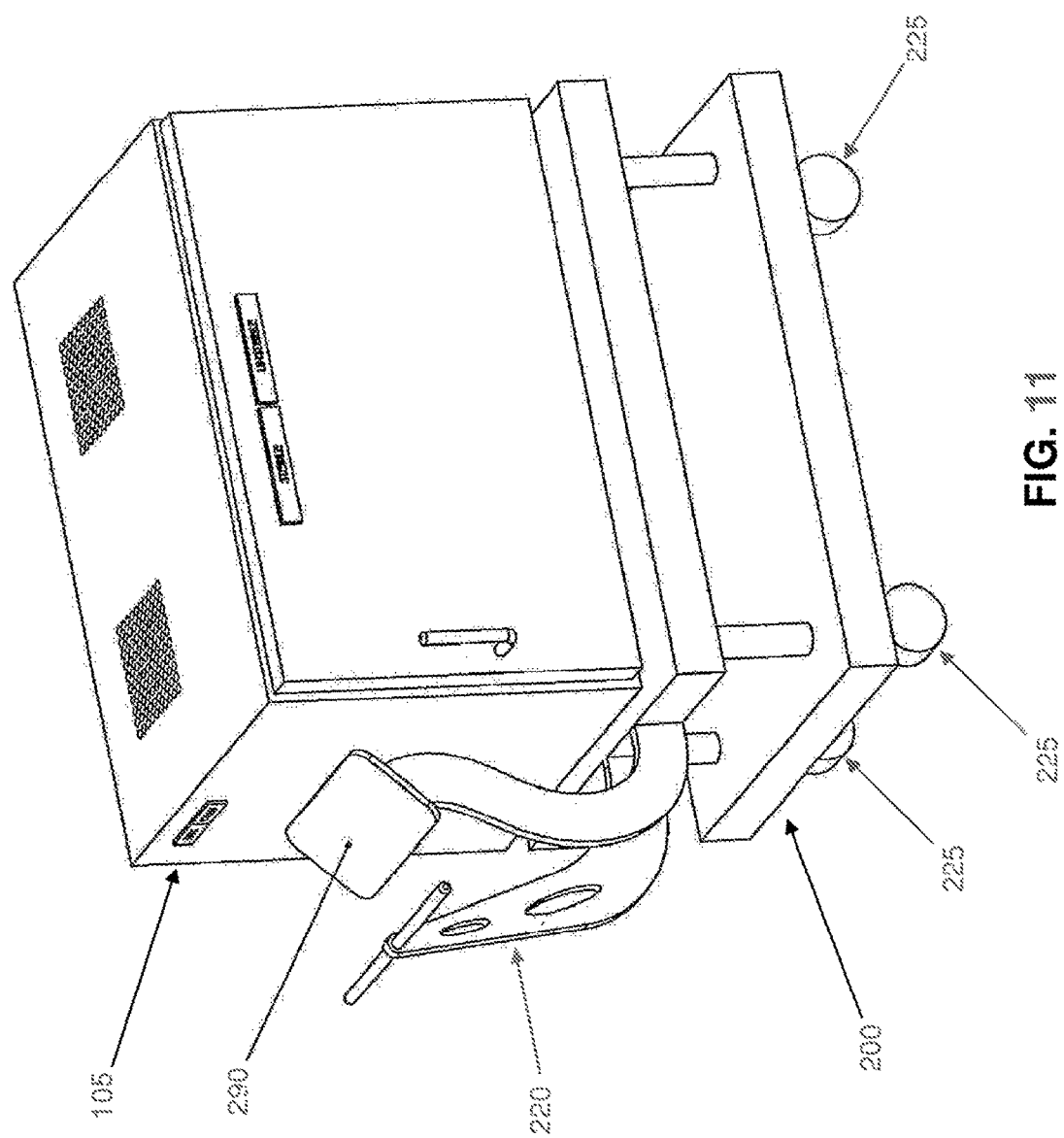
FIG. 11 is a schematic view showing an electronic control system of the mobile sterilization system of the present invention.

Looking now at FIG. 11, the transfer cart of the present invention (e. g., transfer carts 200, 300 and 400) may also be provided with an electronic control system 290 for tracking and/or identifying the transfer cart and the contents of sterilization cabinet 105.

More particularly, electronic control system 290 of the transfer cart of the present invention preferably has the ability to be electronically traced with a LOJACK®-like device, or a similar tracing-type system. In other words, the location of the transfer cart (e.g., building, floor, room) may be remotely monitored by use of a global positioning system (GPS), radio-frequency identification (RFID), or other location-tracking device.

In addition, electronic control system 290 may use RFID, or other identification technology, to identify a particular sterilization cabinet 105, the contents of that sterilization cabinet 105 (e.g., trays or instruments), its location, current temperature, and/or sterilization status (e.g., pre- or post-sterilization, sterile or non-sterile, etc.). Electronic control system 290 may also provide additional information such as date, operator, cycles, cycle type, and contents inside sterilization cabinet 105, among other things.

The information provided by electronic control system 290 may be displayed on a screen to a user, or audibly delivered through a speaker to a user.

Figure 12:
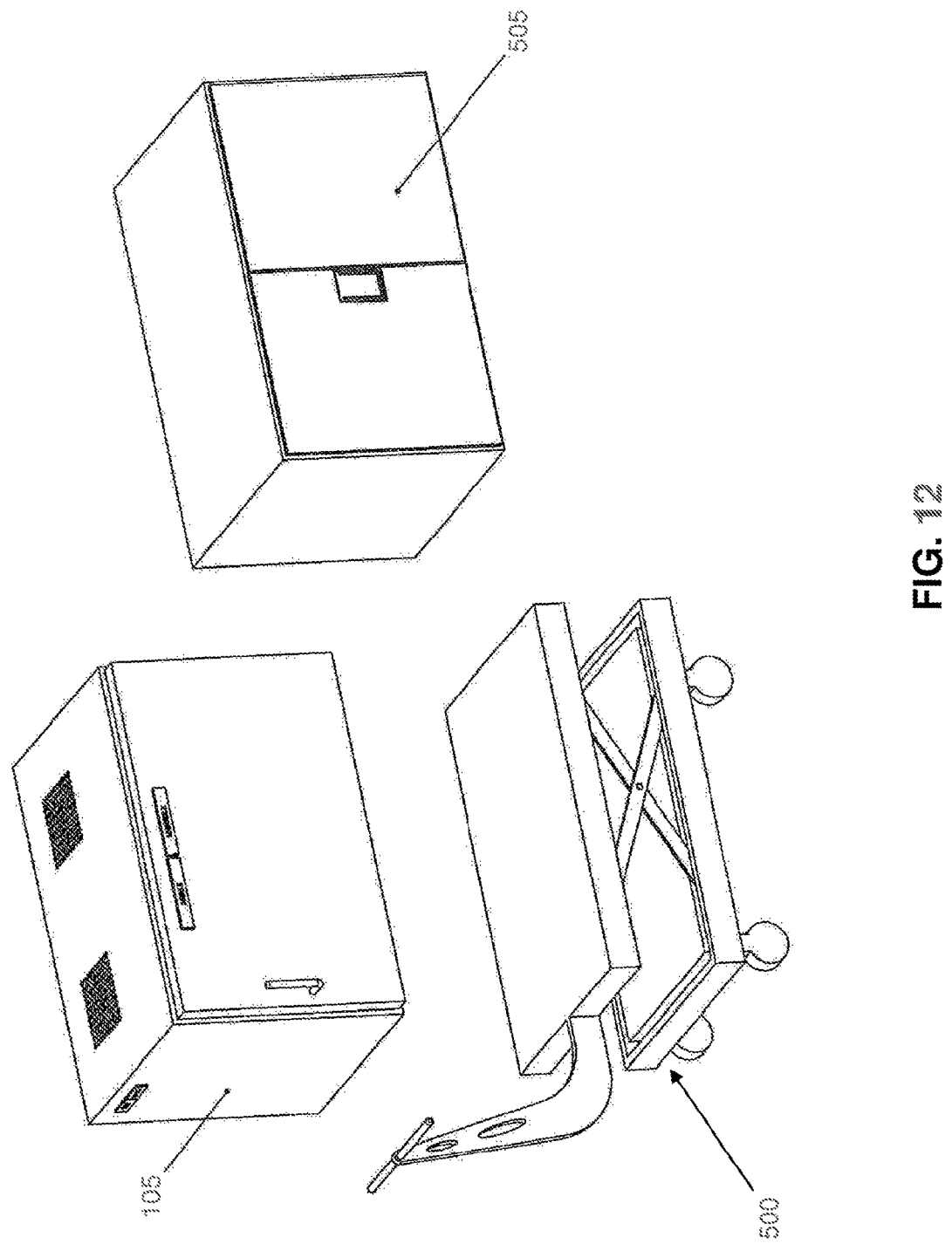
FIG. 12 is a schematic view showing a universal transfer cart formed in accordance with the present invention.
Figure 20:
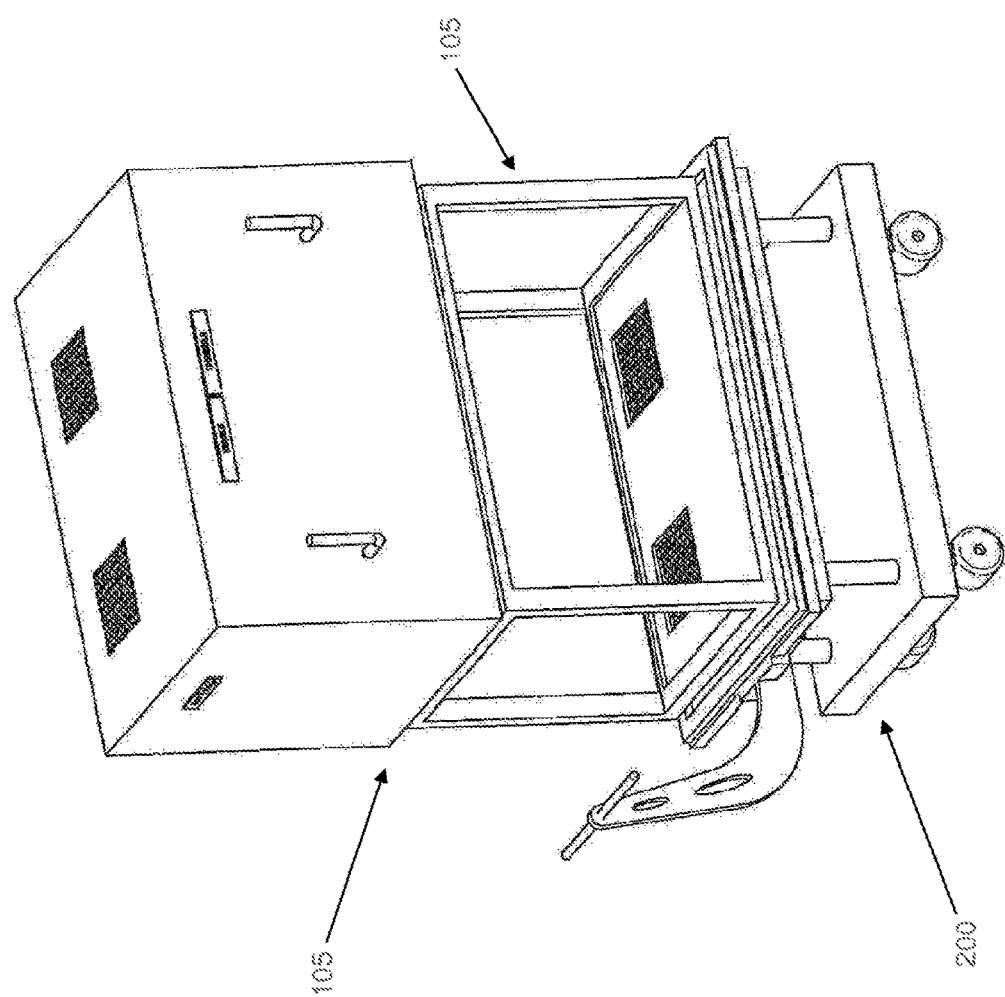

Looking now at FIG. 12, a universal transfer cart 500 is provided. Universal transfer cart 500 may act as a transfer cart for other apparatus (e.g., an interchangeable case cart component 505 for holding instrument trays, but not sterilizing instrument trays) in addition to acting as a transfer cart for sterilization cabinet 105. Sterilization cabinets and case cart components can be vertically stacked on storage racking systems, e.g., up to 4 cabinets high. See, for example, FIG. 20, which shows (schematically) two sterilization cabinets 105 vertically stacked on top of one another.

Looking now at FIGS. 13-27, additional features of sterilization cabinet 105 will now be discussed in further detail.

In a preferred form of the present invention, door 130 can be provided in a variety of configurations in order to minimize the footprint needed when access to the interior of sterilization cabinet chamber 105 is required.

Figure 13:
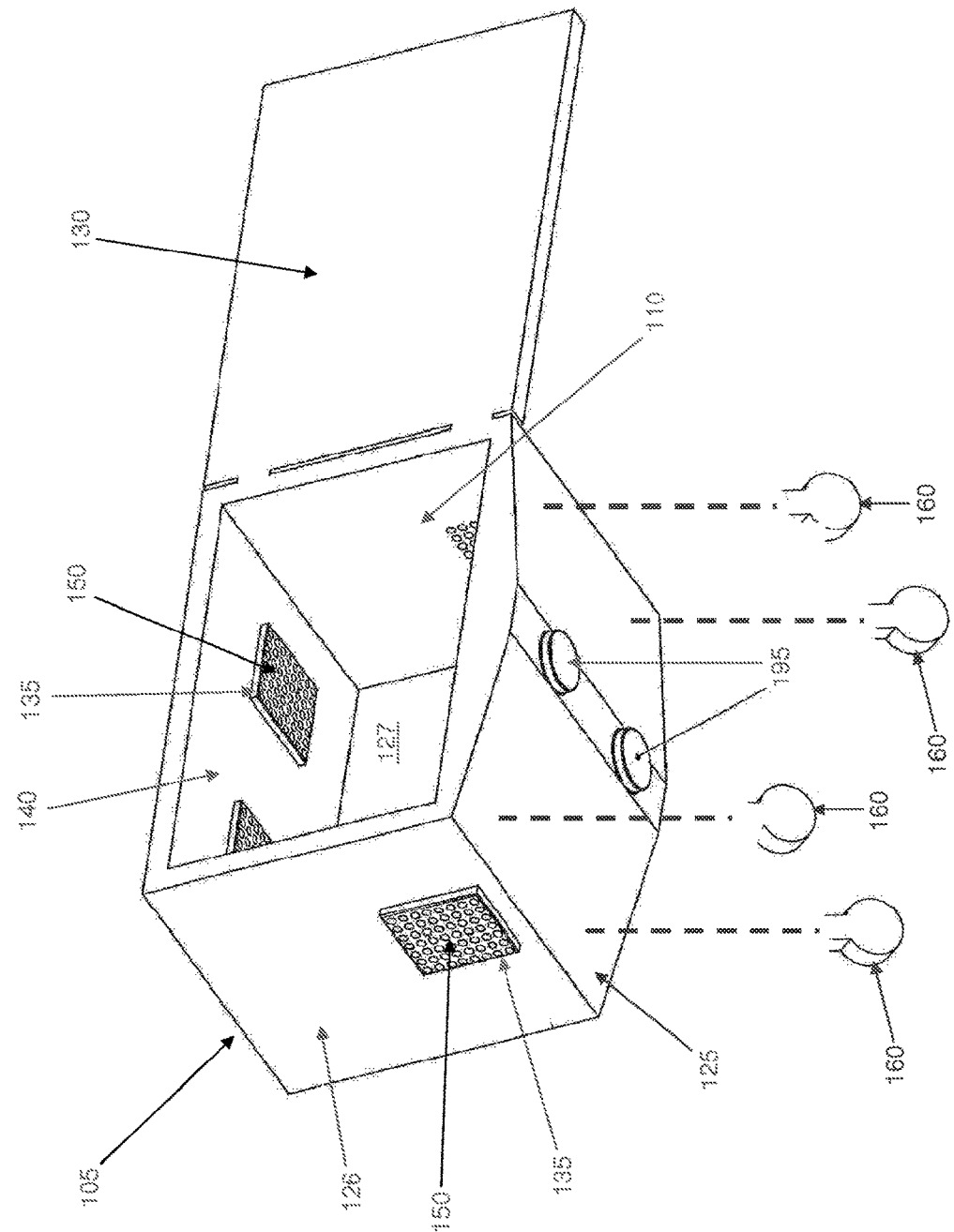
FIGS. 13-21, 22A, 22B, 23, 24, 25A and 25B are schematic views showing further details of the mobile sterilization system of the present invention.

In one embodiment of the present invention, and looking now at FIG. 13, door 130 can be hinged to one side of sterilization cabinet 105 and opened 180 degrees.

Figure 14:
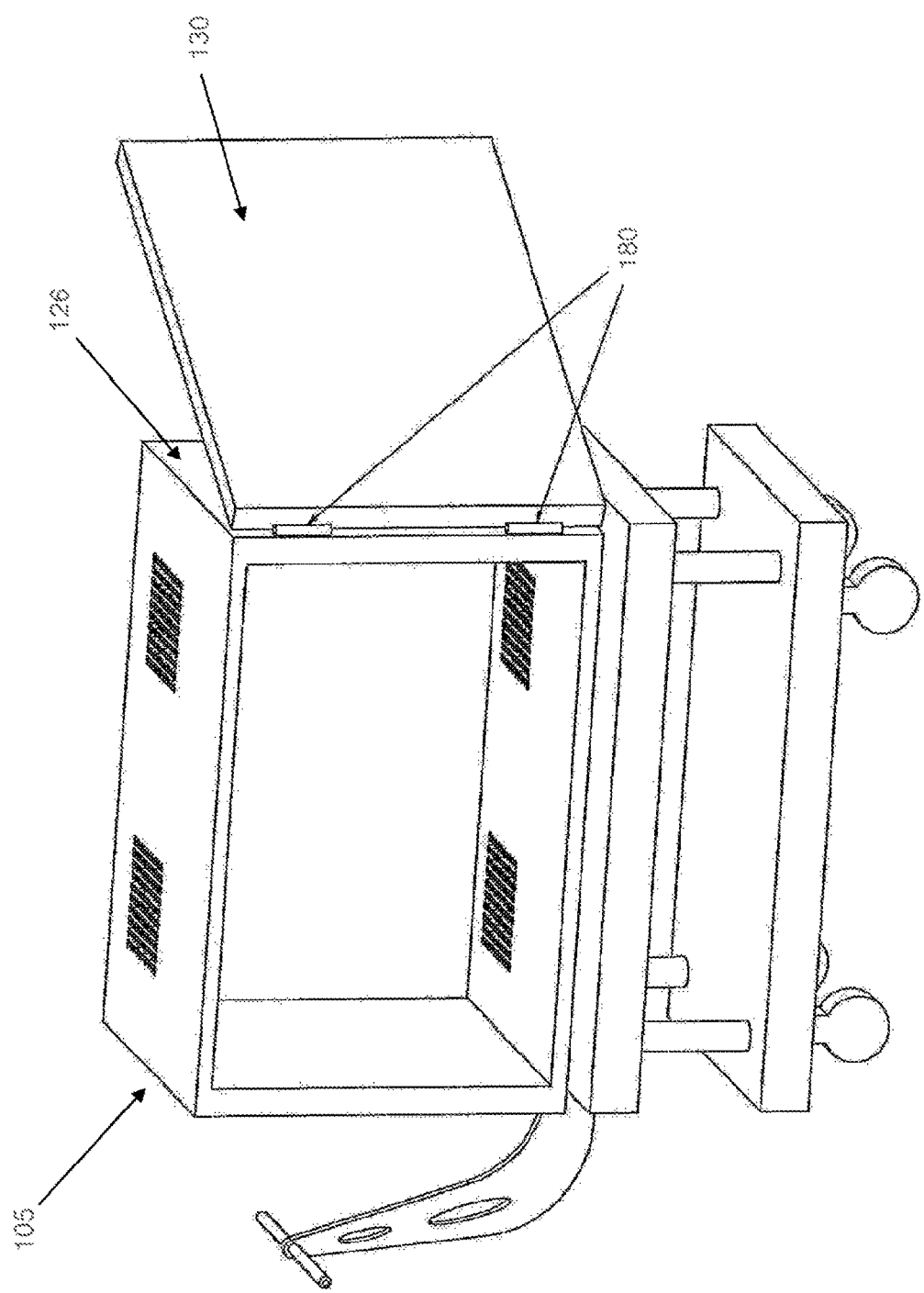

In another embodiment of the present invention, and looking now at FIG. 14, door 130 can be mounted to cabinet side wall 126 with hinges 180 so as to allow door 130 to open 270 degrees. If desired, door 130 and side wall 126 may be equipped with apparatus (e.g., a "hook and mesh" fastener, such as a Velcro™ fastener) so as to allow door 130 to be releasably secured to side wall 126 of cabinet 105 in order to keep the open door proximate to (and roughly parallel to) side wall 126 of cabinet 105, thereby reducing the overall footprint of cabinet 105 when door 130 is open.

Figure 15:
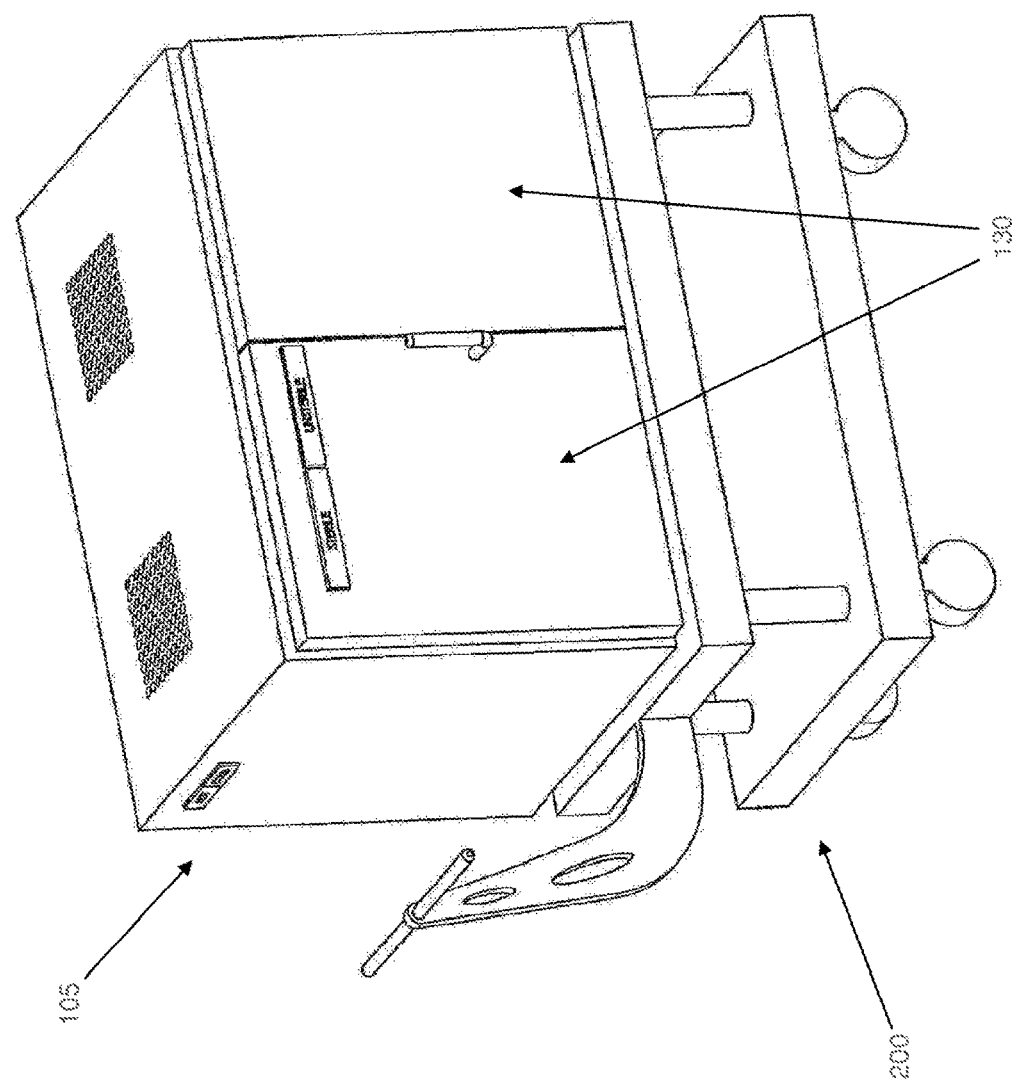

In another embodiment of the present invention, and looking now at FIG. 15, door 130 can comprise a pair of French doors 130, with a gasket or other sealing closure in the middle of, and around, each door 130 (not shown), and with both French doors 130 optionally being configured to be opened and releasably attached to the side of the cabinet in the manner described above.

Figure 16:
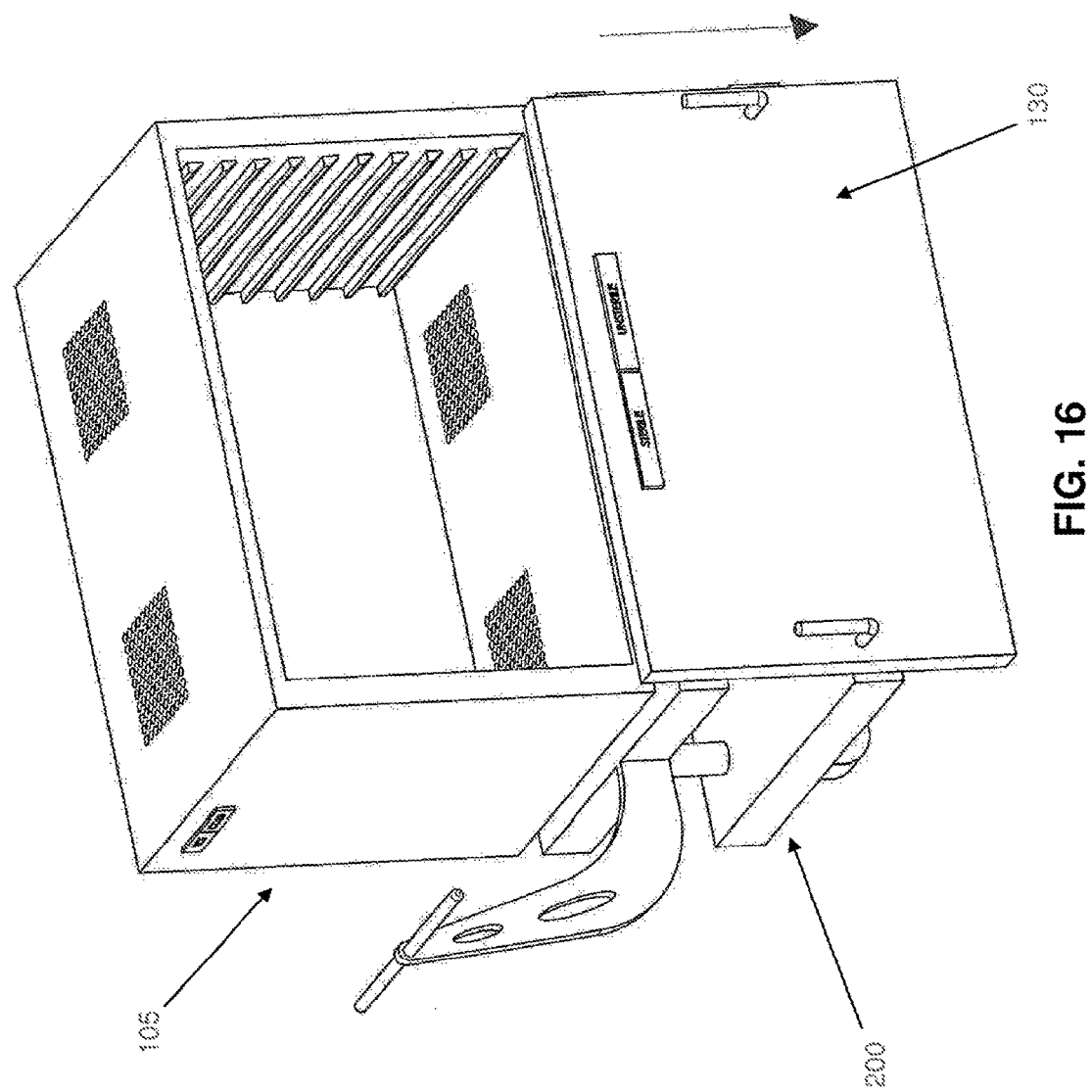
Figure 17:
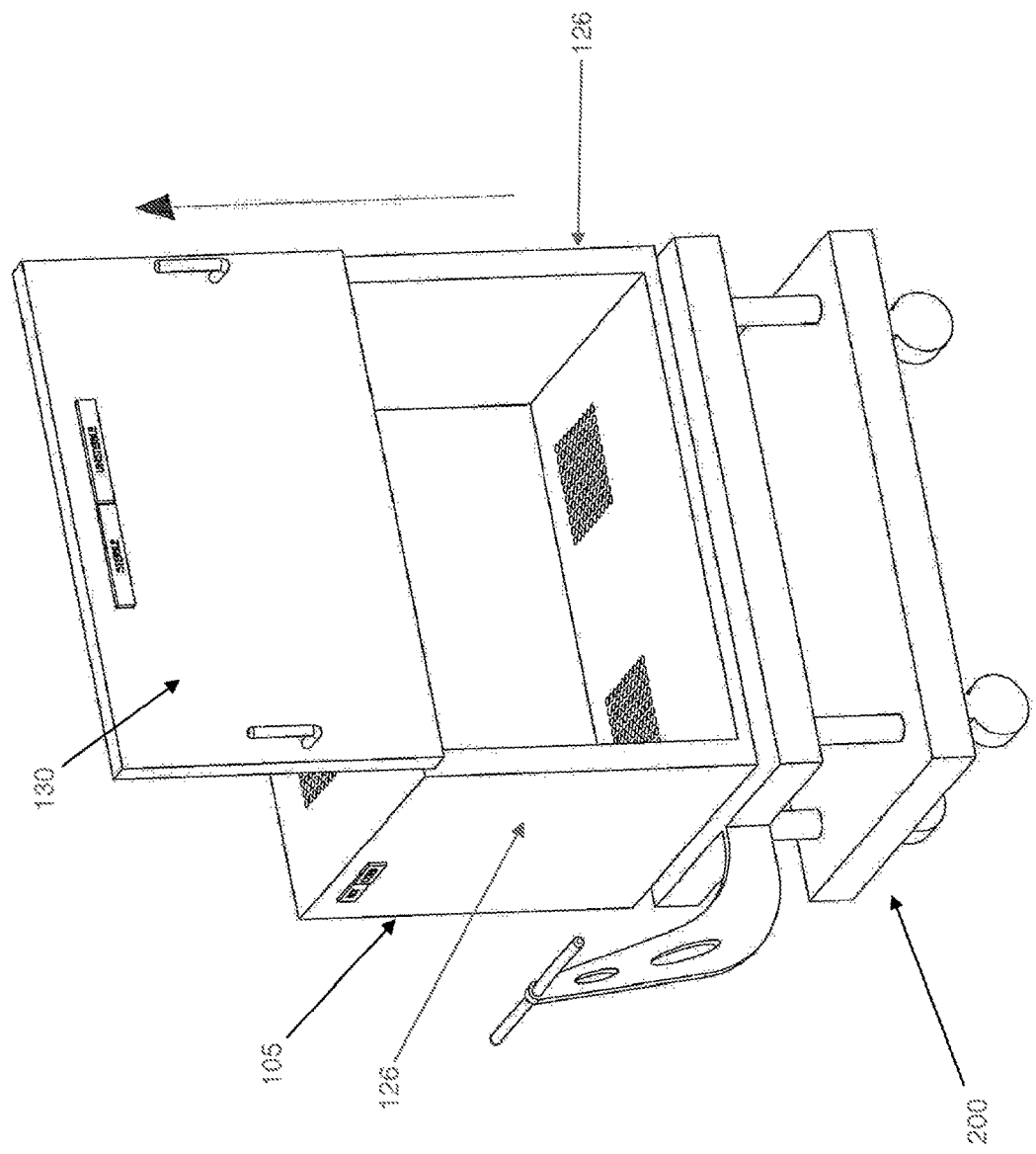

In still another embodiment of the invention, and looking now at FIGS. 16 and 17, door 130 can be opened and slid down (as in FIG. 16) or up (as in FIG. 17) along an internal or external track (not shown) positioned along the left and/or right side walls 126 of sterilization cabinet 105. Alternatively, door 130 may be swung over the top of sterilization cabinet 105 (not shown).

Figure 18:
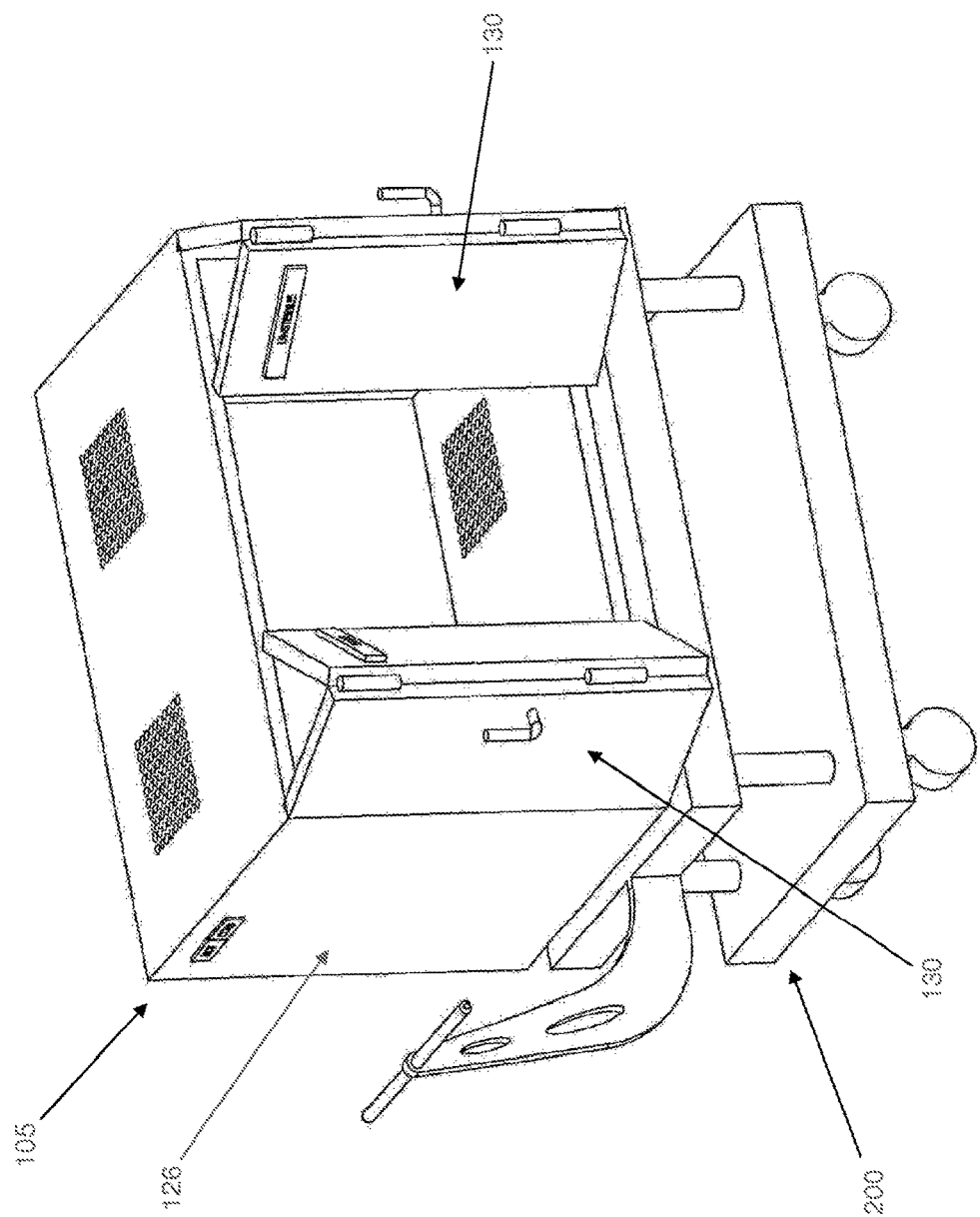

In yet another embodiment of the present invention, and looking now at FIG. 18, door 130 may comprise one or more bi-fold door(s) 130 which may be opened (and folded away) so as to expose interior chamber 110. In one preferred form of the invention, bi-fold door(s) 130 are constructed so that they may be folded back 270 degrees (e.g., in the manner described above) so that door(s) 130 may be positioned approximately parallel to side wall 126 of sterilization cabinet 105. Additionally, bi-fold door(s) 130 and side walls 126 are preferably constructed so as to allow door(s) 130 to be releasably secured to side walls 126 (e.g., with a "hook and mesh" fastener, e.g., a Velcro™ fastener) when door(s) 130 are folded back against side walls 126.

In another form of the present invention, the sterilization cabinet can have a dome closing top (not shown) rather than a door, i.e., the top of the sterilizable cabinet can move upward to expose the contents of the sterilization cabinet. The shape of the dome top is generally configured to allow for an airtight fit around the sterilization cabinet.

Accordingly, the dome top may be any shape that allows it to be properly fit over the top of the frame of sterilization cabinet 110. In this embodiment, the dome top can be lifted (e.g., manually, mechanically, with electronic assist, etc.) to expose the contents of sterilization cabinet 105. If desired, the dome top may be formed of a transparent material so as to allow full visibility of the contents within sterilization cabinet 105.

Figure 19:
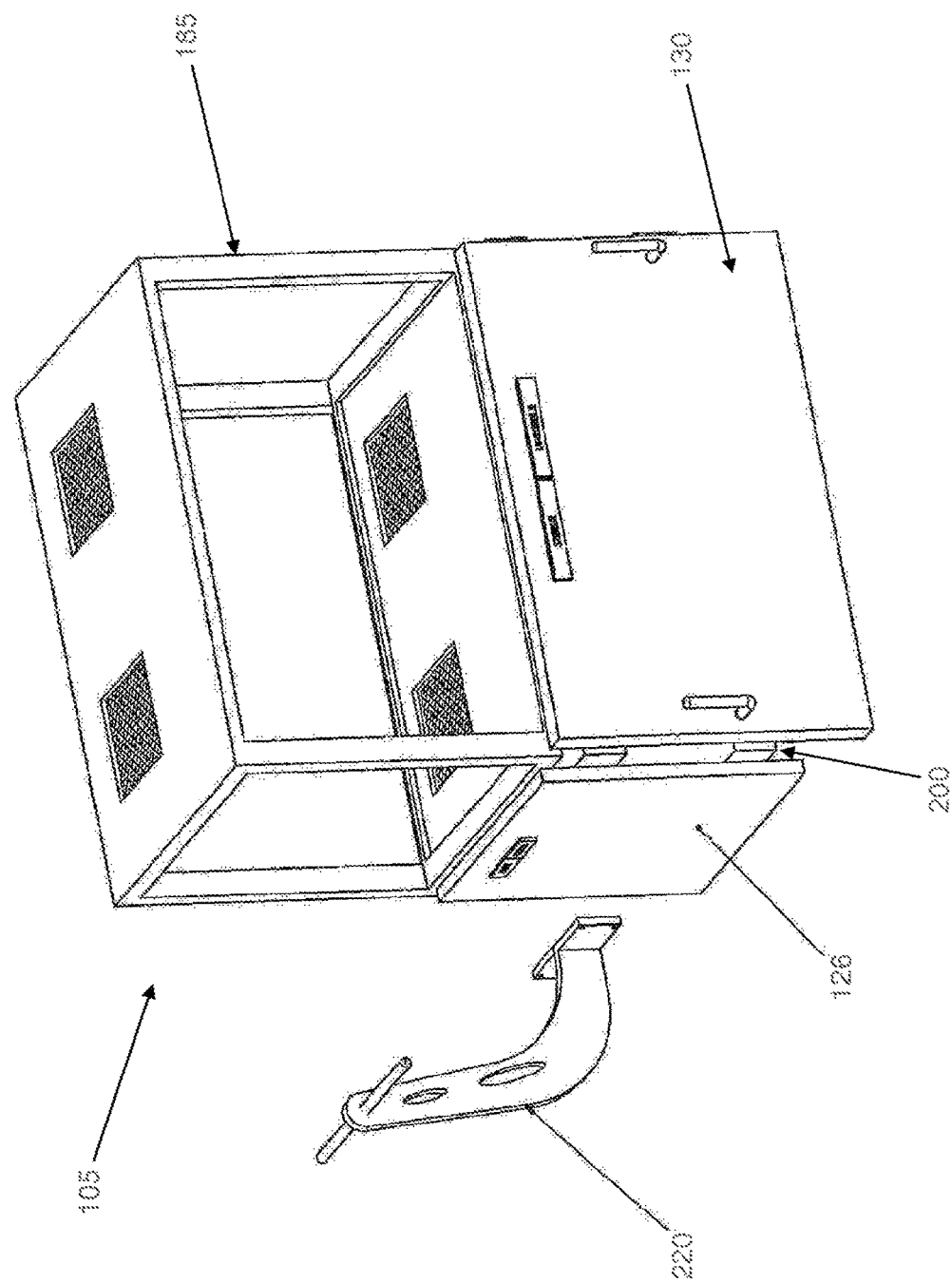

In still another form of the present invention, and looking now at FIG. 19, sterilization cabinet 110 may comprise a frame wherein back wall 127, side walls 126 and door(s) 130 can be loosened from frame 185 and slid down along internal or external tracks to the outside of the transfer cart 200. In this embodiment of the invention, handle 220 of transfer cart 200 may be removable so as to facilitate the smooth sliding of the side walls and/or door along the tracks.

In another preferred form of the present invention, means may be provided to enable a user to assess the contents of the sterilization cabinet without having to open the door of the sterilization cabinet.

More particularly, the entire sterilization cabinet 105 may be formed out of a transparent material (e.g., glass, a transparent polymer, etc.) so as to provide visibility to the contents within the sterilization cabinet. See, for example, FIG. 20, which shows a transparent sterilization container 105 positioned on top of transfer cart 200, and a second non-transparent sterilization container 105 positioned on top of transparent sterilization container 105.

Figure 21:
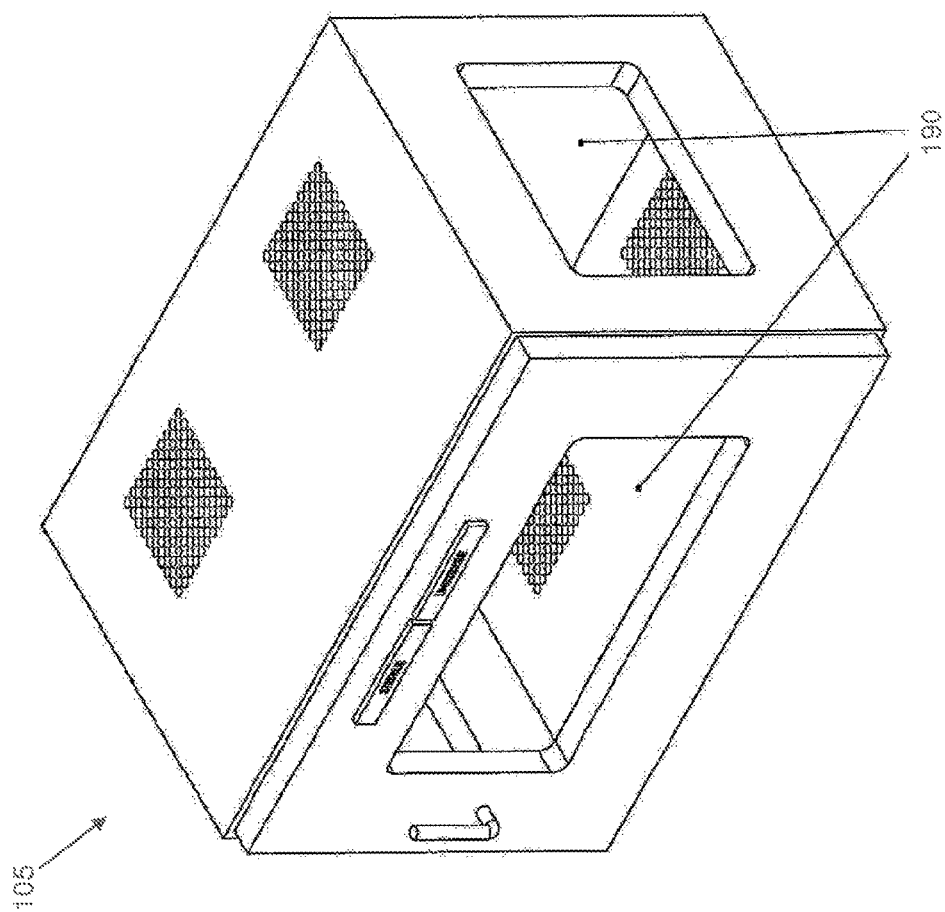
Figure 22:
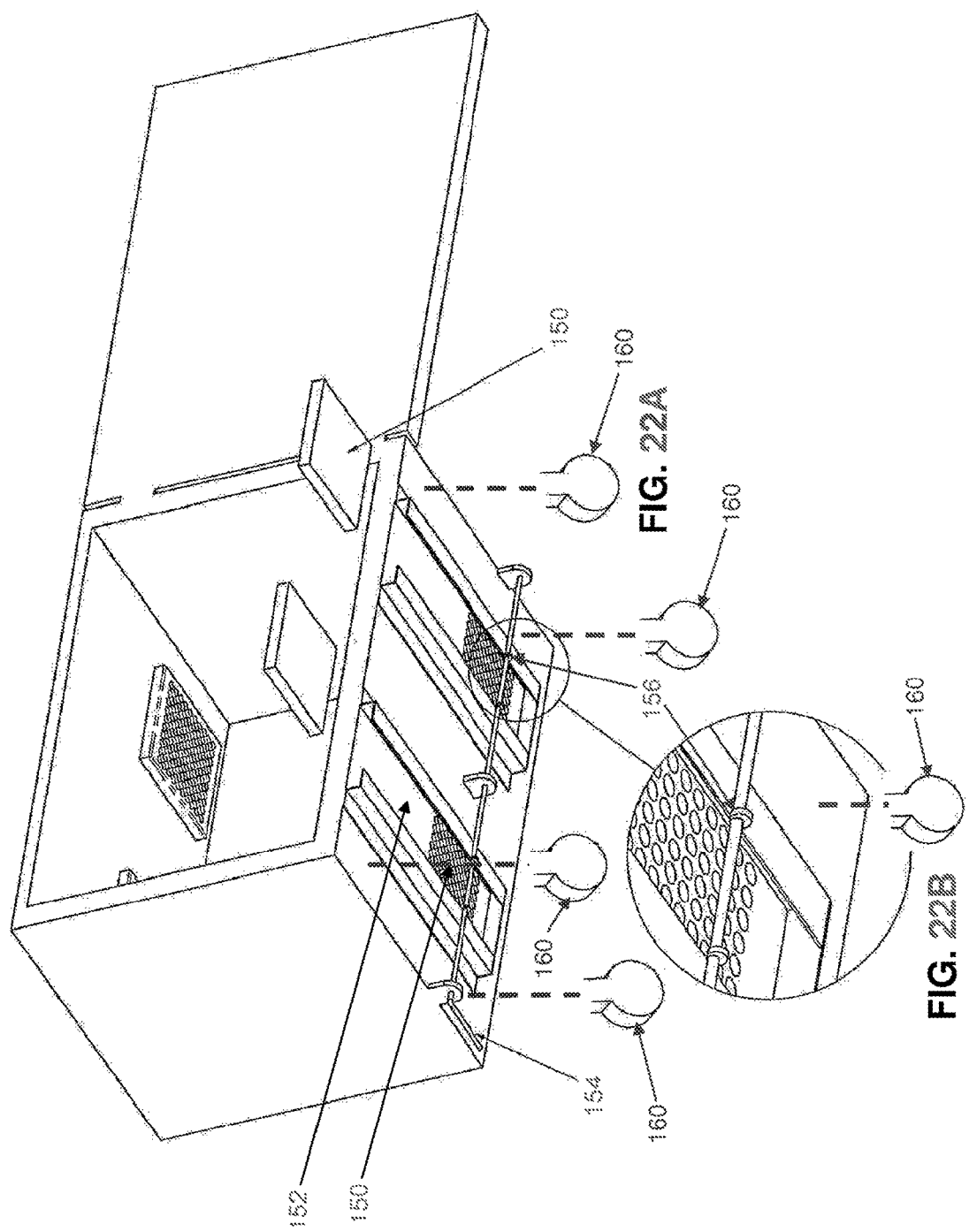

In another embodiment, and looking now at FIG. 21, sterilization cabinet 105 may be provided with one or more windows 190 (or "oven doors") located on one or more of the side walls 126, back wall 127 or door(s) 130 of sterilization cabinet 105. This allows for visibility into the cabinet to ascertain the contents of the cabinet and whether all of the desired equipment and instruments are enclosed.

If desired, the entire cabinet or window(s) 190 may be formed of a high temperature polycarbonate material and/or a "switchable" smart glass/film that changes from clear to opaque and/or another suitable material (e.g., to indicate a "sterile" or "non-sterile" state).

In another form of the present invention, an improved filter and filter port is provided in order to improve access to the filter for replacing, or otherwise accessing, the filter. Looking now at FIGS. 22A and 22B, sterilization cabinet 105 may be provided with filter ports 152 that are accessible from the outside of the cabinet, thereby allowing for easier access to check and change filters 150 (e.g., easier than with filter cover 155). By way of example but not limitation, externally accessible filter port 152 may comprise a drawer-type access shelf for slidably receiving filters 150 and positioning the filter over vent 135. After being slidably placed in the desired position over vent 135 in filter port 152, filters 150 may be held in place by a locking bar 154 which controls a cam mechanism 156 (which releasably locks filters 150 in place).

Filter 150 may comprise cardboard, filter cassettes, reusable carbon filters or other filter materials and constructions known in the art. Filter 150 may also be a bi-layer filter created by sewing, gluing, encasing, crimping or pressing two layers of filter material together and forming to a desired size. Filter 150 may also be configured to change color to convey information concerning their status (e.g., a first color may indicate that a filter is suitable for use, while a second color may indicate that a filter should not be used and should be replaced, etc.). Thus, in one preferred form of the invention, the filter is manufactured using a process that incorporates chemical (s) into or onto the filter (in whatever pattern desired, including one requested by the customer) that will change color after the sterilization cabinet has been sterilized (as long as the sterilization process met certain predetermined parameters). In other words, the filters themselves become a Class 5 status indicator in addition to all of the other indicators which may be used during the sterilization process. This type of filter is a great improvement over the filters currently available on the market, as it provides a fail-safe mechanism to ensure that single use disposable filters are used only once. It also enables the operating room staff to visually confirm that the process has been accomplished by a quick glance at the large filter material.

Filters 150 may also be used for purposes other than in conjunction with an existing sterilization cabinet and/or mobile sterilization system 100.

In some applications of the present invention, it may be appropriate to not use any filters with the cabinets.

Looking again at FIG. 13, sterilization cabinet 105 may have a drain 195 positioned in the cabinet floor 125 to allow for the removal of water that may have accumulated within the cabinet during the sterilization process. In this construction, drain 195 is placed at the lowest point in the bottom of sterilization cabinet 110. Preferably, bottom panel 125 is designed with a pitch to the lowest point in the panel, whether in the middle of the panel or along one side of the panel or in a corner of the panel. One or more drains may be used in each cabinet.

If desired, drain 195 may be thermostatically-controlled. In this form of the invention, drain 195 may be formed with a so-called "bimetallic" construction, e.g., a shape memory alloy such as Nitinol which can change configuration in response to temperature changes. By way of example but not limitation, drain 195 may be configured to open when the temperature within the sterilization cabinet is higher in order to release the excess water created during the sterilization process, and to close when the temperature within the sterilization cabinet is lower so as to seal the sterilization cabinet from potential containments.

In another embodiment, drain 195 may be configured to open and close depending on the pressure level within the sterilization cabinet. By way of example but not limitation, drain 195 may be configured to open when the pressure within the sterilization cabinet is within a certain level in order to release the excess water created during the sterilization process, and to close when the pressure within the sterilization cabinet is within a certain level so as to seal the sterilization cabinet from potential containments.

In still another embodiment, drain 195 may be configured to open and close depending on the amount of time that has lapsed since the sterilization process. By way of example but not limitation, drain 195 may be configured to open during the time it takes to sterilize the contents of the sterilization cabinet in order to release the excess water created during the sterilization process, and to close after the contents of the sterilization cabinet have been sterilized so as to seal the sterilization cabinet from potential containments.

In a further embodiment of the present invention, sterilization cabinet 110 comprises improved shelf management options so as to provide less cumbersome interior shelving than prior art sterilization cabinets.

Figure 23:
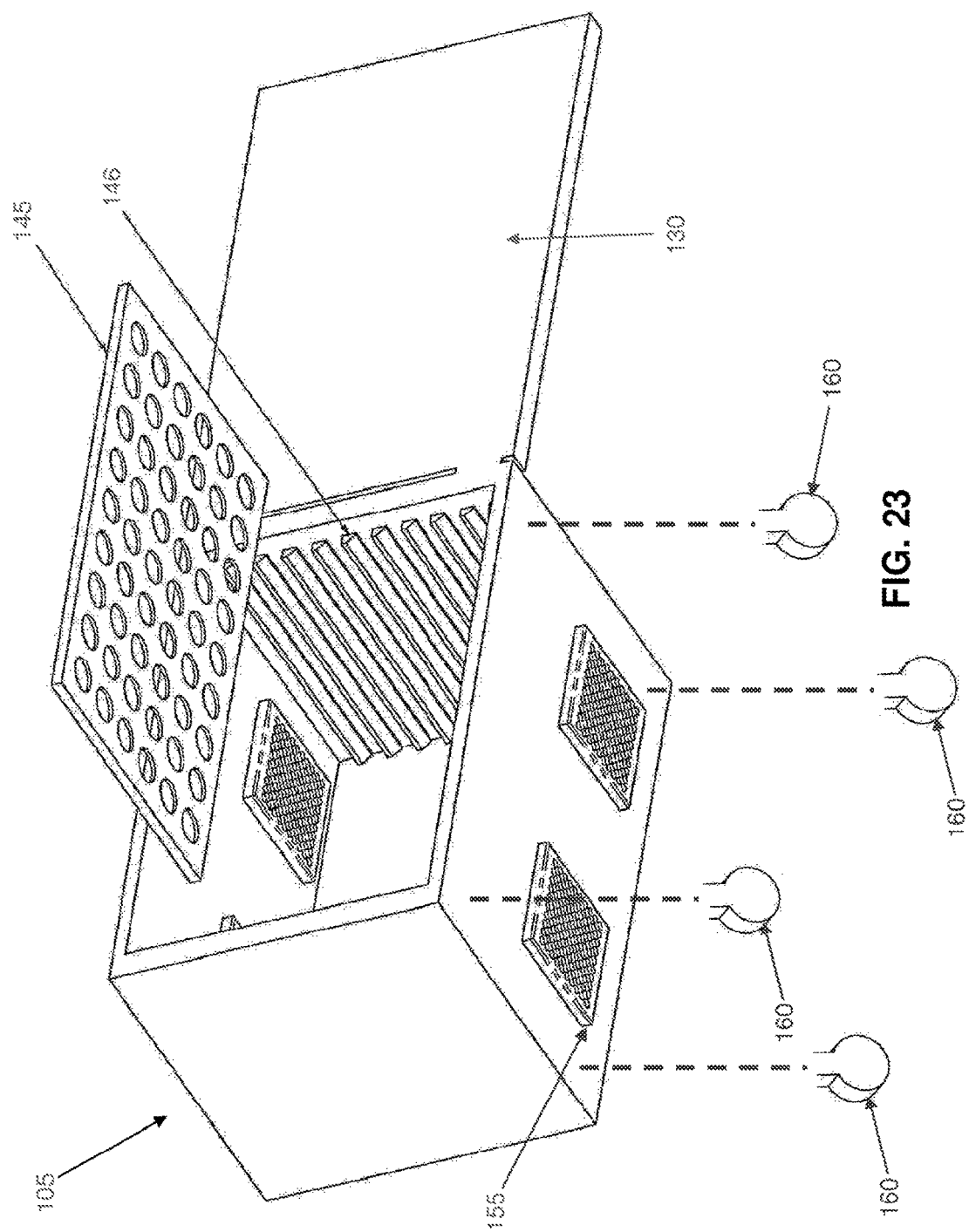

More particularly, and looking now at FIG. 23, sterilization cabinet 105 may be configured with "wrinkle walls" or stamped walls 146 for ease of removing and replacing shelves 145 at multiple heights without the need for adjusting clips within the cabinet. In this aspect of the invention, shelves 145 are adjustable into varying height positions, which adjustments may preferably be accomplished with one hand (e.g., through the use of "squeeze and release" shelving or other similar alternatives).

Figure 24:
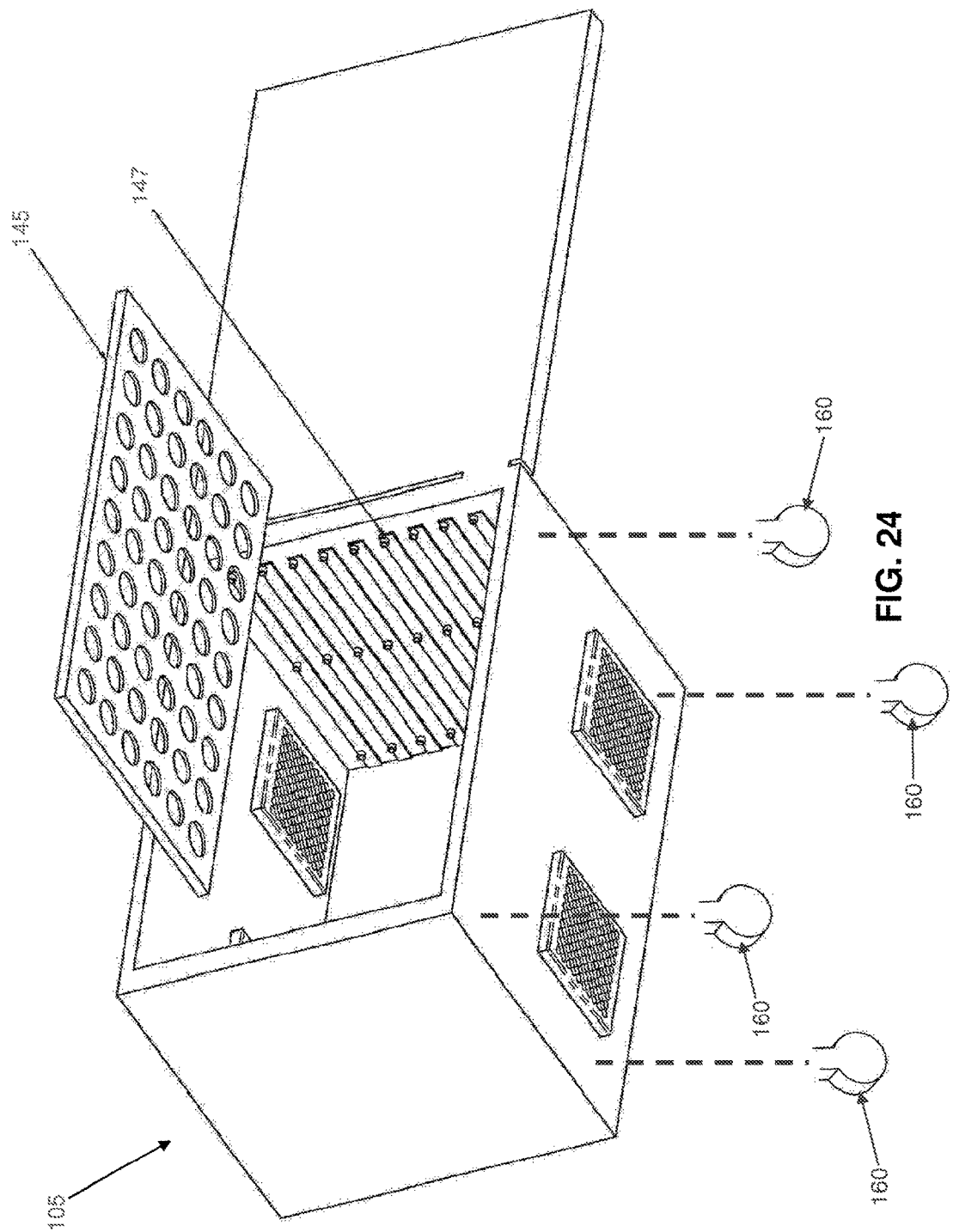
Figure 25:
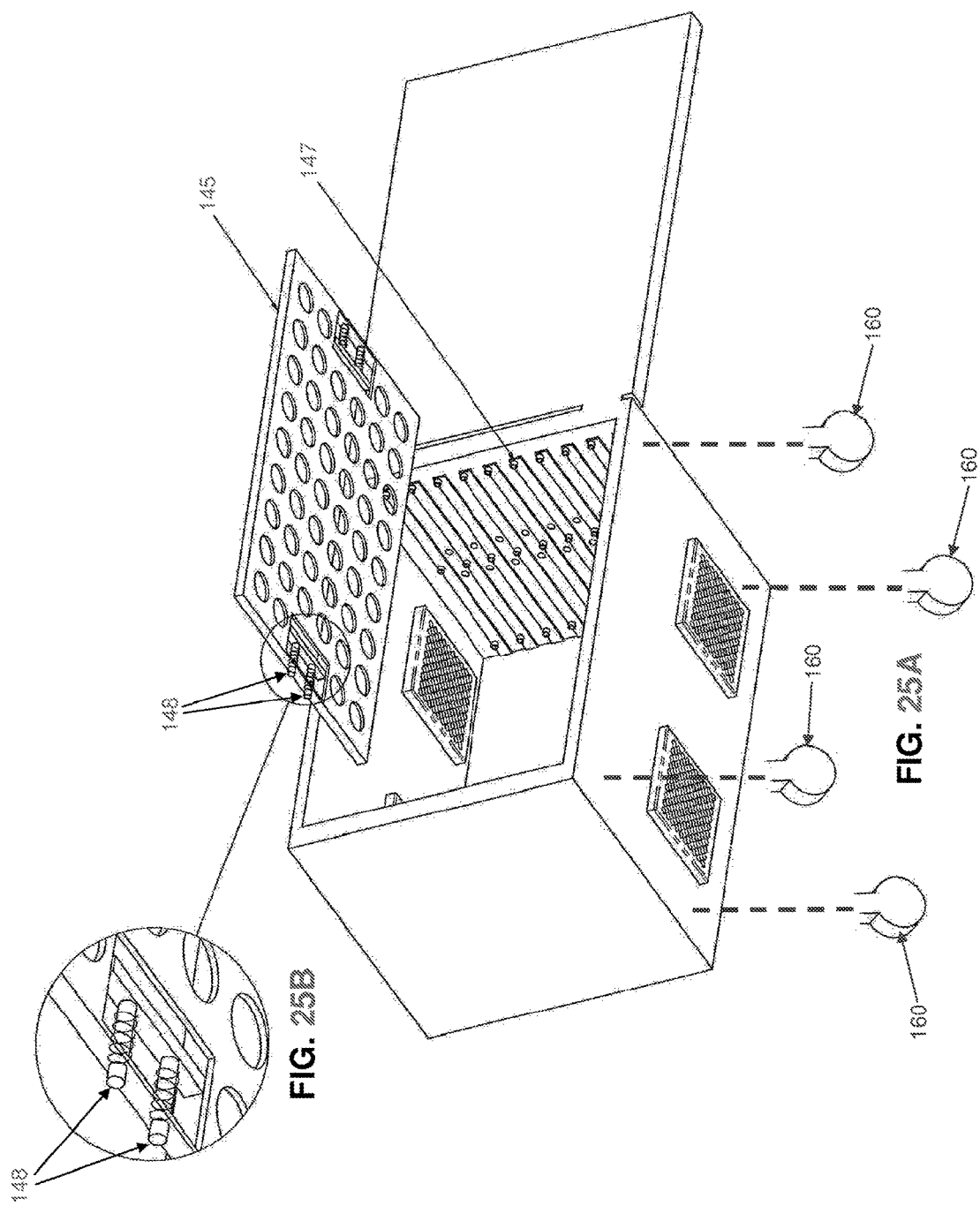

Alternatively, and looking now at FIG. 24, shelving supports 147 may be bolted to cabinet 110 so as to support shelves 145.

In still another aspect of the invention, and looking now at FIGS. 25A and 25B, shelves 145 may be attached to shelving supports 147 by spring-loaded pegs 148.

In another embodiment, drawer-style shelves may also be used (not shown). In addition, the shelves may be constructed of various materials which may aid in the sterilization process and/or provide other advantages (e.g., the shelves may be formed of aluminum for better heat transfer, or may be formed of materials that are less expensive, etc.).

In another embodiment, the present invention provides a sterilization cabinet which has the ability to isolate smaller areas inside of the sterilization cabinet.

Figure 26:
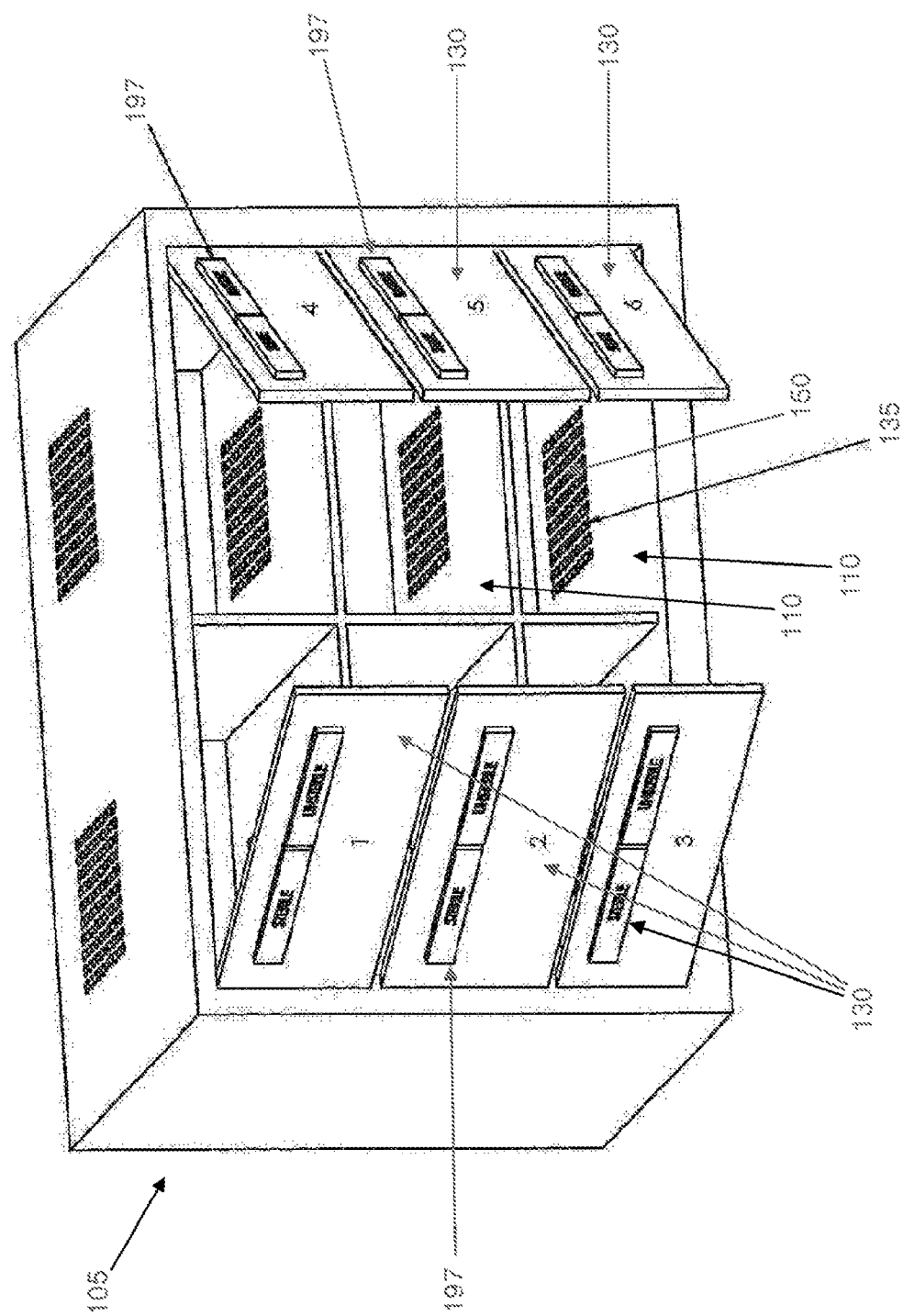
FIG. 26 is a schematic view showing a novel sterilization cabinet formed with multiple internal sterilization chambers.

More particularly, and looking now at FIG. 26, sterilization cabinet 105 is configured so as to provide multiple chambers 110 within cabinet 105. More particularly, in this form of the invention, sterilization cabinet 105 comprises separate individual chambers 110, each of which are accessible by a separate door 130. Preferably, each chamber 110 is provided with its own vent 135 and filter 150 to allow for steam or heat penetration during the sterilization process. In addition, each individual chamber 110 may have a sterile/unsterile indicator 197 (of the same or a similar type as will be described in greater detail below) to indicate the sterile/non-sterile condition of that compartment.

Compartmentalization provides the option of the contents of the several chambers 110 being used in different procedures. In other words, all chambers 110 and their contents can be sterilized at the same time, and then the contents of individual chambers 110 can be used without compromising the sterility of the other chambers 110 or their contents. By way of example but not limitation, four trays (placed in one or more chambers 110) can be brought to an operating room for a "4 tray procedure" (i.e., a medical procedure requiring those four trays of sterilized medical instruments), and another eight trays placed in a separate set of chambers within the same sterilization cabinet 105 can be brought to a second operating room for an "8 tray procedure" (i.e., a medical procedure requiring those eight trays of sterilized medical instruments). Compartmentalized sterilization cabinet 105, in combination with transfer cart 200, can thus serve as a delivery system for more than one medical procedure, providing several efficiencies including, but not limited to, requiring fewer staff to deliver the sterile trays and requiring less equipment to deliver the trays to the desired location.

In addition to the foregoing, sterilization cabinet 105 may be provided with additional features for assisting in the determination of the completion of the sterile processing or for providing additional information about the status of the cabinet (e.g., whether the sterilization cabinet is too hot to open).

By way of example but not limitation, such additional features may include indicators on the windows or panels of the cabinet that change color after sterile processing of the cabinet and then change back after the cabinet is opened (and hence rendered non-sterile).

Figure 27:
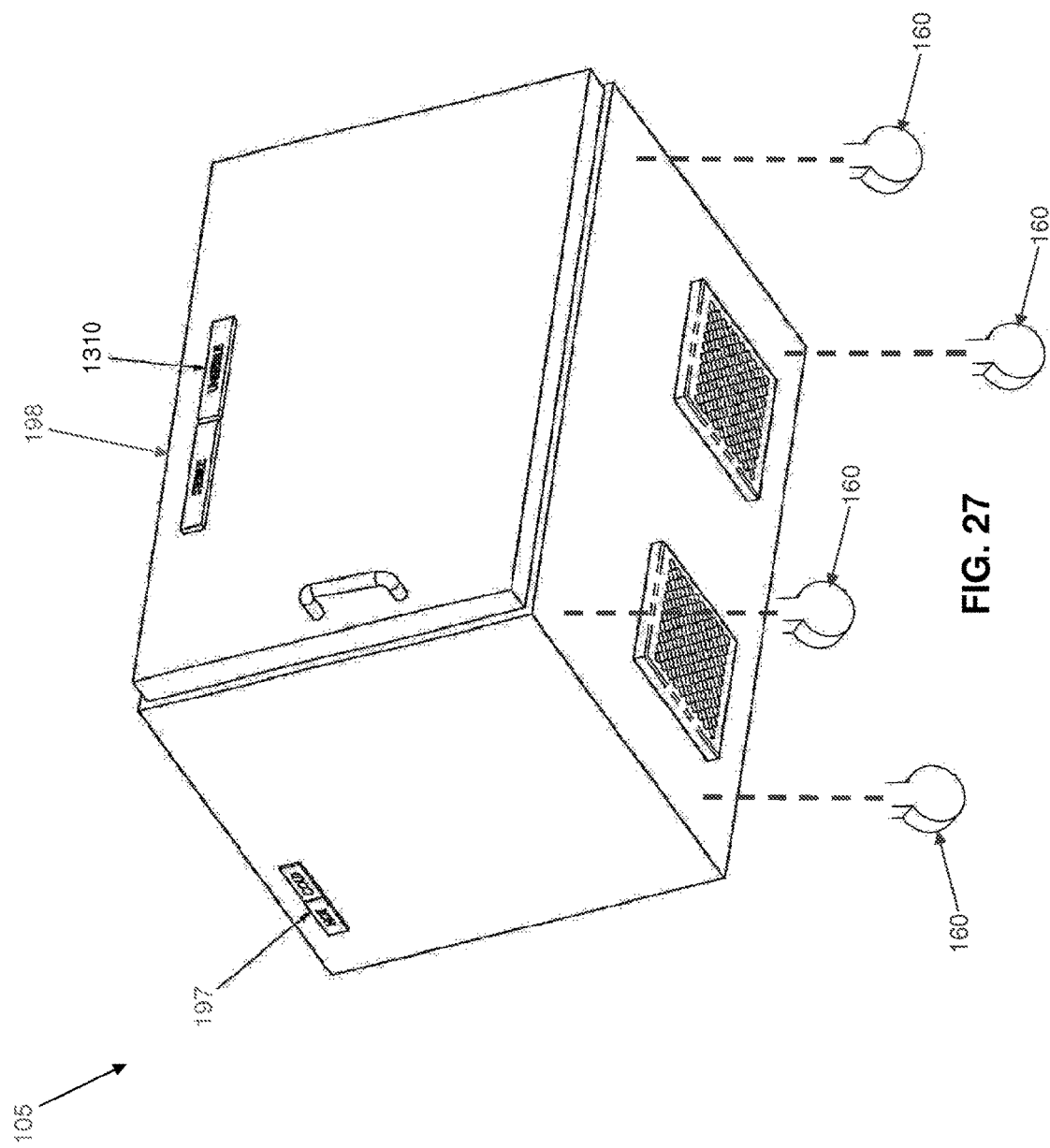
FIG. 27 is a schematic view showing a status indicator feature of the sterilization cabinet of the present invention.
Figure 30E:
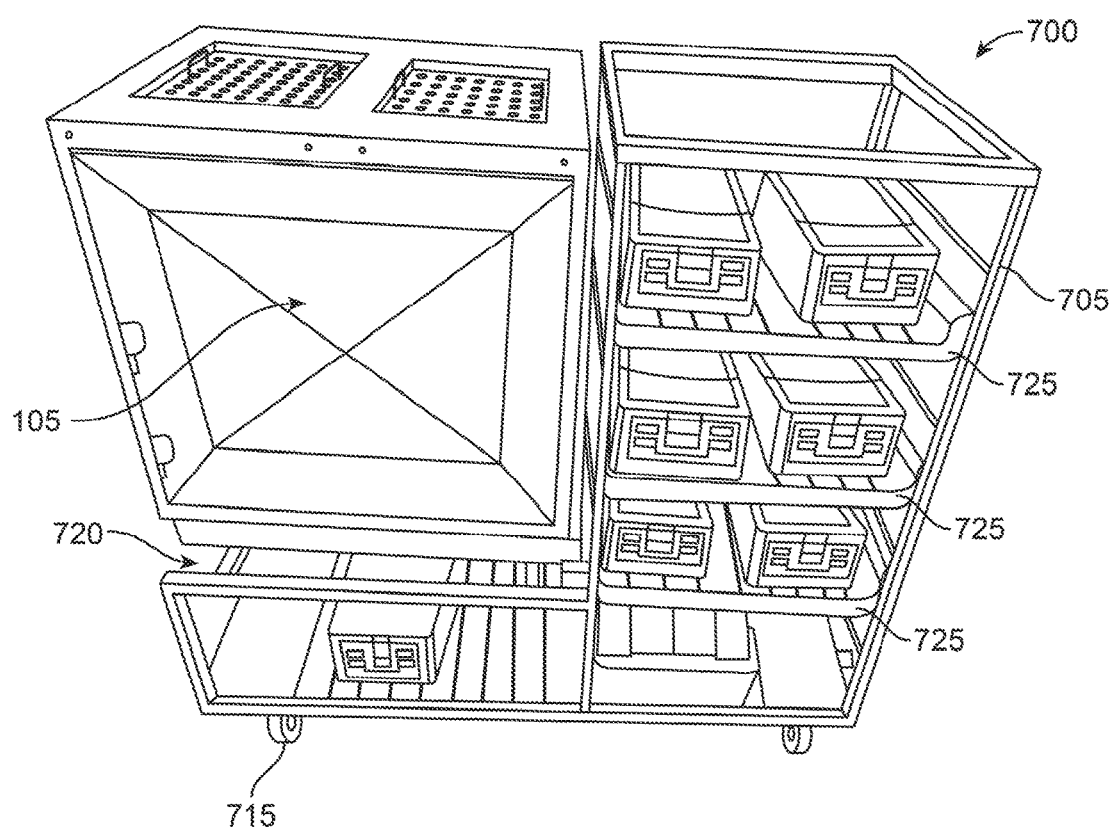
FIG. 30E is a schematic view of a novel docking station formed in accordance with the present invention.
Figure 31:
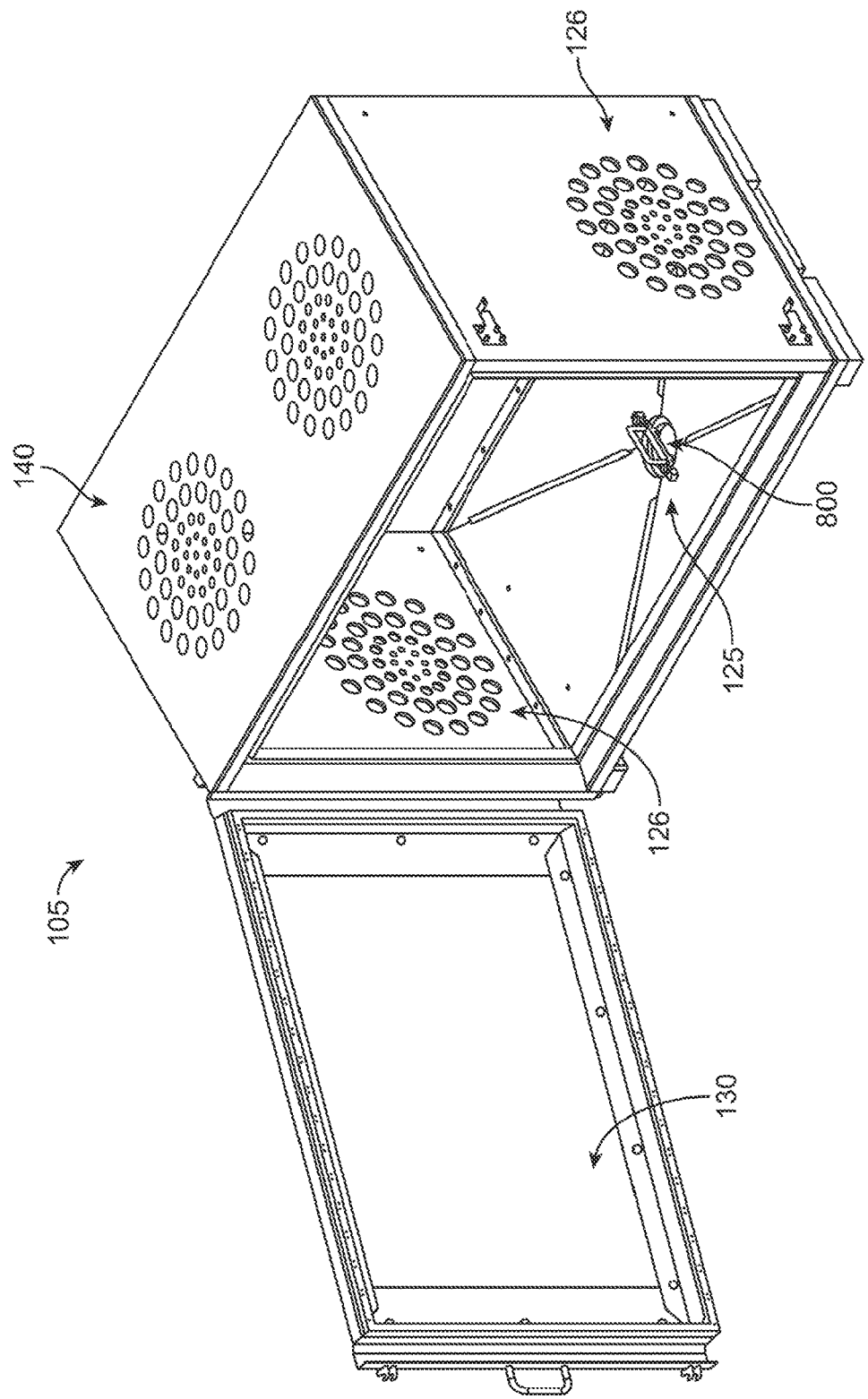
FIGS. 31-41 are photographs of an improved drain and filter assembly for the sterilization cabinet of the present invention.
Figure 32:
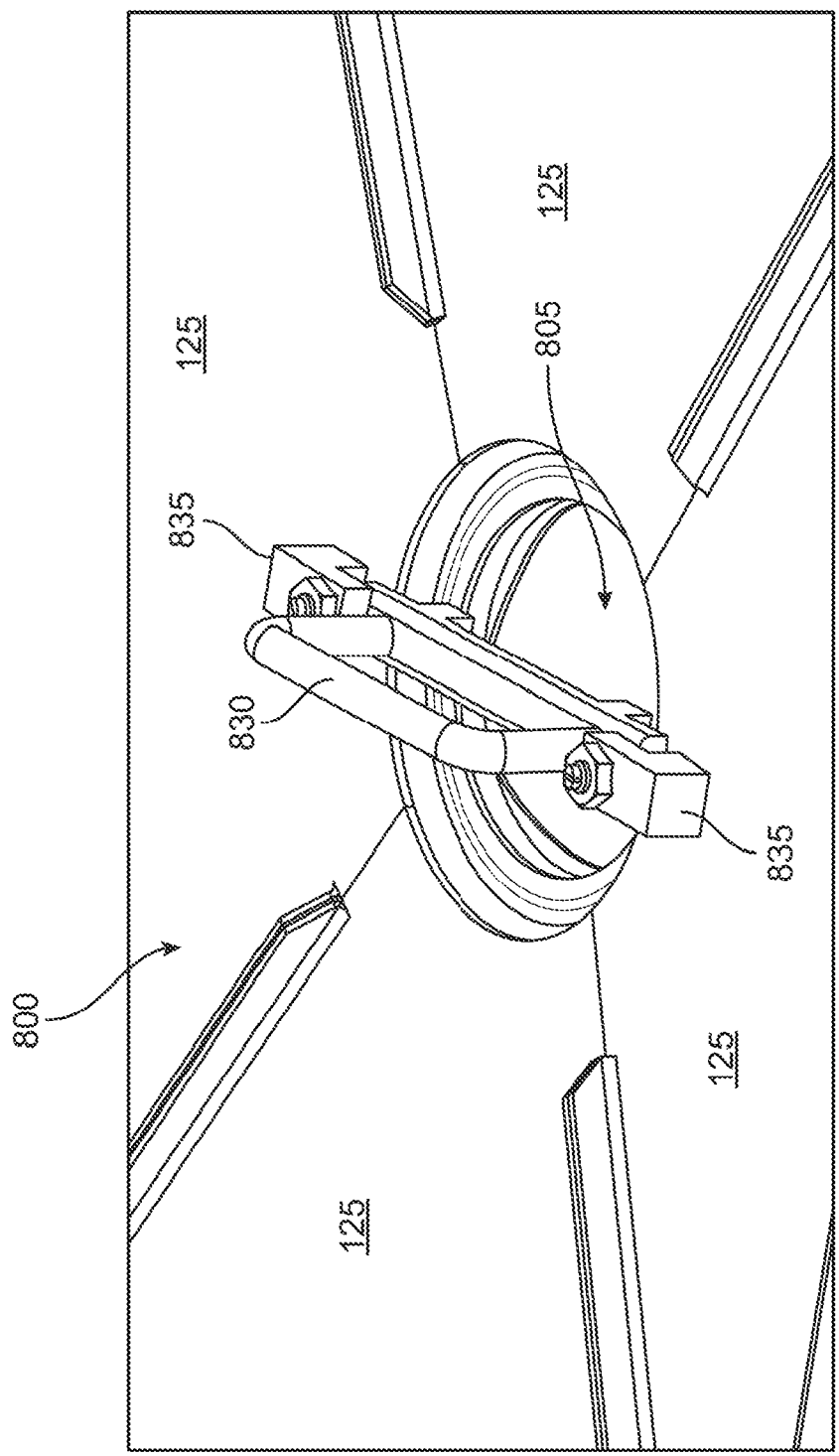
Figure 33:
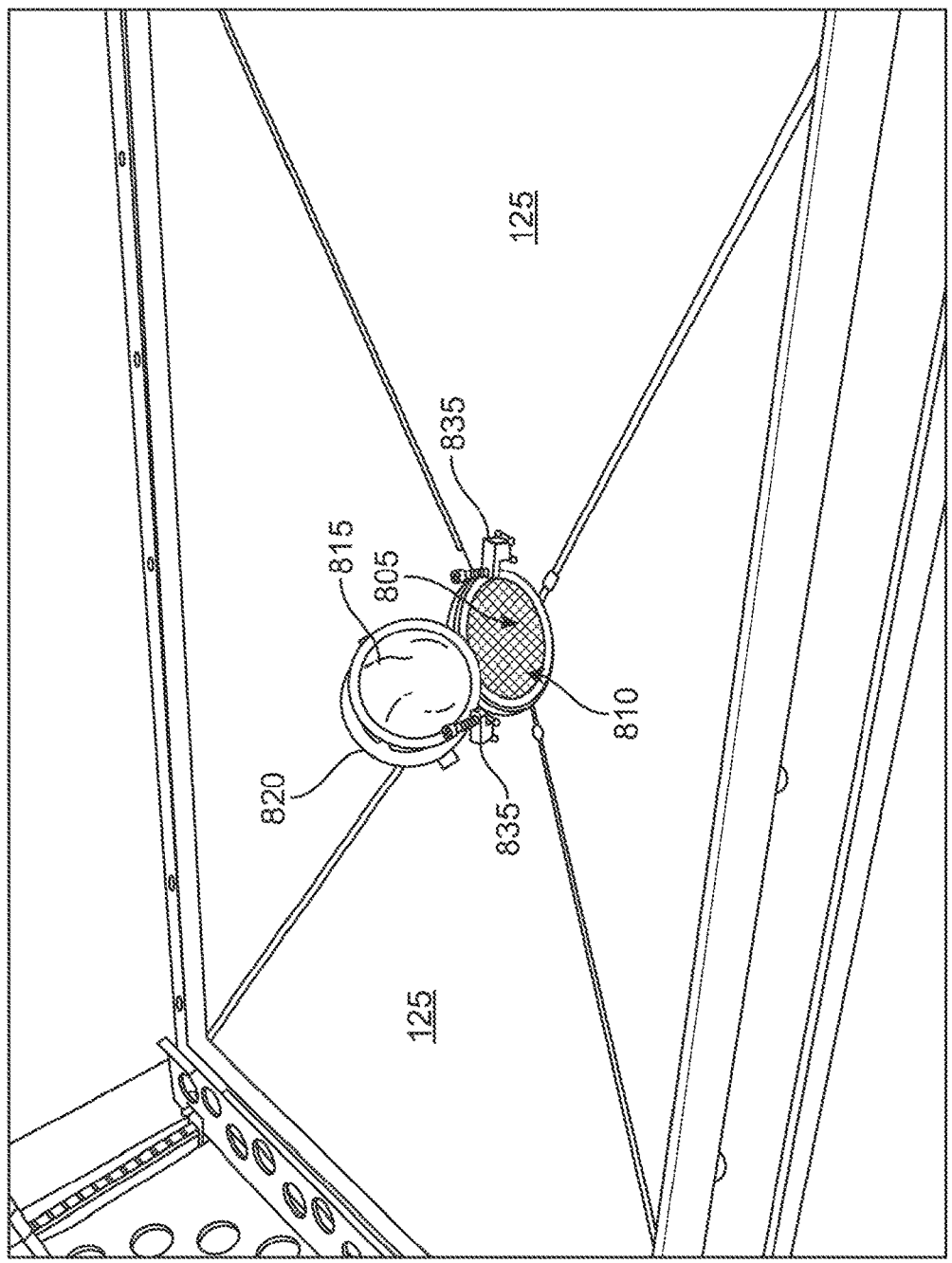
Figure 34:
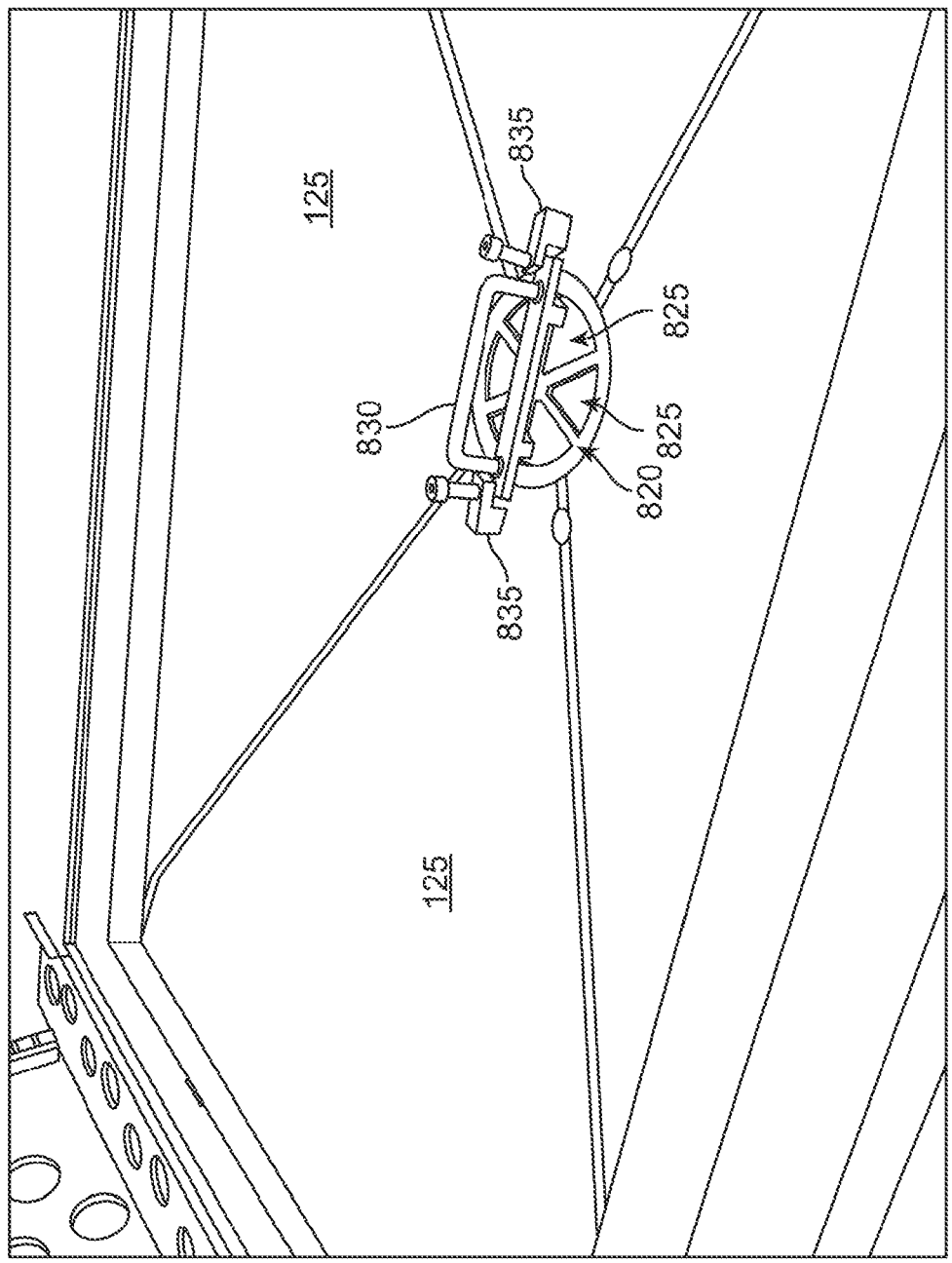
Figure 35:
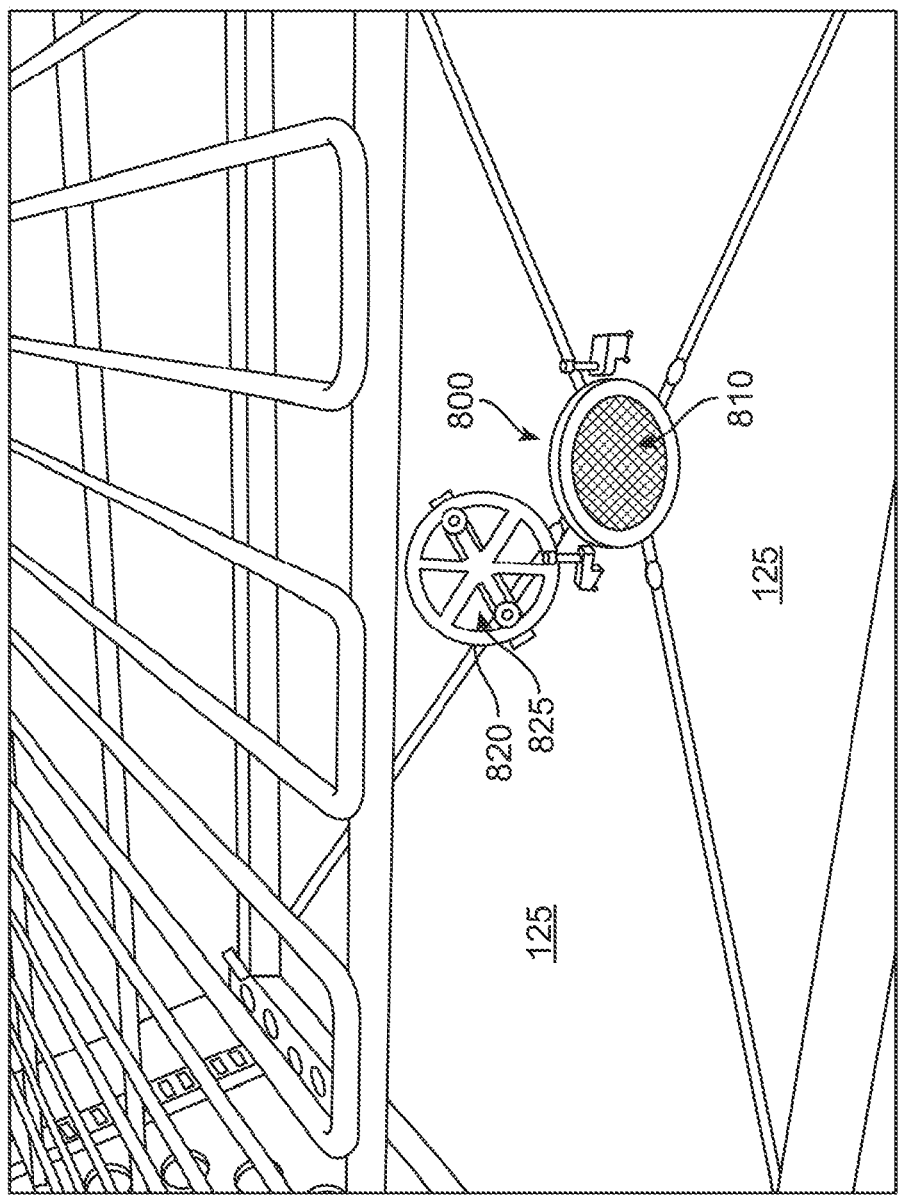
Figure 36:
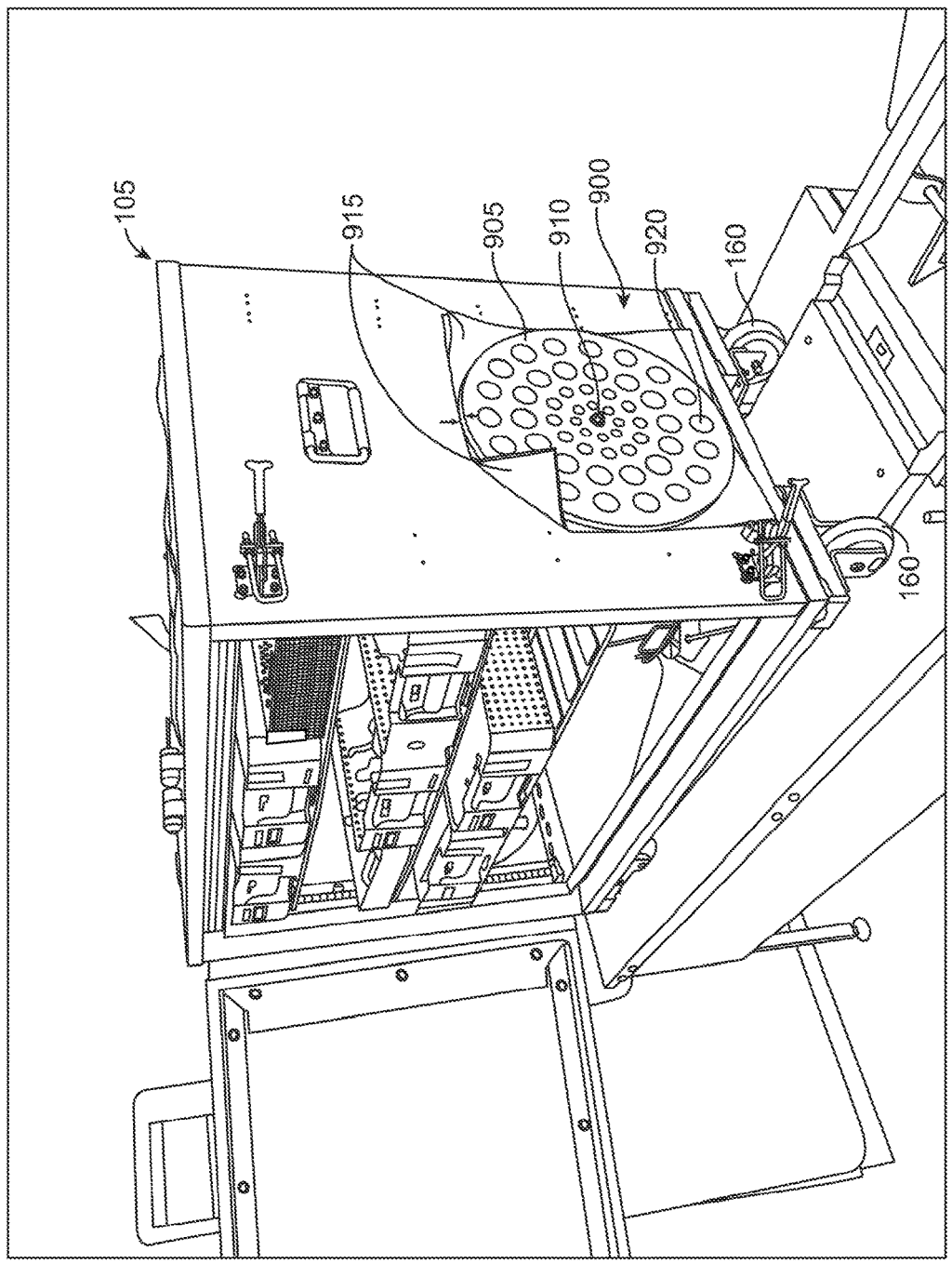
Figure 37:
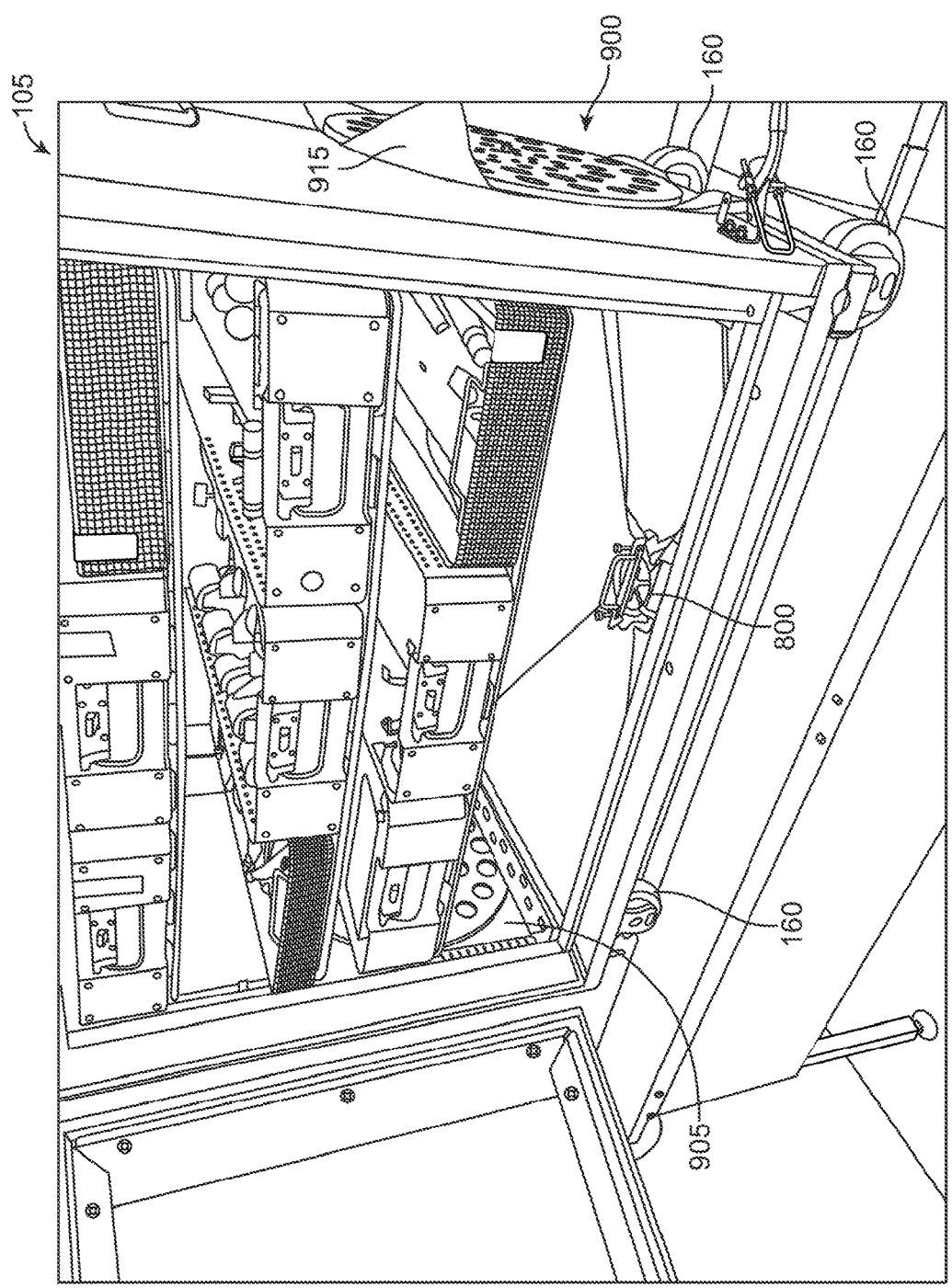
Figure 38:
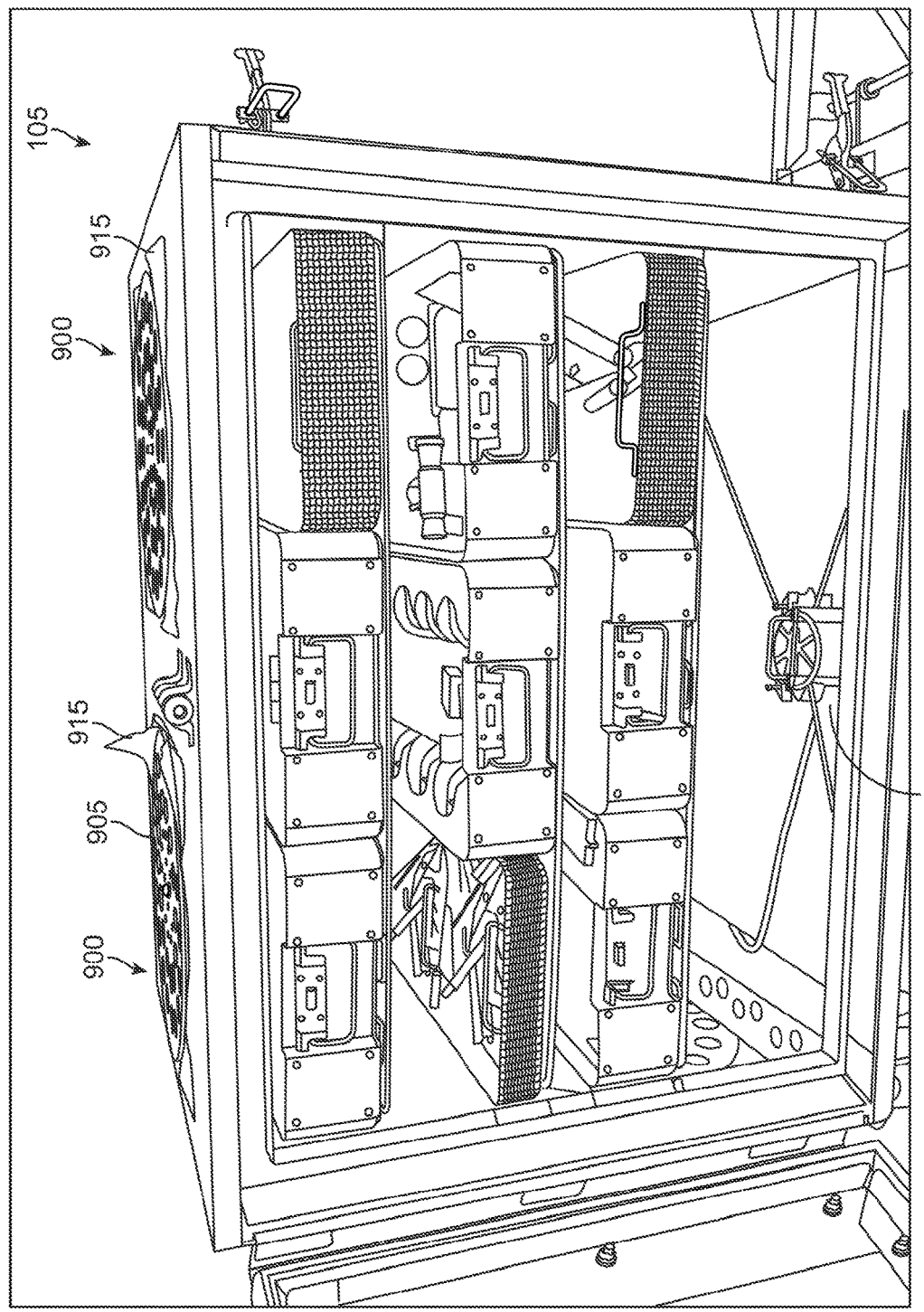
Figure 39:
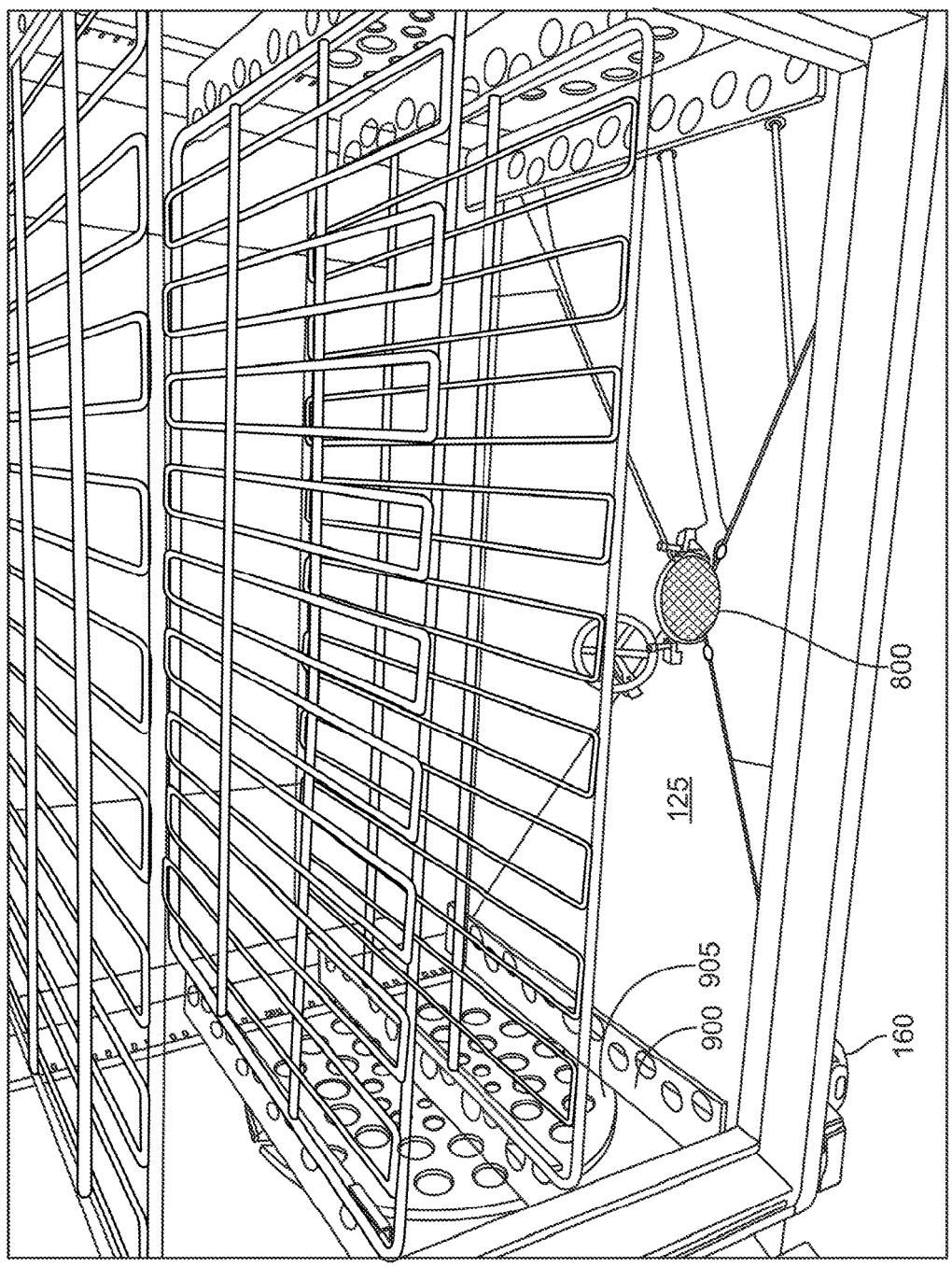
Figure 40:
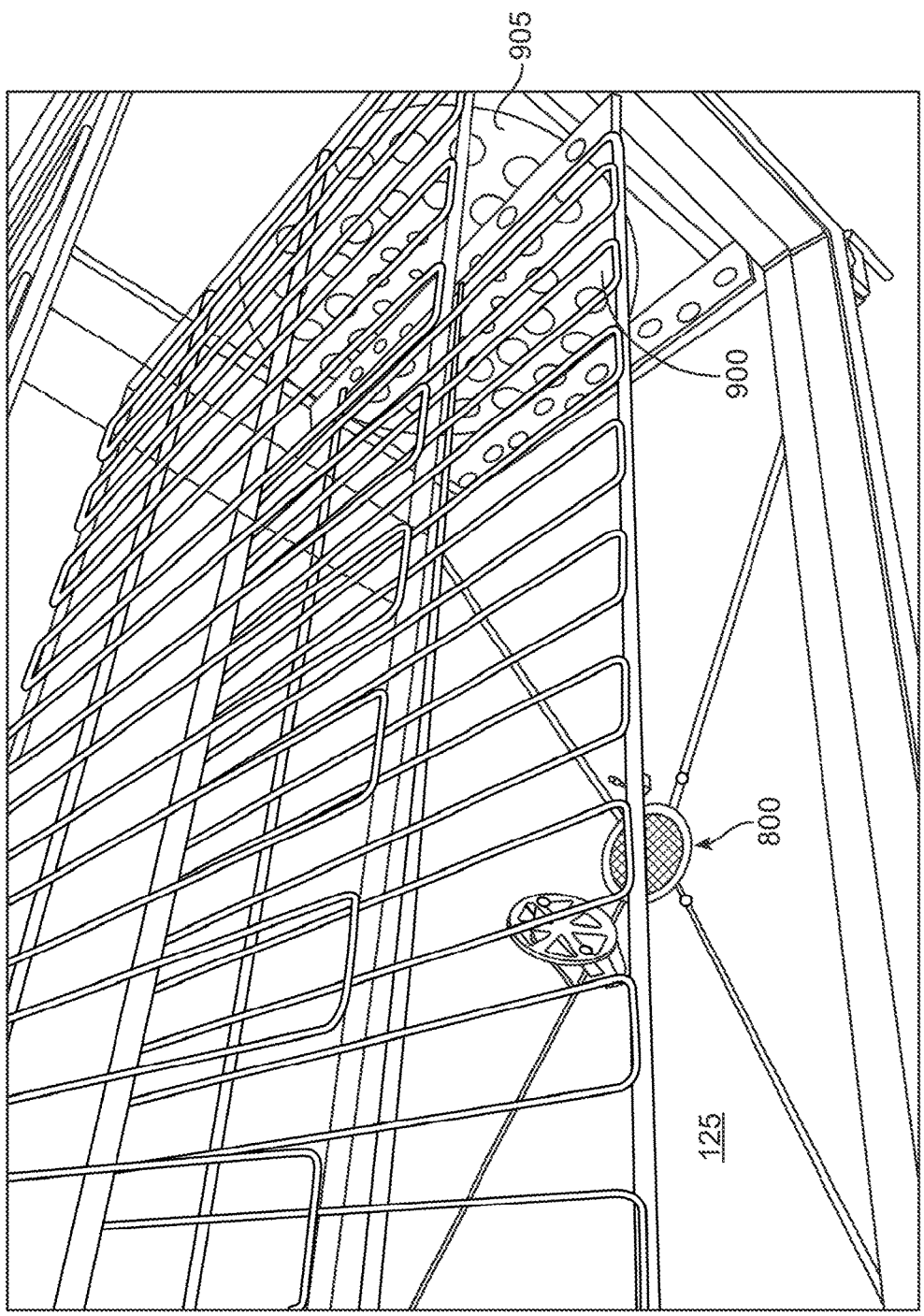
Figure 41:
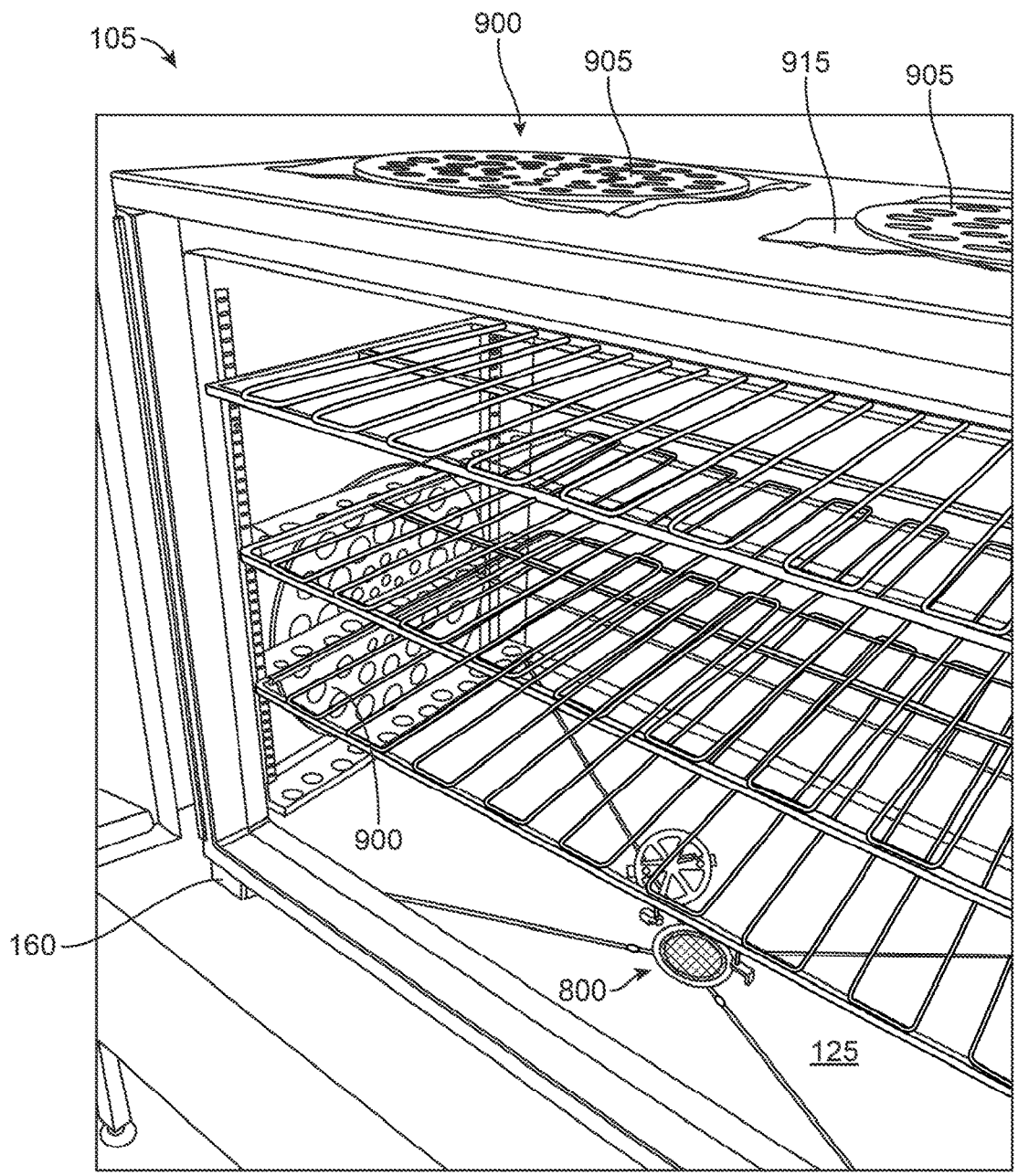
Figure 42:
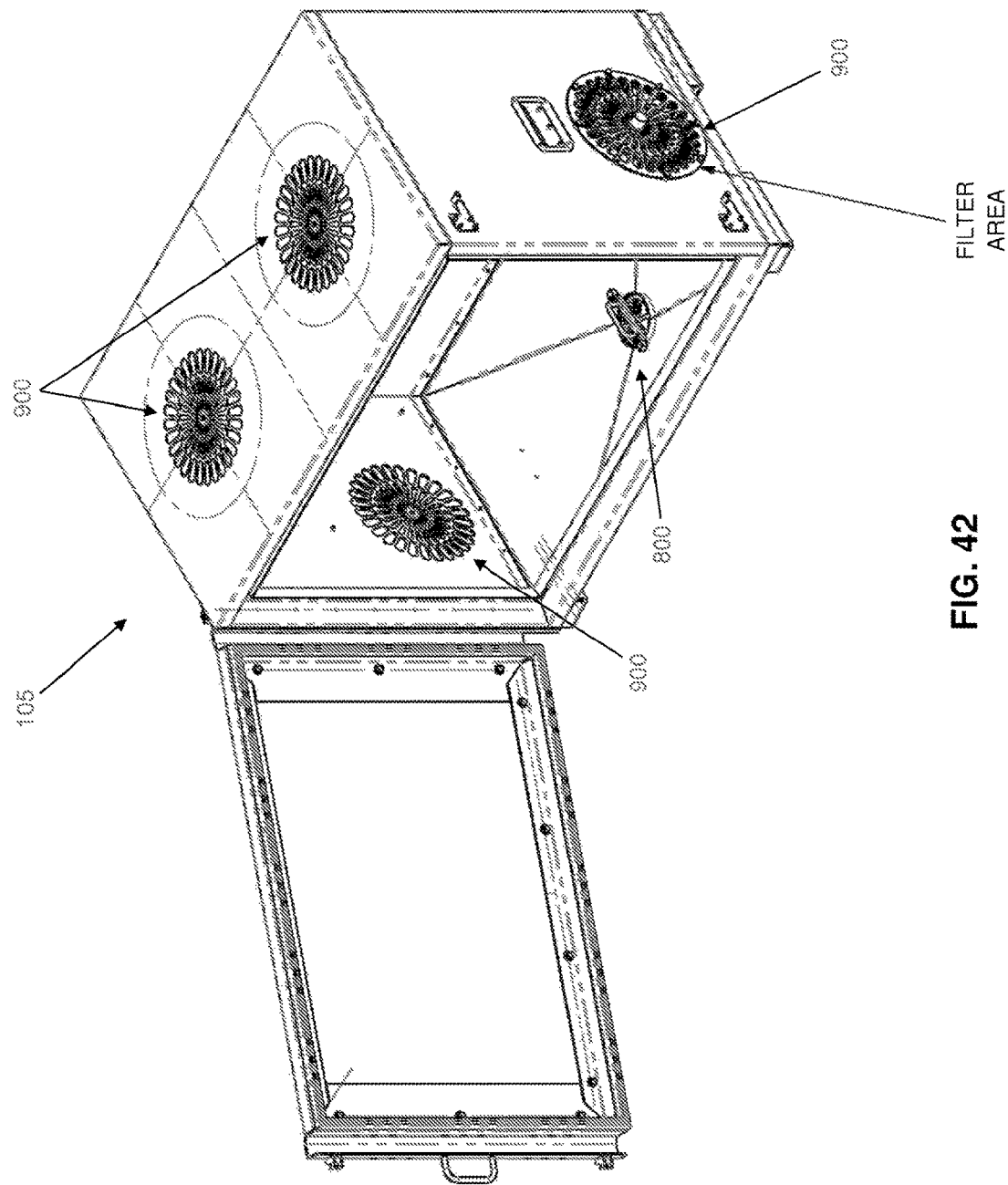
Figure 43:
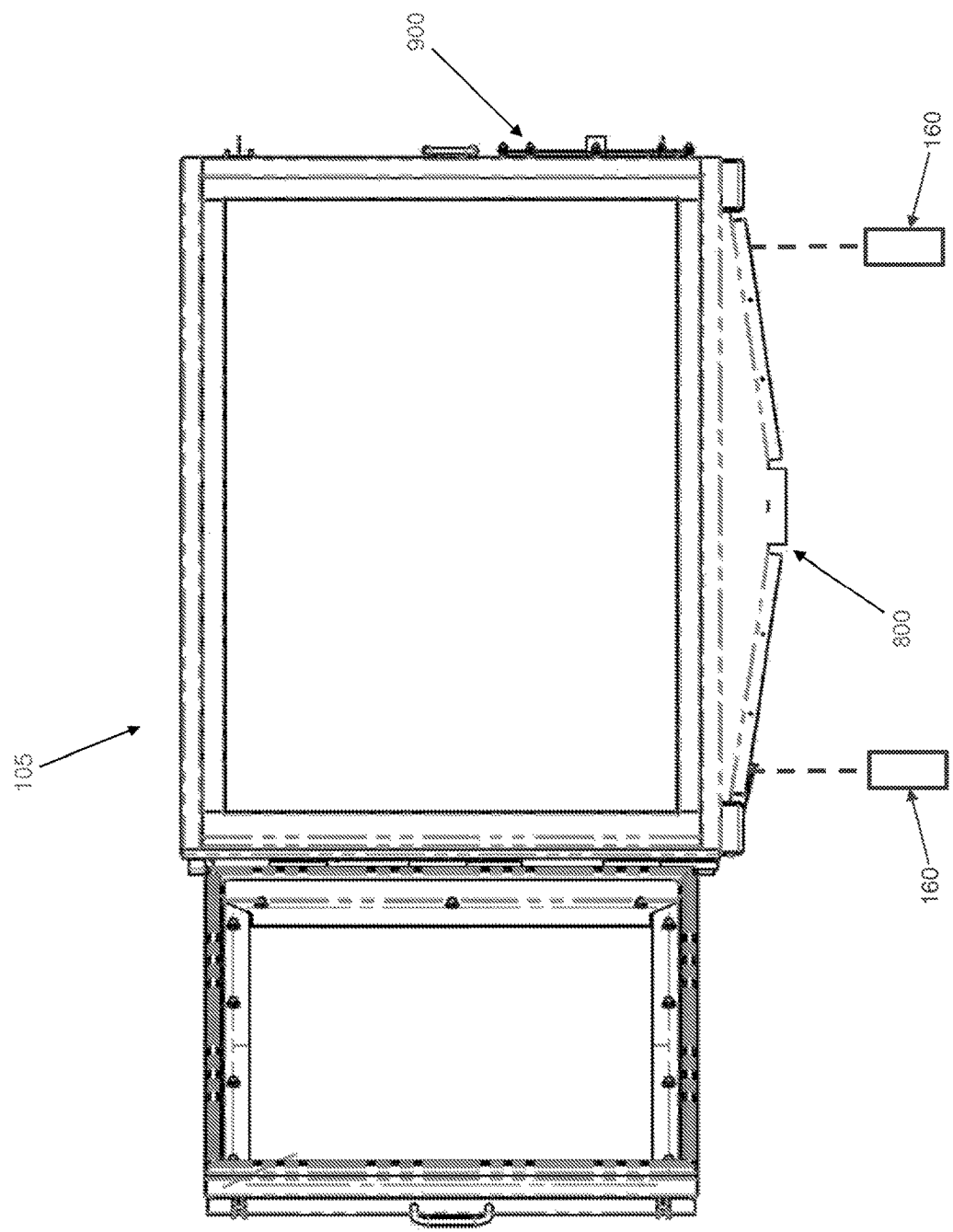
Figure 44:
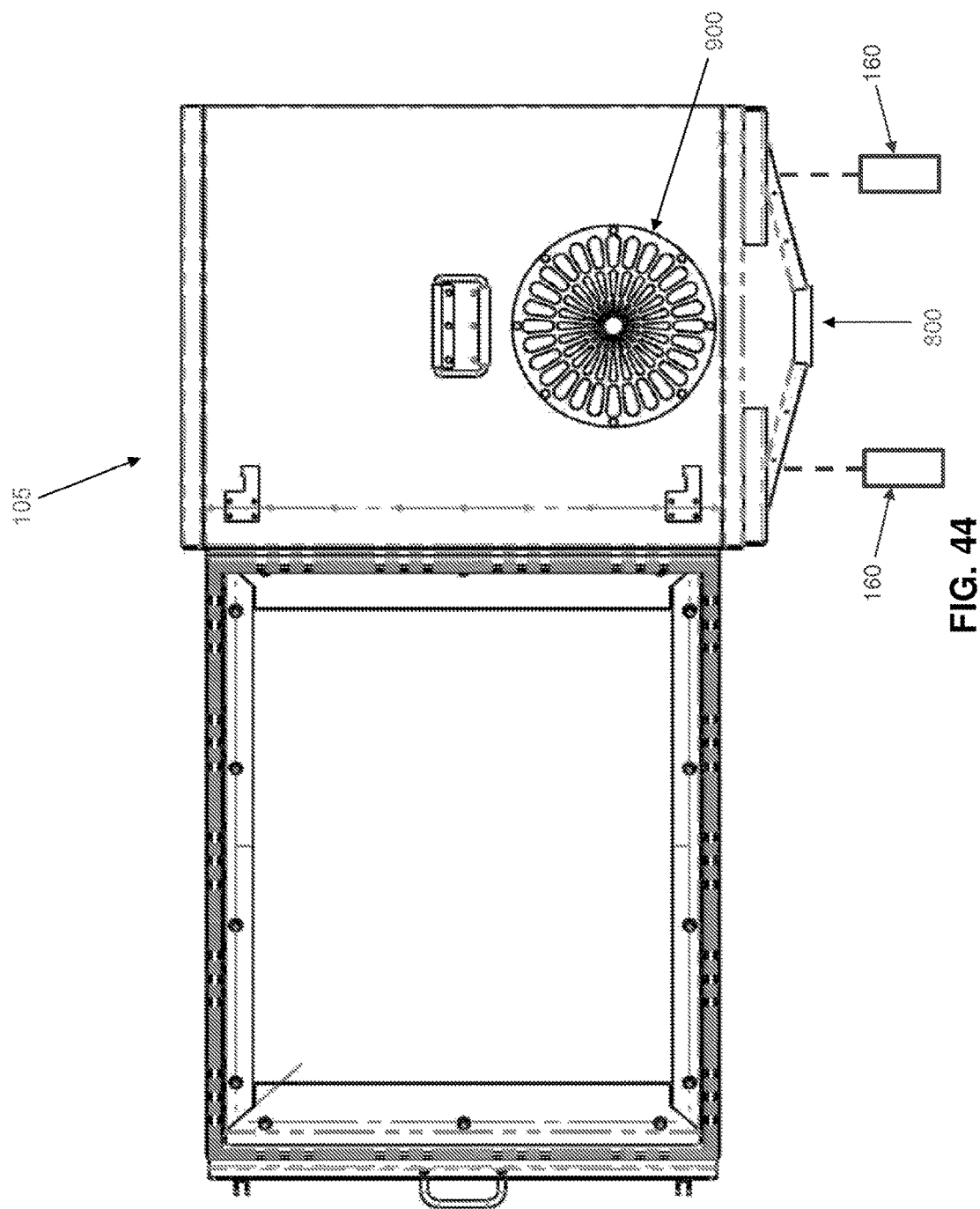

In addition, and looking now at FIG. 27, an external indicator 197 positioned on the cabinet itself may indicate when the cabinet is too hot to touch (e.g., by "lighting up" or otherwise making the "hot" indicator more visually prominent than the "cold" indicator) and/or making the "hot" indicator less visually apparent when the cabinet has reached appropriate handling temperature. Similarly, another indicator 198 may indicate whether the door of the cabinet has been opened (e.g., by "lighting up" or otherwise making the "UNSTERILE" indicator more visually prominent than the "STERILE" indicator). The indicators may also provide other information to a user in the manner described above (e.g., whether the door has been "OPENED" or has remained "CLOSED").

Sterilization Cabinet Sizing and Configurations

Sterilization cabinet 105 can be fabricated in many sizes including, but not limited to, sterilization cabinets that can be specifically sized to receive four trays, or eight trays, or nine trays, or twelve trays, etc.

Furthermore, and looking now at FIG. 28, each size cabinet can also be manufactured with separate external shelving 600 positioned on the exterior of one or more side walls 126 for maximizing space usage (e.g., in the autoclave chamber for each cycle in the autoclave). External shelving 600 can accommodate additional trays of wrapped instruments or rigid containers and is attachable to cabinet 105 for easy unloading when the cycle is completed. External shelves 600 may be individually mounted to the outside of cabinet 105 (as in the case of external shelving 600). Alternatively, the external shelves can take the form of a rack 650 which can be removably attached (e.g., clipped to) a side wall 126 of sterilization cabinet 105. Each shelving unit may come with its own transfer cart according to the size needed, and all shelves may be compactible or foldable for easy storage when not in use.

Construction Materials

Sterilization cabinet 105 has many options with respect to the raw materials for cabinet production. In one preferred form of the invention, sterilization cabinet 105 may be manufactured out of stainless steel. However, it should be appreciated that sterilization cabinet 105 can also be manufactured out of various materials in addition to stainless steel, including but not limited to aluminum (which may allow for a lighter version of the product and the potential for multiple color options during anodizing), or a polymer.

If desired, door handle 132, deadman's safety grip 240 and any other surfaces that may be handled in order to move mobile sterilization system 100 may be covered with a disposable sanitary wrap or film in accordance with sterile procedures.

Alternative Configurations

Sterilization cabinet 105 can also be configured to be used as a "back table" during a medical procedure. More particularly, once the sterilization cabinet is opened (e.g., via either the door configurations discussed above, and/or the dome top discussed above, etc.), the shelves can be displayed to the user using a "toolbox" or "tackle box" design, swinging shelves, or movable shelf system, thereby allowing easy access to all of the inner trays.

Manufacturing Technique

Looking now at FIG. 29, there is shown an exploded diagram of an embodiment of sterilization cabinet 105 which is "bolted together" around an internal frame. More particularly, sterilization cabinet 105 may comprise a frame 112, and side walls 126, rear wall 127, top wall 140 and bottom wall 125 may be attached to frame 112 to form interior chamber 110 of cabinet 105. Each of the walls may be attached to frame 112 by bolts 113 or other suitable means. A sealant 114 or O-ring type seal (not shown) may be placed at the interface of frame 112 and between each of the walls so as to ensure an air-tight seal.

In another embodiment of the present invention, and looking now at FIG. 30, each of the walls of sterilization cabinet 105 may be bolted together without a frame. In this embodiment, each of the side, back, top and bottom panels are attached to one another with bolts 113, with a layer of sealant 114 being applied to the interface between each of the panels.

The embodiments of the invention shown in FIGS. 29 and 30 may provide additional advantages including, but not limited to, reduced shipping costs, inasmuch as the disassembled sterilization cabinet could be shipped in a smaller shipping container (e.g., with the top, bottom, side and back panels and door(s) lying flat against one another). The sterilization cabinet can then be assembled on-site by appropriately trained personnel, who could then verify proper assembly (including an air tight seal) by biological testing methods well known to those in the art.

Docking Station

Mobile sterilization system 100 may also be configured for use with an optional docking station. Looking now at FIG. 30E, docking station 700 comprises a frame 705 and wheels 715. The frame 705 provides a space 720 for receiving one or more sterilization cabinets 105. Docking station 700 preferably also comprises shelves 725 (which can receive additional sterilizable instrument containers). Docking station 700 is itself sterilizable and may be placed directly in an autoclave.

In one preferred form of the invention, transfer cart 200 and docking station 700 are configured to be releasably secured to one another. In this form of the invention, a user may bring transfer cart 200 (carrying sterilization cabinet 105) up to docking station 700 and then releasably secure transfer cart 200 to docking station 700 (or otherwise ensure that neither transfer cart 200 nor docking station 700 will move during transfer of sterilization cabinet 105 from transfer cart 200 to docking station 700); cabinet 105 may then be easily moved from transfer cart 200 onto docking station 700. Transfer cart 200 may then be detached from docking station 700 and docking station 700 (and its passenger containers) moved into the autoclave for sterilization.

Some advantages of using docking station 700 in conjunction with mobile sterilization system 100 include but are not limited to: (i) more efficient use of autoclave space inasmuch as the sterilization cabinet 110 may be placed on docking station 700 which is also loaded with additional containers requiring sterilization; and (ii) freeing up transfer cart 200 for other uses after sterilization cabinet 105 is transferred from transfer cart 200 to docking station 700.

In this respect it should be noted that, in some forms of the invention, transfer cart 200 is not intended to be sterilizable (e.g., where transfer cart 200 carries heat- and moisture-sensitive components such as electronics, etc.).

Improved Condensation Drain and Filter Ports

In still another form of the present invention, an improved condensation drain and filter port is provided for significantly enhancing the performance of sterilization cabinet 105.

More particularly, it has been discovered that the removal of condensate from a sterilization cabinet in its liquid form (as opposed to by evaporation) significantly enhances the performance of a sterilization cabinet. It has been found that steam used during the sterilization process generates a substantial amount of condensate (i.e., liquid water) during the sterilization process. The condensate flows by gravity to the lowest point of the sterilization cabinet. During the drying phase of the sterilization process, a vacuum acts on the autoclave chamber. As the pressure of sterilization cabinet is equalizing with that of the autoclave, the condensation is pulled through a drain (more particularly described below) disposed at the lowest point of the sterilization cabinet and out of sterilization cabinet.

More particularly, in another preferred embodiment of the invention, and looking now at FIGS. 31-45, there is provided an improved drain 800 configured to allow condensate to escape sterilization cabinet 105 without compromising its sterility. Drain 800 is disposed at the lowest point in bottom wall 125 of sterilization cabinet 105. Preferably, sterilization cabinet 105 comprises a pitched floor so that any condensate is directed by gravity to the lowest point in bottom wall 125.

Drain 800 comprises a recess 805 formed below the lowest point in bottom wall 125 of sterilization cabinet 105. Configuring the drain in this manner prevents any residual moisture from remaining in cabinet 105. Recess 805 may be formed of thick stainless steel or other material so as to retain heat and enhance evaporation of any condensate that has flowed into recess 805.

Drain 800 preferably comprises a grill plate/screened floor 810 disposed over recess 805. Grill plate/screened floor 810 provides a rigid platform to support a filter (as is more particularly described below). Grill plate/screened floor 810 is permeable so as to allow condensate to pass through it. A filter 815 is disposed on top of grill plate/screened floor 810. Filter 815 is configured so as to allow condensate to pass through it and out of sterilization cabinet 105 while preventing contaminants from entering sterilization cabinet 105.

A rigid filter door 820 is disposed across recess 805 and on top of filter 815, thereby capturing filter 815 between filter door 820 and grill plate/screened floor 810. Filter door 820 comprises perforations 825 to allow condensate to pass from sterilization cabinet 105 through filter door 820. Filter door 820 is also formed with handle 830, which is held in place by handle brackets 835. Handle 830 allows a user to easily remove filter door 820 (as described below) so as to provide access to filter 815 so that filter 815 may be changed as required. Filter 815 may be changed by removing filter door 820 by twisting handle 830 out from under handle brackets 835.

One or more gaskets (not shown) may be placed against one or more sides of filter 815 (e.g., between filter door 820 and filter 815, and/or between filter 815 and grill plate/screened floor 810) so as to form a seal to prevent the passage of microbial contamination.

In addition to the foregoing, it has also been discovered that it may be advantageous to configure sterilization cabinet 105 with improved filter ports 900 (FIG. 36) disposed in the side wall 126 of sterilization cabinet 105 (in lieu of or in addition to other locations) to allow for improved steam penetration and airflow and to provide an improved vent-to-volume ratio. Filter ports 900 may be configured to be circular portals in the panels of sterilization cabinet 105. Filter ports 900 are covered with circular plates 905 so as to allow for a single point of attachment 910 (e.g., at the center of the circle) and for an even compression of filter gaskets (more particularly described below).

Filter ports 900 comprise a filter 915 and a plate 905 having perforations 920, with filter 915 and plate 905 being mounted to the outside of sterilization cabinet 105, or mounted to the inside of sterilization cabinet 105, in alignment with perforations formed in the side panels of sterilization cabinet 105. Perforations 920 allow for the passage of steam into and out of the sterilization cabinet 105. One or more filters 915 are positioned intermediate the circular plate 905 and cabinet 105 and prevent the passage of microbial contamination therethrough.

Circular plates 905 are provided with gaskets (not shown) so as to create an effective seal between plate 905 and filter 915. Plates 905 are also provided with a twist handle (not shown) which allows for plate 905 to be locked into place and for easy removal when a change of filter 915 is required.

In one preferred form of the invention, filter 915 is disposed intermediate plate 905 and the outside of a side panel of sterilization cabinet 105 so as to allow filter 915 to be accessed from the outside of sterilization cabinet 105. In another preferred form of the invention, filter 915 is disposed intermediate plate 905 and the inside of a panel of sterilization cabinet 105 so as to allow filter 915 to be accessed from the inside of sterilization cabinet 105 for added filter protection. Filter ports 900 may also be provided with covers (not shown) to prevent damage during transportation.

Filter ports 900 and the components thereof are more consistent with the design of other rigid containers in the marketplace, thereby allowing for a crossover of intuitive training and also for a preferred manufacturing process.

FIG. 46A-46F illustrates an improved method for maintaining and ensuring sterility of the chamber 110 of a sterilization container/cabinet 105. FIG. 64 illustrates a sterilization cabinet 105 that includes one or more vented areas or vents 430 in a panel of a wall 126, door 130, back panel or floor 125 of the cabinet. The illustrated cabinet 105 shows vents 430 in a door 130 and side walls 126 of the cabinet 105 for illustrative purposes only. Variations of the cabinet 105 can include one or more vents in any location of the cabinet's panels including the top or bottom of the cabinet 105. In addition, the vents 430, fitters 432, 434, retainer 436, and/or seal 440 can include circular shapes as illustrated or other non-circular configurations. The vents can include any fluid permeable configuration such that a sterilization agent can pass through during a sterilization cycle (including but not limited to a typical autoclave sterilization cycle). The sterilization cabinet 105 illustrated in these figures is shown without any shelving or components within the cabinet 105 for purposes of illustrating affixing the double filter to the container 105.

Figure 46A:
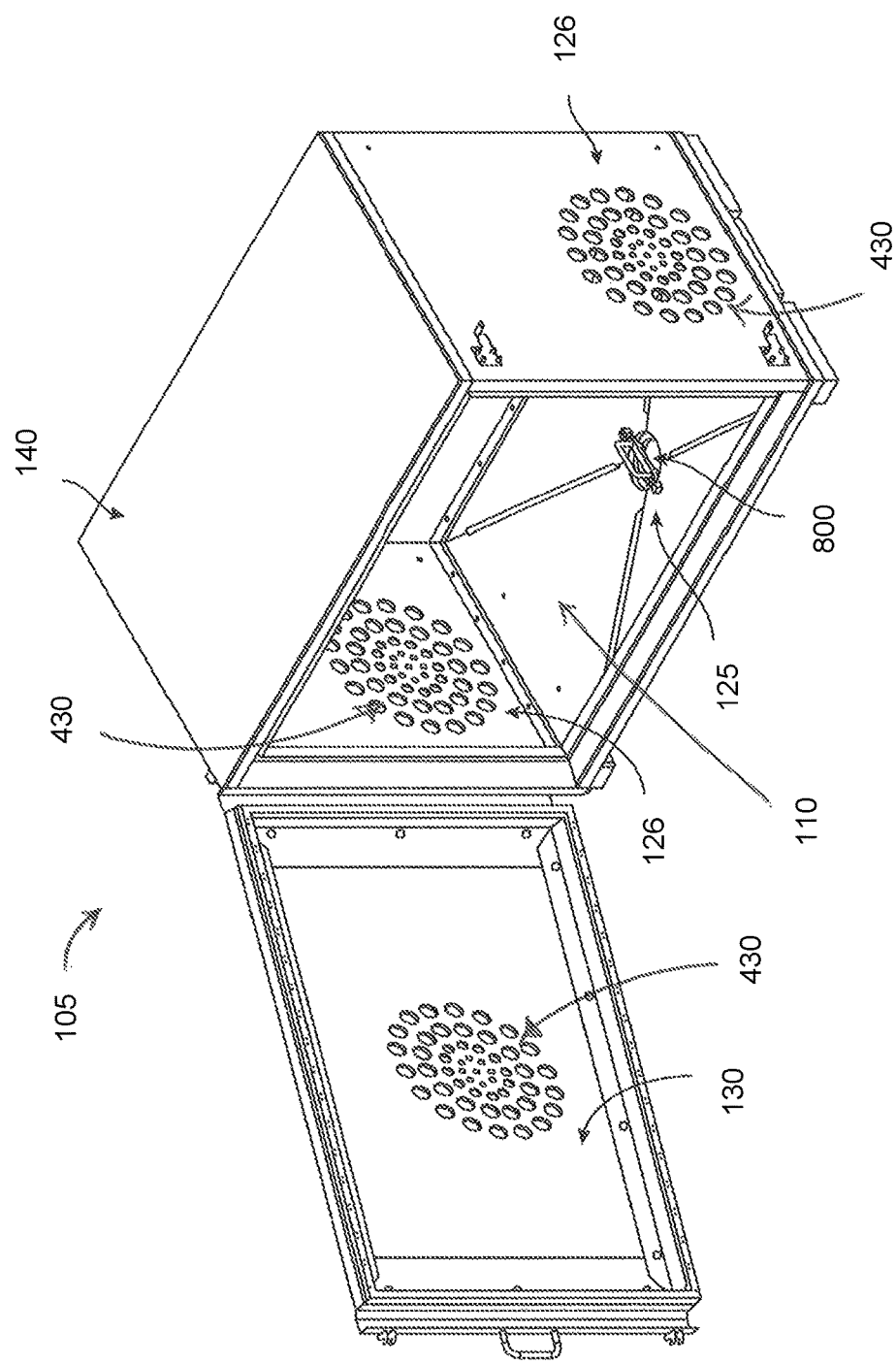
FIG. 46A-46F illustrates an improved method for maintaining and ensuring sterility of a chamber of a sterilization container/cabinet.
Figure 46B:
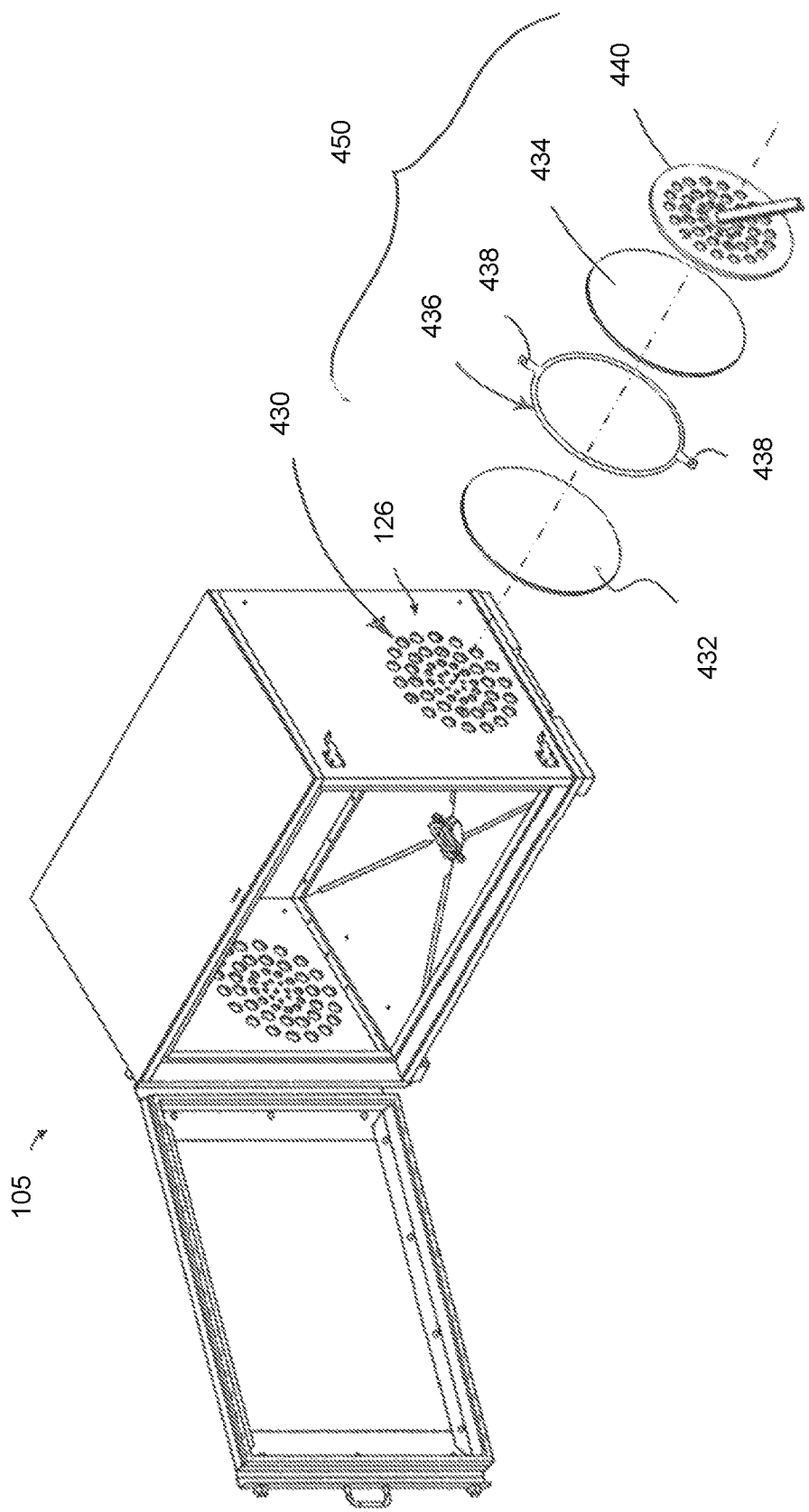

FIG. 46B illustrates an exploded view of a filter-seal assembly 450. As illustrated, the filter-seal assembly 450 includes a first filter 432, an engagement member, which in this example is shown as a retainer member/frame 436, a second filter 434 and a sealing member or filter cover 440. The filters 432, 434 can include any fluidly permeable filter material commonly used for filtration systems, especially those used for sterilization systems.

Figure 46C:
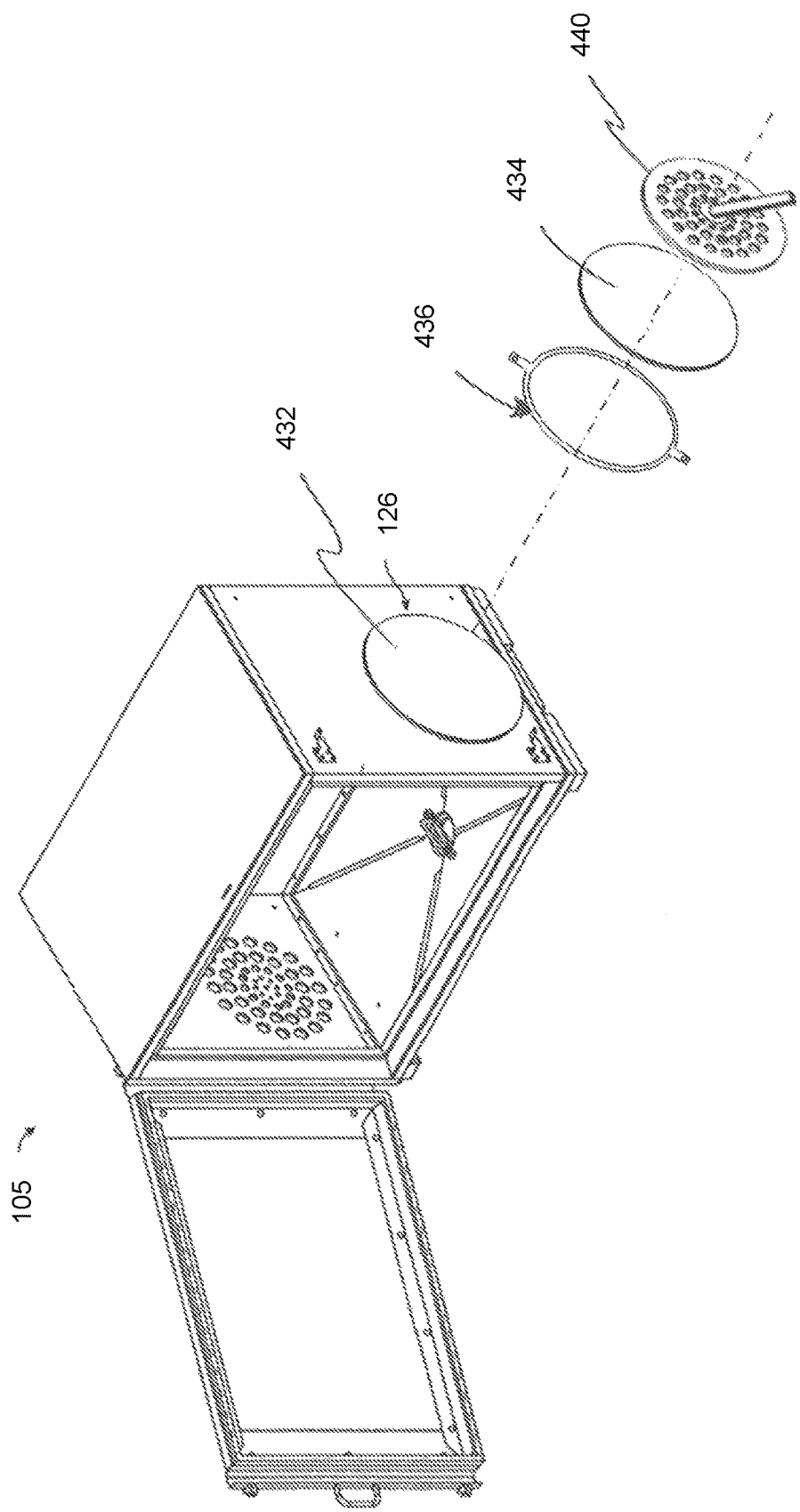
Figure 46D:
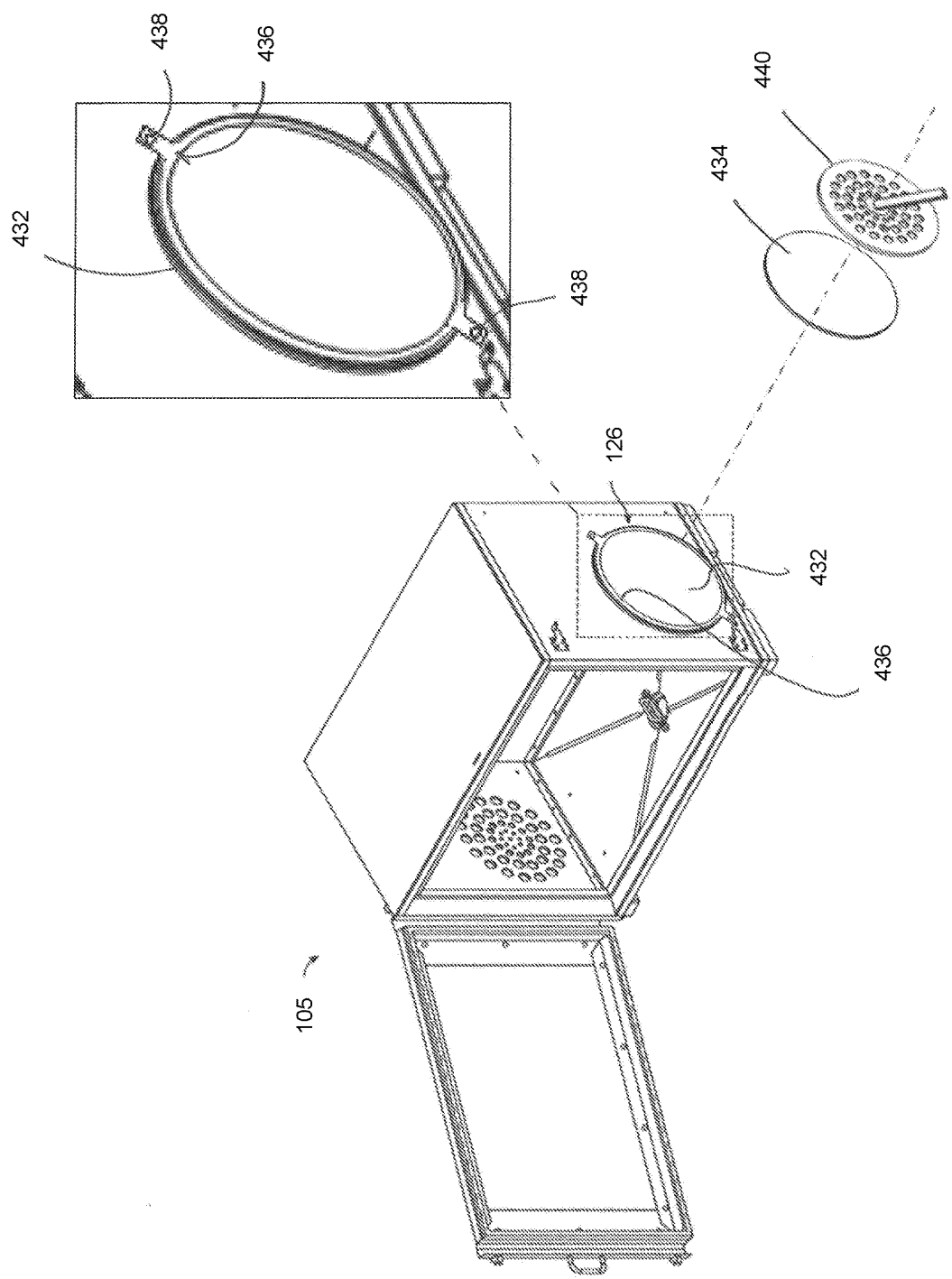

FIG. 46C shows placement of the first filter 432 against a side wall panel 126 of the unit 105. The first filter 432 encircles or spans beyond the vent area 432 so that fluid entering or exiting the adjacent vent 430 must also pass through the filter 432. FIG. 46D illustrates engaging the first filter 432 to the side panel 126. In the illustrated variation, the filter 432 is engaged to the side panel 126 using a retainer member/frame 436. The retainer member/frame 436 can be secured to the container 105/side panel 126 using standard attachment methods. For example, the panel can include one or more protrusions/threaded rods (not illustrated) that extend outward allowing openings 438 in the retainer member/frame 436 to be positioned over the protrusion such that the retainer member/frame 436 removably engages the first filter 432 to the container 105.

Figure 46E:
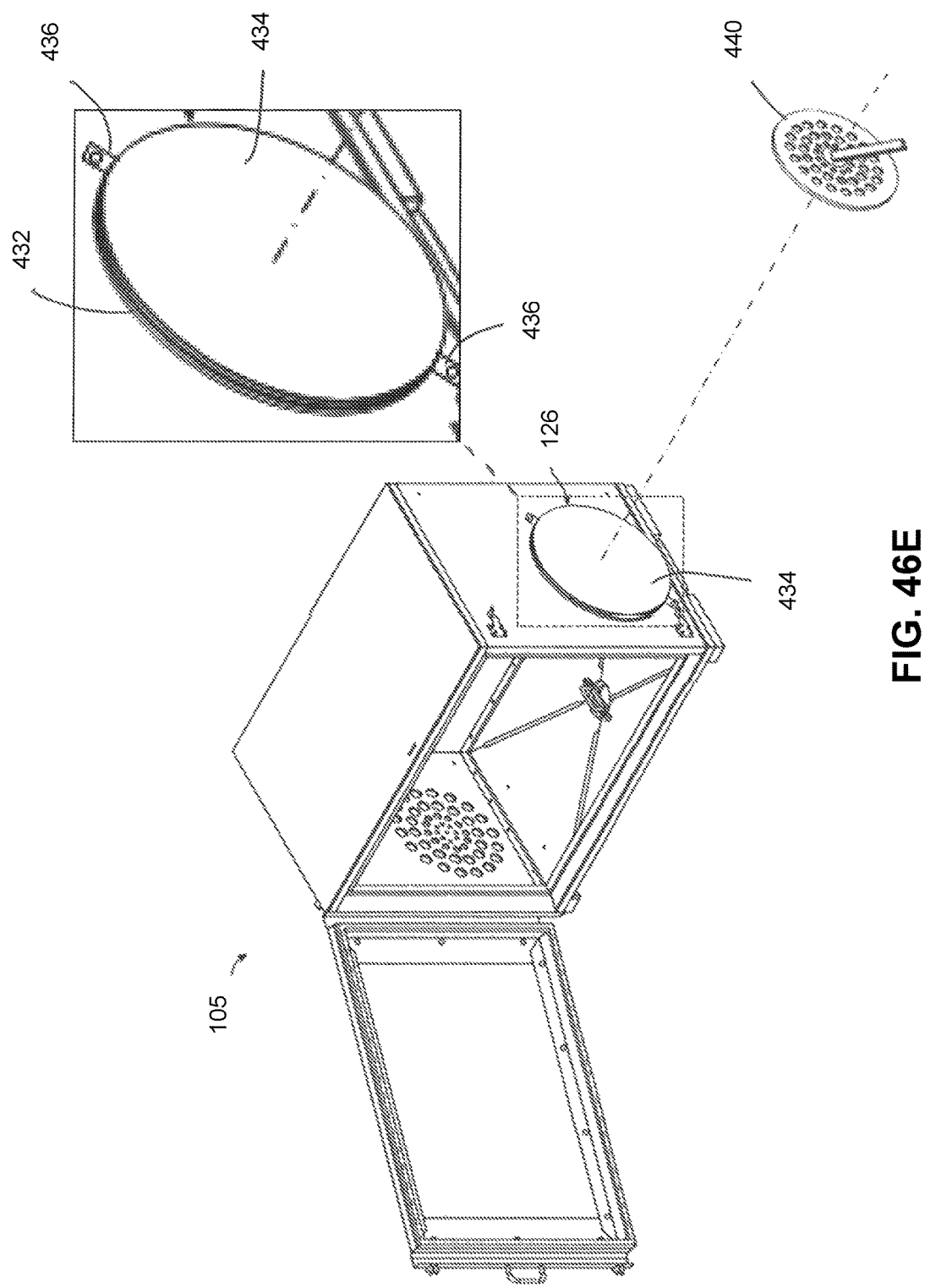

As discussed below, engaging of the first filter 432 to the container 105 is desired for checking the integrity of a seal formed by the filter-seal assembly 450 after the container 105 is processed through a sterilization cycle. The first filter 432 must remain engaged against the container 105 upon disassembly of the seal member 440 and the second filter 434. This construction/feature prevents potential contaminants from entering the container during the unloading process of the instrument tray. Any conventional means can be used to retain first filter 432 against the container 105. For example, the container 105 can include a retainer member coupled thereto by a hinge assembly (not shown). Alternatively, or in combination, the container 105 can include one or more clamping structures that releasably engages the first filter 432 against the cabinet wall 126. In certain variations, the retainer member/frame 436 extends beyond (or encircles) a perimeter of the vent 430 but remains engaged against the container 105 to sandwich the first filter 432 against the container 105. Next, as shown in FIG. 46E, the second filter 434 is positioned over the retainer member/frame 436. In the illustrated example, the perimeter of the second filter 434 is equal in to a perimeter of the first filter 432, but the second filter can extend beyond the first filter 432 or can be sized smaller than the first filter 432 as long as it engages the outward side of the retainer member/frame 436.

Figure 46F:
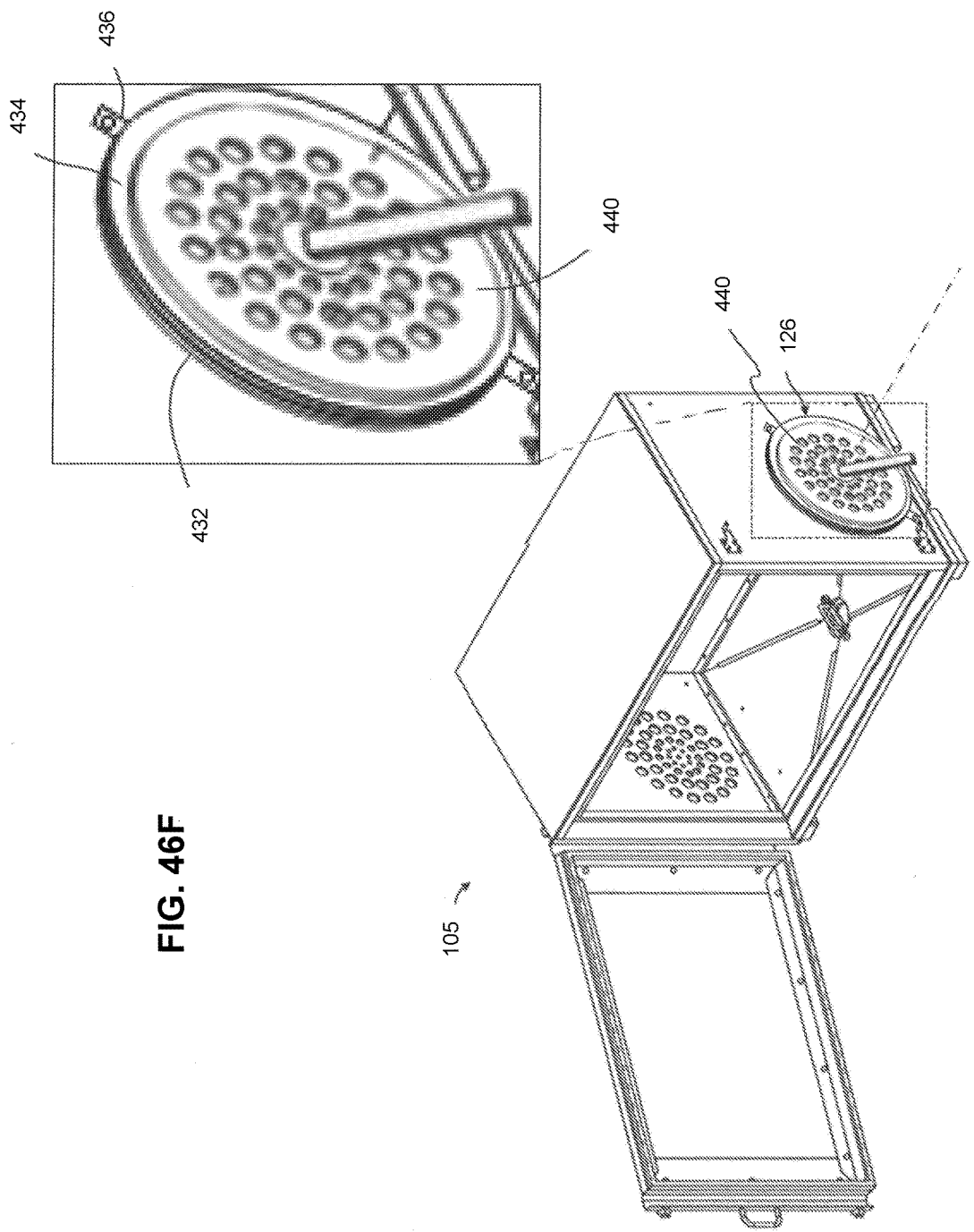

FIG. 46F illustrates securing of a filter cover 440 onto the second filter 434. The filter cover is designed to cause a seal against the sterilization container 105 such that any fluids entering or exiting the container 105 must pass through the porous/permeable region of the filter cover 440. In certain variations, securing the filter cover 440 causes an edge of the filter cover 440 to engage the second filter 434 directly against the first filter 432 and the first filter 434 against the panel 126 (or against the container 105) such that the edge of the filter cover 440 forms a seal simultaneously with both the first filter 432 and the second filter 434 against the sterilization unit 105. Alternatively, the seal can form sequentially.

In the variations illustrated in FIGS. 46A to 46F, the engagement of the first filter against the sterilization container 105 does not form a seal. Instead, it only causes retention of the filter 432 against the unit 105. The only seal formed about an individual vent is formed by the filter cover 440 as described above. The purpose of retaining the first filter against the unit is to prevent the passage of airborn contaminants from entering the container during the process of unloading the contents of the container. The remaining first filter essentially acts as a dust cover. The retention of the first filter against the unit may be accomplished by a ring or a frame of any kind, with or without a gasket forming a complete seal. The primary purpose of this dust cover is to allow thorough inspection of the integrity of the outermost filter and visual confirmation of the presence and integrity of the innermost filter, enabling the technician to have a high level of confidence that the contents are sterile. This prevents the need to set up a secondary back table until confirmation of the filter integrity can be made. The technician is able to unload the contents of the container directly to the surgical back table, eliminating a step in the process of the OR set up. There is a reasonable inference that can be made that if the outermost filter is not compromised, it is extremely unlikely that the innermost filter is compromised. The innermost filter can then be examined more closely after the contents of the container have been aseptically transferred to the back table.

Although the various illustrations show the container 105 in an open configuration, the container can be sealed with medical devices therein either before or after application of the filter seal assemblies. Once the container is secured (e.g., the door is closed and seals are formed at each filter) the container 105 is subject to one or more a sterilization cycles that sterilizes an internal region of the sterilization unit.

Once the sterilization cycle ends, the container 105 is removed from the autoclave or other sterilization apparatus. The sterilization container 105 can then be transferred to a storage area or a surgical area. Prior to opening the sterilization container 105 in a sterile area, a medical technician will check to ensure that the integrity of the filters is not compromised. The technician will then loosen the filter cover from the sterilization unit to disengage the seal of the edge from the second filter 434 (see FIG. 46E). The second filter is then detached from both the first filter and the sterilization unit (as shown in FIG. 46D), where the first filter remains engaged to the panel (in this case through the use of the retainer member/frame 436). The technician can then examine the second filter to assess it for integrity without removing the first filter from the sterilization unit. This integrity check of the second filter 434 allows confirmation that the integrity of the first filter 432 is not compromised. Because the sterilization cycle typically uses steam, high pressure and elevated temperatures, the filters 432, 434 have a tendency to stick together. The use of the double filter system described herein, which allows the first filter to remain engaged with the container 105, allows confirmation of the seal integrity without removing the filter 432 from the container 105.

Every minute of setup time in the OR is extremely costly to the facility. Steps removed from the OR setup process are valuable not only financially but also add to patient safety. Delays in room setup caused by compromised sterility of instruments are far too common. This method of thoroughly examining the outermost filter(s) first while leaving a dust cover for added protection against contaminants, then removing the contents of the container directly to the surgical back table, followed by examination of the innermost filter(s) for final confirmation that the contents remained sterile, allows for greater assurance of sterility of the instruments and a higher probability of performing best practice standards.

MODIFICATIONS

It should also be understood that many additional changes in the details, materials, steps and arrangements of parts, which have been herein described and illustrated in order to explain the nature of the present invention, may be made by those skilled in the art while still remaining within the principles and scope of the invention.

The invention claimed is:

1. A method for confirming integrity of a sterilization container, the method comprising:
   closing a sterilization container having at least one vented area that allows fluids to pass into and out of the sterilization container where the at least one vented area is located in a panel of the sterilization container;
   positioning a first filter to fully cover the at least one vented area and such that the first filter extends beyond a perimeter of the at least one vented area;
   engaging a portion of the first filter to the panel of the sterilization unit at an area beyond the perimeter of the at least one vented area where without sealing the first filter to the panel;
   positioning a second filter over the first filter such that the second filter covers the at least one vented area;
   affixing an edge of a filter cover against the sterilization unit to engage the second filter directly against the first filter and the first filter against the panel such that the edge forms a seal with both the first filter and the second filter against the sterilization unit;
   loosening the filter cover from the sterilization unit to disengage the seal of the edge from at least the second filter against the sterilization cabinet after the sterilization unit completes a sterilization cycle;
   detaching the second filter from both the first filter and the sterilization unit, where the first filter remains engaged to the panel; and examining the second filter to assess an integrity of the first filter without removing the first filter from the sterilization unit.

2. The method of claim 1, where engaging the portion of the first filter to the panel of the sterilization unit comprises securing the first filter between the panel of the sterilization unit and a frame plate, where the frame plate is secured to the panel.

3. The method of claim 2, where the frame plate is detachably secured to the panel.

4. The method of claim 2, where the frame plate is moveable secured to the panel.

5. The method of claim 4, further comprising a hinge moveably securing the frame plate to the panel.

6. The method of claim 2, where the frame plate comprises a ring shape.

7. The method of claim 2, where the frame plate comprises a material selected from the group consisting of a metal, a polymer, a composite material.

8. The method of claim 2, where the frame plate is disposable.

9. The method of claim 8, further comprising using a transfer cart to relocate the sterilization cabinet.

10. The method of claim 8, further comprising using a transfer cart to relocate the sterilization cabinet to a second transportation vehicle.

11. The method of claim 2, where the frame plate is reusable.

12. The method of claim 2, where the edge of the filter cover is positioned within a perimeter of the frame plate.

13. The method of claim 1, where closing the sterilization container comprises loading at least one surgical tray containing a surgical instrument into the interior sterilization container prior to closing the sterilization container.

14. The method of claim 1, further comprising relocating the sterilization cabinet from a sterile location after examining the second filter to assess the integrity of the first filter without removing the first filter from the sterilization unit.

15. A method for sterilizing a medical item, the method comprising:

securing a sterilization container with the medical item therein wherein the sterilization container includes at least one vented area in a panel allowing fluids to pass into and out of the sterilization container;

positioning a first filter to cover the at least one vented area and extend beyond a perimeter of the at least one vented area;

engaging a portion of the first filter to the panel of the sterilization container at an area beyond the perimeter of the at least one vented area without sealing the first filter to the panel;

positioning a second filter over the first filter such that the second filter covers the at least one vented area;

affixing an edge of a filter cover against the sterilization container to engage the second filter directly against the first filter and the first filter against the panel such that the edge forms a seal with the first filter and the second filter against the sterilization container;

loosening the filter cover from the sterilization container to break the seal of the edge, the first filter, and the second filter against the sterilization container after the sterilization unit completes a sterilization cycle;

detaching the second filter from both the first filter and the sterilization container, where the first filter remains engaged to the panel; and examining the second filter to assess an integrity of the second filter once detached.

16. The method of claim 15, where engaging the portion of the first filter to the panel of the sterilization unit comprises securing the first filter between the panel of the sterilization unit and a frame plate, where the frame plate is secured to the panel.

17. The method of claim 16, where the frame plate is detachably secured to the panel.

18. The method of claim 16, where the frame plate is moveable secured to the panel.

19. The method of claim 18, further comprising a hinge moveably securing the frame plate to the panel.

20. The method of claim 16, where the frame plate comprises a ring shape.

* * * * *